United States Patent
Pulé et al.

(10) Patent No.: US 11,851,672 B2
(45) Date of Patent: Dec. 26, 2023

(54) CAR T-CELLS COMPRISING TRANSCRIPTIONAL CIRCUITS

(71) Applicant: AUTOLUS LIMITED, London (GB)

(72) Inventors: Martin Pulé, London (GB); James Sillibourne, London (GB); Shaun Cordoba, London (GB)

(73) Assignee: AUTOLUS LIMITED, London (GB)

( * ) Notice: Subject to any disclaimer, the term of this patent is extended or adjusted under 35 U.S.C. 154(b) by 682 days.

(21) Appl. No.: 16/759,222

(22) PCT Filed: Oct. 24, 2018

(86) PCT No.: PCT/GB2018/053088
§ 371 (c)(1),
(2) Date: Apr. 24, 2020

(87) PCT Pub. No.: WO2019/081935
PCT Pub. Date: May 2, 2019

(65) Prior Publication Data
US 2020/0308600 A1    Oct. 1, 2020

(30) Foreign Application Priority Data
Oct. 25, 2017 (GB) ..................... 1717524

(51) Int. Cl.
C12N 15/86 (2006.01)
A61K 35/17 (2015.01)
A61K 48/00 (2006.01)

(52) U.S. Cl.
CPC .............. *C12N 15/86* (2013.01); *A61K 35/17* (2013.01); *A61K 48/00* (2013.01); *C12N 2740/10043* (2013.01); *C12N 2800/40* (2013.01)

(58) Field of Classification Search
None
See application file for complete search history.

(56) References Cited

FOREIGN PATENT DOCUMENTS

| JP | 2016214093 | * | 12/2016 |
|---|---|---|---|
| JP | 2016214093 | A | 12/2016 |
| WO | WO-2006/063247 | A2 | 6/2006 |
| WO | WO-2013/153391 | A1 | 10/2013 |
| WO | WO-2015/075470 | A1 | 5/2015 |
| WO | WO-2015/150771 | A1 | 10/2015 |
| WO | WO-2016/030691 | A1 | 3/2016 |
| WO | WO-2016/055551 | A1 | 4/2016 |
| WO | WO-2016/124930 | A1 | 8/2016 |
| WO | WO-2016/135470 | A1 | 9/2016 |
| WO | WO-2016/193696 | A1 | 12/2016 |
| WO | WO-2017/029512 | A1 | 2/2017 |
| WO | WO-2017/035251 | A1 | 3/2017 |
| WO | WO-2017/079673 | A1 | 5/2017 |

OTHER PUBLICATIONS

International Search Report and Written Opinion from International Application No. PCT/GB2018/053088 dated Jan. 21, 2019.
Lopez et al., "Dominant Negative Mutants of Transforming Growth Factor-b1 Inhibit the Secretion of Different Transforming Growth Factor-β Isoforms," Molecular and Cellular Biology 1674-1679 (1992).
Rivera et al., "Long-term regulated expression of growth hormone in mice after intramuscular gene transfer," Proc. Natl. Acad. Sci. 96:8657-8662 (1999).
Straathof et al., "An inducible caspase 9 safety switch for T-cell therapy," Blood 105:4247-4254 (2005).

* cited by examiner

*Primary Examiner* — Nicole Kinsey White
(74) *Attorney, Agent, or Firm* — MARSHALL, GERSTEIN & BORUN LLP

(57) ABSTRACT

The present invention provides a kit of vectors for transducing an immune cell with multiple transgenes comprising: (i) a first vector which comprises a first transgene and a nucleotide sequence encoding a transcription factor and; and (ii) a second vector which comprises a second transgene wherein expression of the second transgene within a host cell is dependent upon expression of the transcription factor.

2 Claims, 7 Drawing Sheets

Specification includes a Sequence Listing.

SEQUENCE LISTING

```
<160> NUMBER OF SEQ ID NOS: 47

<210> SEQ ID NO 1
<211> LENGTH: 202
<212> TYPE: PRT
<213> ORGANISM: Escherichia coli

<400> SEQUENCE: 1

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95
```

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200

<210> SEQ ID NO 2
<211> LENGTH: 363
<212> TYPE: PRT
<213> ORGANISM: Escherichia coli

<400> SEQUENCE: 2

Met Val Asn Val Lys Pro Val Thr Leu Tyr Asp Val Ala Glu Tyr Ala
1               5                   10                  15

Gly Val Ser Tyr Gln Thr Val Ser Arg Val Val Asn Gln Ala Ser His
            20                  25                  30

Val Ser Ala Lys Thr Arg Glu Lys Val Glu Ala Ala Met Ala Glu Leu
        35                  40                  45

Asn Tyr Ile Pro Asn Arg Val Ala Gln Gln Leu Ala Gly Lys Gln Ser
    50                  55                  60

Leu Leu Ile Gly Val Ala Thr Ser Ser Leu Ala Leu His Ala Pro Ser
65                  70                  75                  80

Gln Ile Val Ala Ala Ile Lys Ser Arg Ala Asp Gln Leu Gly Ala Ser
                85                  90                  95

Val Val Val Ser Met Val Glu Arg Ser Gly Val Glu Ala Cys Lys Ala
            100                 105                 110

Ala Val His Asn Leu Leu Ala Gln Arg Val Ser Gly Leu Ile Ile Asn
        115                 120                 125

Tyr Pro Leu Asp Asp Gln Asp Ala Ile Ala Val Glu Ala Ala Cys Thr
    130                 135                 140

Asn Val Pro Ala Leu Phe Leu Asp Val Ser Asp Gln Thr Pro Ile Asn
145                 150                 155                 160

Ser Ile Ile Phe Ser His Glu Asp Gly Thr Arg Leu Gly Val Glu His
                165                 170                 175

Leu Val Ala Leu Gly His Gln Gln Ile Ala Leu Leu Ala Gly Pro Leu
            180                 185                 190

Ser Ser Val Ser Ala Arg Leu Arg Leu Ala Gly Trp His Lys Tyr Leu
        195                 200                 205

Thr Arg Asn Gln Ile Gln Pro Ile Ala Glu Arg Glu Gly Asp Trp Ser
    210                 215                 220

Ala Met Ser Gly Phe Gln Gln Thr Met Gln Met Leu Asn Glu Gly Ile
225                 230                 235                 240

Val Pro Thr Ala Met Leu Val Ala Asn Asp Gln Met Ala Leu Gly Ala
                245                 250                 255

Met Arg Ala Ile Thr Glu Ser Gly Leu Arg Val Gly Ala Asp Ile Ser
            260                 265                 270

-continued

```
Val Val Gly Tyr Asp Asp Thr Glu Asp Ser Ser Cys Tyr Ile Pro Pro
            275                 280                 285

Leu Thr Thr Ile Lys Gln Asp Phe Arg Leu Leu Gly Gln Thr Ser Val
        290                 295                 300

Asp Arg Leu Leu Gln Leu Ser Gln Gly Gln Ala Val Lys Gly Asn Gln
305                 310                 315                 320

Leu Leu Pro Val Ser Leu Val Lys Arg Lys Thr Thr Leu Ala Pro Asn
            325                 330                 335

Thr Gln Thr Ala Ser Pro Arg Ala Leu Ala Asp Ser Leu Met Gln Leu
        340                 345                 350

Ala Arg Gln Val Ser Arg Leu Glu Ser Gly Gln
        355                 360

<210> SEQ ID NO 3
<211> LENGTH: 208
<212> TYPE: PRT
<213> ORGANISM: Escherichia coli

<400> SEQUENCE: 3

Met Met Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

<210> SEQ ID NO 4
<211> LENGTH: 881
<212> TYPE: PRT
<213> ORGANISM: Saccharomyces cerevisiae

<400> SEQUENCE: 4

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30
```

```
Lys Asn Asn Trp Glu Cys Arg Tyr Ser Pro Lys Thr Lys Arg Ser Pro
             35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Glu Glu Ser Ser Asn Lys Gly Gln Arg Gln Leu
    130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
                180                 185                 190

Asn Asn Gly Phe Phe Gly Asp Gly Ser Leu Leu Cys Ile Leu Arg Ser
                195                 200                 205

Ile Gly Phe Lys Pro Glu Asn Tyr Thr Asn Ser Asn Val Asn Arg Leu
    210                 215                 220

Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
                245                 250                 255

Ile Val His Ser Pro Thr Leu Met Met Leu Tyr Asn Asn Gln Ile Glu
                260                 265                 270

Ile Ala Ser Lys Asp Gln Trp Gln Ile Leu Phe Asn Cys Ile Leu Ala
                275                 280                 285

Ile Gly Ala Trp Cys Ile Glu Gly Glu Ser Thr Asp Ile Asp Val Phe
    290                 295                 300

Tyr Tyr Gln Asn Ala Lys Ser His Leu Thr Ser Lys Val Phe Glu Ser
305                 310                 315                 320

Gly Ser Ile Ile Leu Val Thr Ala Leu His Leu Leu Ser Arg Tyr Thr
                325                 330                 335

Gln Trp Arg Gln Lys Thr Asn Thr Ser Tyr Asn Phe His Ser Phe Ser
                340                 345                 350

Ile Arg Met Ala Ile Ser Leu Gly Leu Asn Arg Asp Leu Pro Ser Ser
                355                 360                 365

Phe Ser Asp Ser Ser Ile Leu Glu Gln Arg Arg Ile Trp Trp Ser
    370                 375                 380

Val Tyr Ser Trp Glu Ile Gln Leu Ser Leu Tyr Gly Arg Ser Ile
385                 390                 395                 400

Gln Leu Ser Gln Asn Thr Ile Ser Phe Pro Ser Ser Val Asp Asp Val
                405                 410                 415

Gln Arg Thr Thr Thr Gly Pro Thr Ile Tyr His Gly Ile Ile Glu Thr
                420                 425                 430

Ala Arg Leu Leu Gln Val Phe Thr Lys Ile Tyr Glu Leu Asp Lys Thr
                435                 440                 445

Val Thr Ala Glu Lys Ser Pro Ile Cys Ala Lys Lys Cys Leu Met Ile
```

-continued

```
            450                 455                 460
Cys Asn Glu Ile Glu Glu Val Ser Arg Gln Ala Pro Lys Phe Leu Gln
465                 470                 475                 480

Met Asp Ile Ser Thr Thr Ala Leu Thr Asn Leu Leu Lys Glu His Pro
                    485                 490                 495

Trp Leu Ser Phe Thr Arg Phe Glu Leu Lys Trp Lys Gln Leu Ser Leu
                500                 505                 510

Ile Ile Tyr Val Leu Arg Asp Phe Phe Thr Asn Phe Thr Gln Lys Lys
            515                 520                 525

Ser Gln Leu Glu Gln Asp Gln Asn Asp His Gln Ser Tyr Glu Val Lys
            530                 535                 540

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
                565                 570                 575

Asn Cys Ser Tyr Tyr Leu Phe Asn Ala Val Leu Val Pro Ile Lys Thr
                580                 585                 590

Leu Leu Ser Asn Ser Lys Ser Asn Ala Glu Asn Asn Glu Thr Ala Gln
            595                 600                 605

Leu Leu Gln Gln Ile Asn Thr Val Leu Met Leu Leu Lys Lys Leu Ala
610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
                645                 650                 655

Ile Ser Tyr Asn Asn Ser Asn Gly Ser Ala Ile Lys Asn Ile Val Gly
                660                 665                 670

Ser Ala Thr Ile Ala Gln Tyr Pro Thr Leu Pro Glu Gly Asn Val Asn
            675                 680                 685

Asn Ile Ser Val Lys Tyr Val Ser Pro Gly Ser Val Gly Pro Ser Pro
            690                 695                 700

Val Pro Leu Lys Ser Gly Ala Ser Phe Ser Asp Leu Val Lys Leu Leu
705                 710                 715                 720

Ser Asn Arg Pro Pro Ser Arg Asn Ser Pro Val Thr Ile Pro Arg Ser
                725                 730                 735

Thr Pro Ser His Arg Ser Val Thr Pro Phe Leu Gly Gln Gln Gln Gln
                740                 745                 750

Leu Gln Ser Leu Val Pro Leu Thr Pro Ser Ala Leu Phe Gly Gly Ala
            755                 760                 765

Asn Phe Asn Gln Ser Gly Asn Ile Ala Asp Ser Ser Leu Ser Phe Thr
770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Asn Val His Asp Asn
                805                 810                 815

Phe Met Asn Asn Glu Ile Thr Ala Ser Lys Ile Asp Asp Gly Asn Asn
                820                 825                 830

Ser Lys Pro Leu Ser Pro Gly Trp Thr Asp Gln Thr Ala Tyr Asn Ala
            835                 840                 845

Phe Gly Ile Thr Thr Gly Met Phe Asn Thr Thr Met Asp Asp Val
            850                 855                 860

Tyr Asn Tyr Leu Phe Asp Asp Glu Asp Thr Pro Pro Asn Pro Lys Lys
865                 870                 875                 880
```

Glu

<210> SEQ ID NO 5
<211> LENGTH: 816
<212> TYPE: PRT
<213> ORGANISM: Neurospora crassa

<400> SEQUENCE: 5

```
Met Pro Pro Lys Arg Lys Thr Leu Asn Ala Ala Glu Ala Asn Ala
1               5                   10                  15

His Ala Asp Gly His Ala Asp Gly Asn Ala Asp Gly His Val Ala Asn
            20                  25                  30

Thr Ala Ala Ser Ser Asn Asn Ala Arg Phe Ala Asp Leu Thr Asn Ile
            35                  40                  45

Asp Thr Pro Gly Leu Gly Pro Thr Thr Thr Leu Leu Val Glu Pro
    50                  55                  60

Ala Arg Ser Lys Arg Gln Arg Val Ser Arg Ala Cys Asp Gln Cys Arg
65                  70                  75                  80

Ala Ala Arg Glu Lys Cys Asp Gly Ile Gln Pro Ala Cys Phe Pro Cys
                85                  90                  95

Val Ser Gln Gly Arg Ser Cys Thr Tyr Gln Ala Ser Pro Lys Lys Arg
                100                 105                 110

Gly Val Gln Thr Gly Tyr Ile Arg Thr Leu Glu Leu Ala Leu Ala Trp
            115                 120                 125

Met Phe Glu Asn Val Ala Arg Ser Glu Asp Ala Leu His Asn Leu Leu
    130                 135                 140

Val Arg Asp Ala Gly Gln Gly Ser Ala Leu Leu Val Gly Lys Asp Ser
145                 150                 155                 160

Pro Ala Ala Glu Arg Leu His Ala Arg Trp Ala Thr Ser Arg Val Asn
                165                 170                 175

Lys Ser Ile Thr Arg Leu Leu Ser Gly Gln Ala Ala Gln Asp Pro Ser
                180                 185                 190

Glu Asp Gly Gln Ser Pro Ser Glu Asp Ile Asn Val Gln Asp Ala Gly
            195                 200                 205

Ala Lys Thr Ser Asp Phe Pro His Ala Pro His Leu Thr Phe Ser Ala
    210                 215                 220

Pro Lys Ser Ser Thr Ala Glu Thr Arg Thr Leu Pro Gly Pro Val Arg
225                 230                 235                 240

Pro Pro Ile Ser Ala Asn Thr Leu Glu Asn Asn Leu Gln Pro Asp Gly
                245                 250                 255

Thr Gly Ile Gly Lys Leu Pro Pro Asn His Trp Arg Leu Leu Asp Ile
            260                 265                 270

Tyr Phe Ser Tyr Thr His Ser Trp Leu Pro Ile Leu Glu Lys Lys Asp
        275                 280                 285

Met Tyr Gln Ala Leu Tyr Gln Tyr Ser Glu Gln Gly Ser Leu Leu Pro
    290                 295                 300

Ser Ala Asn Val Glu Ser Gly Val His Ala Glu Leu Trp Ser Ala Leu
305                 310                 315                 320

Ala Leu Ala Ser Phe Gln Ala Ala Thr Ala Ser Ser Ala Thr
                325                 330                 335

Gly Pro Ala Ser Ala Ala His Gly His Asp Asn Ala Ile Asn Pro Ser
            340                 345                 350

Pro Ala Asp Ile Ser Asp Thr Ala Arg Lys Leu Ile Pro Leu Glu Ser
    355                 360                 365
```

```
Gly Pro Phe Gln Val Gln His Cys Arg Ala Leu Leu Leu Cys Leu
    370                 375                 380

Val Ser Leu Gly Arg Asp Asp Trp Glu Ser Ala Trp Leu Leu Val Gly
385                 390                 395                 400

Phe Ala Val Arg Val Leu Leu Val Val Arg Thr Gln Leu Pro Pro Asp
                405                 410                 415

Asp Asp Arg Pro Arg Pro Arg Met Arg Ala Leu Leu Val Ala Cys Phe
            420                 425                 430

Ile Val Asp Thr Ile Val Ser Met Arg His Asn Val Pro Ala His Leu
        435                 440                 445

Lys Pro Asp Asp Ile Ala Asp Leu Pro Leu Pro Glu Asp Gly Gln Asp
450                 455                 460

Gln Trp Glu Pro Trp Thr Pro Cys Glu Gly Leu Gly Gly Glu His Thr
465                 470                 475                 480

Met Leu Gln Met Leu Arg Asn Pro Ala Tyr Pro Leu Ser Thr Phe Asn
                485                 490                 495

His Leu Tyr Gly Val Thr Lys Leu Val Ala Leu Glu Leu Leu Pro Arg
            500                 505                 510

Ile Arg Thr Ser Ser Gln Asn Ala Pro Leu Glu Phe Arg Ser Arg Leu
        515                 520                 525

Gln Gln Val Ile Gly His Asn Ser Pro Phe Ser Val Phe Val Leu Ser
530                 535                 540

Gln Asp Thr Ala Ser Ala Phe Val Pro Thr Ala Tyr Leu Thr Arg Thr
545                 550                 555                 560

Val Tyr Leu Trp Ala Ala Ala Phe Ser Glu Pro Leu Asn Glu His Tyr
                565                 570                 575

Ser His Leu Leu Ile Glu Thr Leu Asp Gln Tyr Gln Lys Arg Phe Gly
            580                 585                 590

Thr Tyr Ala Ile Pro Pro Leu Ile Pro Ser Leu Leu Asp Ser Leu Leu
        595                 600                 605

Ala Leu Lys Lys Gln Ser His Ser Ser Glu Arg His Arg Arg His Leu
610                 615                 620

Glu Glu Leu Phe Pro Ala Tyr Ser Ser Ile Trp Pro Arg Gly Gly Arg
625                 630                 635                 640

His Ser Asn Thr Gly Leu Gln Pro Ile Arg Gln Leu Glu Leu Pro Pro
                645                 650                 655

Thr Ala Thr Ala Thr Ala Ser Ile Met Pro His Val Met Glu Gln Pro
            660                 665                 670

Leu Ser Thr Ser Ile Asn Pro Val Asn Asp Arg Phe Asn Gly Ile Pro
        675                 680                 685

Asn Pro Thr Pro Tyr Asn Ser Asp Ala Ala Leu Asp Ala Ile Thr Gln
690                 695                 700

Thr Asn Asp Tyr Gly Ser Val Asn Thr His Gly Ile Leu Ser Thr Tyr
705                 710                 715                 720

Pro Pro Pro Ala Thr His Leu Asn Glu Ala Ser Val Ala Leu Ala Pro
                725                 730                 735

Gly Gly Ala Pro Pro Arg Pro Pro Pro Tyr Val Asp Ser Thr Thr
            740                 745                 750

Asn His Pro Pro Tyr His Ser Asn Leu Val Pro Met Ala Asn Phe Gly
        755                 760                 765

Tyr Ser Thr Val Asp Tyr Asp Ala Met Val Asp Asp Leu Ala Ser Ile
770                 775                 780
```

```
Glu Tyr Thr Asp Ala Val Asp Val Asp Pro Gln Phe Met Thr Asn Leu
785                 790                 795                 800

Gly Phe Val Pro Gly Cys Asn Phe Ser Asp Ile Ser Thr Tyr Glu Gln
            805                 810                 815

<210> SEQ ID NO 6
<211> LENGTH: 93
<212> TYPE: PRT
<213> ORGANISM: herpes simplex virus

<400> SEQUENCE: 6

Glu Phe Pro Gly Ile Arg Arg Pro Ala Gly Ile Pro Gly Asp Leu Ala
1               5                   10                  15

Pro Pro Thr Asp Val Ser Leu Gly Asp Glu Leu His Leu Asp Gly Glu
            20                  25                  30

Asp Val Ala Met Ala His Ala Asp Ala Leu Asp Asp Phe Asp Leu Asp
        35                  40                  45

Met Leu Gly Asp Gly Asp Ser Pro Gly Pro Gly Phe Thr Pro His Asp
50                  55                  60

Ser Ala Pro Tyr Gly Ala Leu Asp Met Ala Asp Phe Glu Phe Glu Gln
65                  70                  75                  80

Met Phe Thr Asp Ala Leu Gly Ile Asp Glu Tyr Gly Gly
                85                  90

<210> SEQ ID NO 7
<211> LENGTH: 295
<212> TYPE: PRT
<213> ORGANISM: Artificial Sequence
<220> FEATURE:
<223> OTHER INFORMATION: amino acid sequence of LexA/VP16 fusion

<400> SEQUENCE: 7

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Arg
```

```
            195                 200                 205
Arg Pro Ala Gly Ile Pro Gly Asp Leu Ala Pro Thr Asp Val Ser
210                 215                 220

Leu Gly Asp Glu Leu His Leu Asp Gly Glu Asp Val Ala Met Ala His
225                 230                 235                 240

Ala Asp Ala Leu Asp Asp Phe Asp Leu Asp Met Leu Gly Asp Gly Asp
                    245                 250                 255

Ser Pro Gly Pro Gly Phe Thr Pro His Asp Ser Ala Pro Tyr Gly Ala
                260                 265                 270

Leu Asp Met Ala Asp Phe Glu Phe Glu Gln Met Phe Thr Asp Ala Leu
            275                 280                 285

Gly Ile Asp Glu Tyr Gly Gly
            290                 295

<210> SEQ ID NO 8
<211> LENGTH: 436
<212> TYPE: PRT
<213> ORGANISM: Artificial Sequence
<220> FEATURE:
<223> OTHER INFORMATION: amino acid sequence of lactose repressor/VP16
      fusion

<400> SEQUENCE: 8

Met Val Asn Val Lys Pro Val Thr Leu Tyr Asp Val Ala Glu Tyr Ala
1               5                   10                  15

Gly Val Ser Tyr Gln Thr Val Ser Arg Val Val Asn Gln Ala Ser His
            20                  25                  30

Val Ser Ala Lys Thr Arg Glu Lys Val Glu Ala Ala Met Ala Glu Leu
        35                  40                  45

Asn Tyr Ile Pro Asn Arg Val Ala Gln Gln Leu Ala Gly Lys Gln Ser
    50                  55                  60

Leu Leu Ile Gly Val Ala Thr Ser Ser Leu Ala Leu His Ala Pro Ser
65                  70                  75                  80

Gln Ile Val Ala Ala Ile Lys Ser Arg Ala Asp Gln Leu Gly Ala Ser
                85                  90                  95

Val Val Val Ser Met Val Glu Arg Ser Gly Val Glu Ala Cys Lys Ala
            100                 105                 110

Ala Val His Asn Leu Leu Ala Gln Arg Val Ser Gly Leu Ile Ile Asn
        115                 120                 125

Tyr Pro Leu Asp Asp Gln Asp Ala Ile Ala Val Glu Ala Ala Cys Thr
    130                 135                 140

Asn Val Pro Ala Leu Phe Leu Asp Val Ser Asp Gln Thr Pro Ile Asn
145                 150                 155                 160

Ser Ile Ile Phe Ser His Glu Asp Gly Thr Arg Leu Gly Val Glu His
                165                 170                 175

Leu Val Ala Leu Gly His Gln Gln Ile Ala Leu Leu Ala Gly Pro Leu
            180                 185                 190

Ser Ser Val Ser Ala Arg Leu Arg Leu Ala Gly Trp His Lys Tyr Leu
        195                 200                 205

Thr Arg Asn Gln Ile Gln Pro Ile Ala Glu Arg Glu Gly Asp Trp Ser
    210                 215                 220

Ala Met Ser Gly Phe Gln Gln Thr Met Gln Met Leu Asn Glu Gly Ile
225                 230                 235                 240

Val Pro Thr Ala Met Leu Val Ala Asn Asp Gln Met Ala Leu Gly Ala
                245                 250                 255
```

```
Met Arg Ala Ile Thr Glu Ser Gly Leu Arg Val Gly Ala Asp Ile Ser
                260                 265                 270

Val Val Gly Tyr Asp Asp Thr Glu Asp Ser Ser Cys Tyr Ile Pro Pro
            275                 280                 285

Leu Thr Thr Ile Lys Gln Asp Phe Arg Leu Leu Gly Gln Thr Ser Val
        290                 295                 300

Asp Arg Leu Leu Gln Leu Ser Gln Gly Gln Ala Val Lys Gly Asn Gln
305                 310                 315                 320

Leu Leu Pro Val Ser Leu Val Lys Arg Lys Thr Thr Leu Ala Pro Asn
                325                 330                 335

Thr Gln Thr Ala Ser Pro Arg Ala Leu Ala Asp Ser Leu Met Gln Leu
            340                 345                 350

Ala Arg Gln Val Ser Arg Ala Pro Pro Thr Asp Val Ser Leu Gly Asp
        355                 360                 365

Glu Leu His Leu Asp Gly Glu Asp Val Ala Met Ala His Ala Asp Ala
370                 375                 380

Leu Asp Asp Phe Asp Leu Asp Met Leu Gly Asp Gly Asp Ser Pro Gly
385                 390                 395                 400

Pro Gly Phe Thr Pro His Asp Ser Ala Pro Tyr Gly Ala Leu Asp Met
                405                 410                 415

Ala Asp Phe Glu Phe Glu Gln Met Phe Thr Asp Ala Leu Gly Ile Asp
            420                 425                 430

Glu Tyr Gly Gly
        435

<210> SEQ ID NO 9
<211> LENGTH: 336
<212> TYPE: PRT
<213> ORGANISM: Artificial Sequence
<220> FEATURE:
<223> OTHER INFORMATION: amino acid sequence of tetracycline-controlled
      transactivator (tTA)

<400> SEQUENCE: 9

Met Met Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
                20                  25                  30

Gln Lys Leu Gly Val Glu Gln Pro Thr Leu Tyr Trp His Val Lys Asn
            35                  40                  45

Lys Arg Ala Leu Leu Asp Ala Leu Ala Ile Glu Met Leu Asp Arg His
        50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175
```

Leu Phe Asp His Gln Gly Ala Glu Pro Ala Phe Leu Phe Gly Leu Glu
                180                 185                 190

Leu Ile Ile Cys Gly Leu Glu Lys Gln Leu Lys Cys Glu Ser Gly Ser
            195                 200                 205

Ala Tyr Ser Arg Ala Arg Thr Lys Asn Asn Tyr Gly Ser Thr Ile Glu
210                 215                 220

Gly Leu Leu Asp Leu Pro Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335

<210> SEQ ID NO 10
<211> LENGTH: 232
<212> TYPE: PRT
<213> ORGANISM: Artificial Sequence
<220> FEATURE:
<223> OTHER INFORMATION: amino acid sequence of GAL4/VP16 fusion protein

<400> SEQUENCE: 10

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Trp Ala Pro Pro Thr Asp Val
145                 150                 155                 160

Ser Leu Gly Asp Glu Leu His Leu Asp Gly Glu Asp Val Ala Met Ala
                165                 170                 175

His Ala Asp Ala Leu Asp Asp Phe Asp Leu Asp Met Leu Gly Asp Gly
            180                 185                 190

Asp Ser Pro Gly Pro Gly Phe Thr Pro His Asp Ser Ala Pro Tyr Gly
        195                 200                 205

```
Ala Leu Asp Met Ala Asp Phe Glu Phe Glu Gln Met Phe Thr Asp Ala
    210                 215                 220

Leu Gly Ile Asp Glu Tyr Gly Gly
225                 230

<210> SEQ ID NO 11
<211> LENGTH: 382
<212> TYPE: PRT
<213> ORGANISM: Artificial Sequence
<220> FEATURE:
<223> OTHER INFORMATION: amino acid sequence of LexA/QF fusion protein

<400> SEQUENCE: 11

Met Pro Pro Lys Lys Arg Lys Val Glu Asp Pro Met Lys Ala Leu
1               5                   10                  15

Thr Ala Arg Gln Gln Glu Val Phe Asp Leu Ile Arg Asp His Ile Ser
            20                  25                  30

Gln Thr Gly Met Pro Pro Thr Arg Ala Glu Ile Ala Gln Arg Leu Gly
        35                  40                  45

Phe Arg Ser Pro Asn Ala Ala Glu Glu His Leu Lys Ala Leu Ala Arg
    50                  55                  60

Lys Gly Val Ile Glu Ile Val Ser Gly Ala Ser Arg Gly Ile Arg Leu
65                  70                  75                  80

Leu Gln Glu Glu Glu Gly Leu Pro Leu Val Gly Arg Val Ala Ala
                85                  90                  95

Gly Glu Pro Leu Leu Ala Gln Gln His Ile Glu Gly His Tyr Gln Val
            100                 105                 110

Asp Pro Ser Leu Phe Lys Pro Asn Ala Asp Phe Leu Leu Arg Val Ser
        115                 120                 125

Gly Met Ser Met Lys Asp Ile Gly Ile Met Asp Gly Asp Leu Leu Ala
    130                 135                 140

Val His Lys Thr Gln Asp Val Arg Asn Gly Gln Val Val Val Ala Arg
145                 150                 155                 160

Ile Asp Asp Glu Val Thr Val Lys Arg Leu Lys Lys Gln Gly Asn Lys
                165                 170                 175

Val Glu Leu Leu Pro Glu Asn Ser Glu Phe Lys Pro Ile Val Val Asp
            180                 185                 190

Leu Arg Gln Gln Ser Phe Thr Ile Glu Gly Leu Ala Val Gly Val Ile
        195                 200                 205

Arg Asn Gly Asp Trp Leu Gly Arg Gln Leu Glu Leu Pro Pro Thr Ala
    210                 215                 220

Thr Ala Thr Ala Ser Ile Met Pro His Val Met Glu Gln Pro Leu Ser
225                 230                 235                 240

Thr Ser Ile Asn Pro Val Asn Asp Arg Phe Asn Gly Ile Pro Asn Pro
                245                 250                 255

Thr Pro Tyr Asn Ser Asp Ala Ala Leu Asp Ala Ile Thr Gln Thr Asn
            260                 265                 270

Asp Tyr Gly Ser Val Asn Thr His Gly Ile Leu Ser Thr Tyr Pro Pro
        275                 280                 285

Pro Ala Thr His Leu Asn Glu Ala Ser Val Ala Leu Ala Pro Gly Gly
    290                 295                 300

Ala Pro Pro Arg Pro Pro Pro Tyr Val Asp Ser Thr Thr Asn His
305                 310                 315                 320

Pro Pro Tyr His Ser Asn Leu Val Pro Met Ala Asn Phe Gly Tyr Ser
                325                 330                 335
```

Thr Val Asp Tyr Asp Ala Met Val Asp Asp Leu Ala Ser Ile Glu Tyr
            340                 345                 350

Thr Asp Ala Val Asp Val Asp Pro Gln Phe Met Thr Asn Leu Gly Phe
        355                 360                 365

Val Pro Gly Cys Asn Phe Ser Asp Ile Asn Thr Tyr Glu Gln
    370                 375                 380

<210> SEQ ID NO 12
<211> LENGTH: 8
<212> TYPE: DNA
<213> ORGANISM: Artificial Sequence
<220> FEATURE:
<223> OTHER INFORMATION: DNA binding sequence of Brain-1

<400> SEQUENCE: 12 atttgcat                                                            8

<210> SEQ ID NO 13
<211> LENGTH: 500
<212> TYPE: PRT
<213> ORGANISM: Homo sapiens

<400> SEQUENCE: 13

Met Ala Thr Ala Ala Ser Asn Pro Tyr Leu Pro Gly Asn Ser Leu Leu
1               5                   10                  15

Ala Ala Gly Ser Ile Val His Ser Asp Ala Ala Gly Ala Gly Gly Gly
            20                  25                  30

Gly Gly Gly Gly Gly Gly Gly Gly Gly Gly Ala Gly Gly Gly Gly
        35                  40                  45

Gly Gly Met Gln Pro Gly Ser Ala Ala Val Thr Ser Gly Ala Tyr Arg
    50                  55                  60

Gly Asp Pro Ser Ser Val Lys Met Val Gln Ser Asp Phe Met Gln Gly
65                  70                  75                  80

Ala Met Ala Ala Ser Asn Gly Gly His Met Leu Ser His Ala His Gln
                85                  90                  95

Trp Val Thr Ala Leu Pro His Ala Ala Ala Ala Ala Ala Ala Ala
            100                 105                 110

Ala Ala Ala Val Glu Ala Ser Ser Pro Trp Ser Gly Ser Ala Val Gly
        115                 120                 125

Met Ala Gly Ser Pro Gln Gln Pro Gln Pro Pro Pro Pro Pro
    130                 135                 140

Gln Gly Pro Asp Val Lys Gly Gly Ala Gly Arg Asp Asp Leu His Ala
145                 150                 155                 160

Gly Thr Ala Leu His His Arg Gly Pro Pro His Leu Gly Pro Pro Pro
                165                 170                 175

Pro Pro Pro His Gln Gly His Pro Gly Gly Trp Gly Ala Ala Ala Ala
            180                 185                 190

Ala Ala Ala Ala Ala Ala Ala Ala Ala Ala His Leu Pro Ser
        195                 200                 205

Met Ala Gly Gly Gln Gln Pro Pro Gln Ser Leu Leu Tyr Ser Gln
    210                 215                 220

Pro Gly Gly Phe Thr Val Asn Gly Met Leu Ser Ala Pro Pro Gly Pro
225                 230                 235                 240

Gly Gly Gly Gly Gly Gly Ala Gly Gly Gly Ala Gln Ser Leu Val His
                245                 250                 255

Pro Gly Leu Val Arg Gly Asp Thr Pro Glu Leu Ala Glu His His His

```
                      260                 265                 270
His His His His His Ala His Pro His Pro Pro His Pro His His Ala
                275                 280                 285
Gln Gly Pro Pro His His Gly Gly Gly Gly Gly Ala Gly Pro Gly
            290                 295                 300
Leu Asn Ser His Asp Pro His Ser Asp Glu Asp Thr Pro Thr Ser Asp
305                 310                 315                 320
Asp Leu Glu Gln Phe Ala Lys Gln Phe Lys Gln Arg Arg Ile Lys Leu
                325                 330                 335
Gly Phe Thr Gln Ala Asp Val Gly Leu Ala Leu Gly Thr Leu Tyr Gly
                340                 345                 350
Asn Val Phe Ser Gln Thr Thr Ile Cys Arg Phe Glu Ala Leu Gln Leu
                355                 360                 365
Ser Phe Lys Asn Met Cys Lys Leu Lys Pro Leu Leu Asn Lys Trp Leu
                370                 375                 380
Glu Glu Ala Asp Ser Ser Thr Gly Ser Pro Thr Ser Ile Asp Lys Ile
385                 390                 395                 400
Ala Ala Gln Gly Arg Lys Arg Lys Arg Thr Ser Ile Glu Val Ser
                405                 410                 415
Val Lys Gly Ala Leu Glu Ser His Phe Leu Lys Cys Pro Lys Pro Ser
                420                 425                 430
Ala Gln Glu Ile Thr Asn Leu Ala Asp Ser Leu Gln Leu Glu Lys Glu
                435                 440                 445
Val Val Arg Val Trp Phe Cys Asn Arg Arg Gln Lys Glu Lys Arg Met
450                 455                 460
Thr Pro Pro Gly Ile Gln Gln Gln Thr Pro Asp Asp Val Tyr Ser Gln
465                 470                 475                 480
Val Gly Thr Val Ser Ala Asp Thr Pro Pro His His Gly Leu Gln
                485                 490                 495
Thr Ser Val Gln
            500

<210> SEQ ID NO 14
<211> LENGTH: 443
<212> TYPE: PRT
<213> ORGANISM: Homo sapiens

<400> SEQUENCE: 14

Met Ala Thr Ala Ala Ser Asn His Tyr Ser Leu Leu Thr Ser Ser Ala
1               5                   10                  15
Ser Ile Val His Ala Glu Pro Pro Gly Gly Met Gln Gln Gly Ala Gly
                20                  25                  30
Gly Tyr Arg Glu Ala Gln Ser Leu Val Gln Gly Asp Tyr Gly Ala Leu
                35                  40                  45
Gln Ser Asn Gly His Pro Leu Ser His Ala His Gln Trp Ile Thr Ala
                50                  55                  60
Leu Ser His Gly Gly Gly Gly Gly Gly Gly Gly Gly Gly Gly Gly Gly
65                  70                  75                  80
Gly Gly Gly Gly Gly Gly Gly Asp Gly Ser Pro Trp Ser Thr Ser
                85                  90                  95
Pro Leu Gly Gln Pro Asp Ile Lys Pro Ser Val Val Gln Gln Gly
                100                 105                 110
Gly Arg Gly Asp Glu Leu His Gly Pro Gly Ala Leu Gln Gln Gln His
                115                 120                 125
```

-continued

```
Gln Gln Gln Gln Gln Gln Gln Gln Gln Gln Gln Gln Gln Gln
    130                 135                 140
Gln Gln Gln Gln Gln Arg Pro His Leu Val His His Ala Ala Asn
145                 150                 155                 160
His His Pro Gly Pro Gly Ala Trp Arg Ser Ala Ala Ala Ala His
                165                 170                 175
Leu Pro Pro Ser Met Gly Ala Ser Asn Gly Gly Leu Leu Tyr Ser Gln
            180                 185                 190
Pro Ser Phe Thr Val Asn Gly Met Leu Gly Ala Gly Gln Pro Ala
        195                 200                 205
Gly Leu His His His Gly Leu Arg Asp Ala His Asp Glu Pro His His
    210                 215                 220
Ala Asp His His Pro His Pro His Ser His Pro His Gln Gln Pro Pro
225                 230                 235                 240
Pro Pro Pro Pro Gln Gly Pro Pro Gly His Pro Gly Ala His His
                245                 250                 255
Asp Pro His Ser Asp Glu Asp Thr Pro Thr Ser Asp Asp Leu Glu Gln
            260                 265                 270
Phe Ala Lys Gln Phe Lys Gln Arg Arg Ile Lys Leu Gly Phe Thr Gln
    275                 280                 285
Ala Asp Val Gly Leu Ala Leu Gly Thr Leu Tyr Gly Asn Val Phe Ser
290                 295                 300
Gln Thr Thr Ile Cys Arg Phe Glu Ala Leu Gln Leu Ser Phe Lys Asn
305                 310                 315                 320
Met Cys Lys Leu Lys Pro Leu Leu Asn Lys Trp Leu Glu Glu Ala Asp
                325                 330                 335
Ser Ser Ser Gly Ser Pro Thr Ser Ile Asp Lys Ile Ala Ala Gln Gly
            340                 345                 350
Arg Lys Arg Lys Lys Arg Thr Ser Ile Glu Val Ser Val Lys Gly Ala
    355                 360                 365
Leu Glu Ser His Phe Leu Lys Cys Pro Lys Pro Ser Ala Gln Glu Ile
370                 375                 380
Thr Ser Leu Ala Asp Ser Leu Gln Leu Glu Lys Glu Val Val Arg Val
385                 390                 395                 400
Trp Phe Cys Asn Arg Arg Gln Lys Glu Lys Arg Met Thr Pro Pro Gly
                405                 410                 415
Gly Thr Leu Pro Gly Ala Glu Asp Val Tyr Gly Ser Arg Asp Thr
            420                 425                 430
Pro Pro His His Gly Val Gln Thr Pro Val Gln
    435                 440
```

<210> SEQ ID NO 15
<211> LENGTH: 15
<212> TYPE: DNA
<213> ORGANISM: Artificial Sequence
<220> FEATURE:
<223> OTHER INFORMATION: DNA binding site of NFIC
<220> FEATURE:
<221> NAME/KEY: misc_feature
<222> LOCATION: (6)..(10)
<223> OTHER INFORMATION: n is a, c, g, or t

<400> SEQUENCE: 15
ttggcnnnnn gccaa                                                      15

<210> SEQ ID NO 16
<211> LENGTH: 508

<212> TYPE: PRT
<213> ORGANISM: Homo sapiens

<400> SEQUENCE: 16

```
Met Tyr Ser Ser Pro Leu Cys Leu Thr Gln Asp Glu Phe His Pro Phe
1               5                   10                  15

Ile Glu Ala Leu Leu Pro His Val Arg Ala Phe Ala Tyr Thr Trp Phe
            20                  25                  30

Asn Leu Gln Ala Arg Lys Arg Lys Tyr Phe Lys Lys His Glu Lys Arg
        35                  40                  45

Met Ser Lys Asp Glu Glu Arg Ala Val Lys Asp Glu Leu Leu Gly Glu
    50                  55                  60

Lys Pro Glu Val Lys Gln Lys Trp Ala Ser Arg Leu Leu Ala Lys Leu
65                  70                  75                  80

Arg Lys Asp Ile Arg Pro Glu Cys Arg Glu Asp Phe Val Leu Ser Ile
                85                  90                  95

Thr Gly Lys Lys Ala Pro Gly Cys Val Leu Ser Asn Pro Asp Gln Lys
            100                 105                 110

Gly Lys Met Arg Arg Ile Asp Cys Leu Arg Gln Ala Asp Lys Val Trp
        115                 120                 125

Arg Leu Asp Leu Val Met Val Ile Leu Phe Lys Gly Ile Pro Leu Glu
130                 135                 140

Ser Thr Asp Gly Glu Arg Leu Val Lys Ala Ala Gln Cys Gly His Pro
145                 150                 155                 160

Val Leu Cys Val Gln Pro His His Ile Gly Val Ala Val Lys Glu Leu
                165                 170                 175

Asp Leu Tyr Leu Ala Tyr Phe Val Arg Glu Arg Asp Ala Glu Gln Ser
            180                 185                 190

Gly Ser Pro Arg Thr Gly Met Gly Ser Asp Gln Glu Ser Lys Pro
        195                 200                 205

Ile Thr Leu Asp Thr Thr Asp Phe Gln Glu Ser Phe Val Thr Ser Gly
    210                 215                 220

Val Phe Ser Val Thr Glu Leu Ile Gln Val Ser Arg Thr Pro Val Val
225                 230                 235                 240

Thr Gly Thr Gly Pro Asn Phe Ser Leu Gly Glu Leu Gln Gly His Leu
                245                 250                 255

Ala Tyr Asp Leu Asn Pro Ala Ser Thr Gly Leu Arg Arg Thr Leu Pro
            260                 265                 270

Ser Thr Ser Ser Ser Gly Ser Lys Arg His Lys Ser Gly Ser Met Glu
        275                 280                 285

Glu Asp Val Asp Thr Ser Pro Gly Gly Asp Tyr Tyr Thr Ser Pro Ser
    290                 295                 300

Ser Pro Thr Ser Ser Ser Arg Asn Trp Thr Glu Asp Met Glu Gly Gly
305                 310                 315                 320

Ile Ser Ser Pro Val Lys Lys Thr Glu Met Asp Lys Ser Pro Phe Asn
                325                 330                 335

Ser Pro Ser Pro Gln Asp Ser Pro Arg Leu Ser Ser Phe Thr Gln His
            340                 345                 350

His Arg Pro Val Ile Ala Val His Ser Gly Ile Ala Arg Ser Pro His
        355                 360                 365

Pro Ser Ser Ala Leu His Phe Pro Thr Thr Ser Ile Leu Pro Gln Thr
    370                 375                 380

Ala Ser Thr Tyr Phe Pro His Thr Ala Ile Arg Tyr Pro Pro His Leu
385                 390                 395                 400
```

```
Asn Pro Gln Asp Pro Leu Lys Asp Leu Val Ser Leu Ala Cys Asp Pro
                405                 410                 415

Ala Ser Gln Gln Pro Gly Pro Leu Asn Gly Ser Gly Gln Leu Lys Met
            420                 425                 430

Pro Ser His Cys Leu Ser Ala Gln Met Leu Ala Pro Pro Pro Pro Gly
        435                 440                 445

Leu Pro Arg Leu Ala Leu Pro Pro Ala Thr Lys Pro Ala Thr Thr Ser
450                 455                 460

Glu Gly Gly Ala Thr Ser Pro Thr Ser Pro Ser Tyr Ser Pro Pro Asp
465                 470                 475                 480

Thr Ser Pro Ala Asn Arg Ser Phe Val Gly Leu Gly Pro Arg Asp Pro
                485                 490                 495

Ala Gly Ile Tyr Gln Ala Gln Ser Trp Tyr Leu Gly
            500                 505

<210> SEQ ID NO 17
<211> LENGTH: 15
<212> TYPE: DNA
<213> ORGANISM: Artificial Sequence
<220> FEATURE:
<223> OTHER INFORMATION: DNA binding site of NFIC
<220> FEATURE:
<221> NAME/KEY: misc_feature
<222> LOCATION: (6)..(10)
<223> OTHER INFORMATION: n is a, c, g, or t

<400> SEQUENCE: 17
ttggcnnnnn gccaa                                                         15

<210> SEQ ID NO 18
<211> LENGTH: 502
<212> TYPE: PRT
<213> ORGANISM: Homo sapiens

<400> SEQUENCE: 18

Met Tyr Ser Pro Tyr Cys Leu Thr Gln Asp Glu Phe His Pro Phe Ile
1               5                   10                  15

Glu Ala Leu Leu Pro His Val Arg Ala Phe Ser Tyr Thr Trp Phe Asn
            20                  25                  30

Leu Gln Ala Arg Lys Arg Lys Tyr Phe Lys Lys His Glu Lys Arg Met
        35                  40                  45

Ser Lys Asp Glu Glu Arg Ala Val Lys Asp Glu Leu Leu Gly Glu Lys
    50                  55                  60

Pro Glu Ile Lys Gln Lys Trp Ala Ser Arg Leu Leu Ala Lys Leu Arg
65                  70                  75                  80

Lys Asp Ile Arg Pro Glu Phe Arg Glu Asp Phe Val Leu Thr Ile Thr
                85                  90                  95

Gly Lys Lys Pro Pro Cys Cys Val Leu Ser Asn Pro Asp Gln Lys Gly
            100                 105                 110

Lys Ile Arg Arg Ile Asp Cys Leu Arg Gln Ala Asp Lys Val Trp Arg
        115                 120                 125

Leu Asp Leu Val Met Val Ile Leu Phe Lys Gly Ile Pro Leu Glu Ser
    130                 135                 140

Thr Asp Gly Glu Arg Leu Tyr Lys Ser Pro Gln Cys Ser Asn Pro Gly
145                 150                 155                 160

Leu Cys Val Gln Pro His His Ile Gly Val Thr Ile Lys Glu Leu Asp
                165                 170                 175
```

```
Leu Tyr Leu Ala Tyr Phe Val His Thr Pro Glu Ser Gly Gln Ser Asp
            180                 185                 190

Ser Ser Asn Gln Gln Gly Asp Ala Asp Ile Lys Pro Leu Pro Asn Gly
            195                 200                 205

His Leu Ser Phe Gln Asp Cys Phe Val Thr Ser Gly Val Trp Asn Val
            210                 215                 220

Thr Glu Leu Val Arg Val Ser Gln Thr Pro Val Ala Thr Ala Ser Gly
225                 230                 235                 240

Pro Asn Phe Ser Leu Ala Asp Leu Glu Ser Pro Ser Tyr Tyr Asn Ile
                245                 250                 255

Asn Gln Val Thr Leu Gly Arg Arg Ser Ile Thr Ser Pro Pro Ser Thr
            260                 265                 270

Ser Thr Thr Lys Arg Pro Lys Ser Ile Asp Asp Ser Glu Met Glu Ser
            275                 280                 285

Pro Val Asp Asp Val Phe Tyr Pro Gly Thr Gly Arg Ser Pro Ala Ala
            290                 295                 300

Gly Ser Ser Gln Ser Ser Gly Trp Pro Asn Asp Val Asp Ala Gly Pro
305                 310                 315                 320

Ala Ser Leu Lys Lys Ser Gly Lys Leu Asp Phe Cys Ser Ala Leu Ser
                325                 330                 335

Ser Gln Gly Ser Ser Pro Arg Met Ala Phe Thr His His Pro Leu Pro
            340                 345                 350

Val Leu Ala Gly Val Arg Pro Gly Ser Pro Arg Ala Thr Ala Ser Ala
            355                 360                 365

Leu His Phe Pro Ser Thr Ser Ile Ile Gln Gln Ser Ser Pro Tyr Phe
            370                 375                 380

Thr His Pro Thr Ile Arg Tyr His His His Gly Gln Asp Ser Leu
385                 390                 395                 400

Lys Glu Phe Val Gln Phe Val Cys Ser Asp Gly Ser Gly Gln Ala Thr
                405                 410                 415

Gly Gln Pro Asn Gly Ser Gly Gln Gly Lys Val Pro Gly Ser Phe Leu
            420                 425                 430

Leu Pro Pro Pro Pro Val Ala Arg Pro Val Pro Leu Pro Met Pro
            435                 440                 445

Asp Ser Lys Ser Thr Ser Thr Ala Pro Asp Gly Ala Ala Leu Thr Pro
450                 455                 460

Pro Ser Pro Ser Phe Ala Thr Thr Gly Ala Ser Ala Asn Arg Phe
465                 470                 475                 480

Val Ser Ile Gly Pro Arg Asp Gly Asn Phe Leu Asn Ile Pro Gln Gln
                485                 490                 495

Ser Gln Ser Trp Phe Leu
            500

<210> SEQ ID NO 19
<211> LENGTH: 6
<212> TYPE: DNA
<213> ORGANISM: Artificial Sequence
<220> FEATURE:
<223> OTHER INFORMATION: DNA binding site of MyoD
<220> FEATURE:
<221> NAME/KEY: misc_feature
<222> LOCATION: (3)..(4)
<223> OTHER INFORMATION: n is a, c, g, or t

<400> SEQUENCE: 19 canntg                                                                      6
```

-continued

```
<210> SEQ ID NO 20
<211> LENGTH: 320
<212> TYPE: PRT
<213> ORGANISM: Homo sapiens

<400> SEQUENCE: 20

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Ala Phe Tyr Ala Pro Gly Pro Leu Pro Pro Gly Arg Gly Gly Glu His
            180                 185                 190

Tyr Ser Gly Asp Ser Asp Ala Ser Ser Pro Arg Ser Asn Cys Ser Asp
        195                 200                 205

Gly Met Met Asp Tyr Ser Gly Pro Pro Ser Gly Ala Arg Arg Arg Asn
210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
                245                 250                 255

Glu Arg Ile Ser Thr Glu Ser Pro Ala Ala Pro Ala Leu Leu Leu Ala
            260                 265                 270

Asp Val Pro Ser Glu Ser Pro Arg Arg Gln Glu Ala Ala Ala Pro
        275                 280                 285

Ser Glu Gly Glu Ser Ser Gly Asp Pro Thr Gln Ser Pro Asp Ala Ala
    290                 295                 300

Pro Gln Cys Pro Ala Gly Ala Asn Pro Asn Pro Ile Tyr Gln Val Leu
305                 310                 315                 320

<210> SEQ ID NO 21
<211> LENGTH: 10
<212> TYPE: DNA
<213> ORGANISM: Artificial Sequence
<220> FEATURE:
<223> OTHER INFORMATION: DNA binding site of MEF2A

<400> SEQUENCE: 21 ytawwwwtar                                                    10
```

<210> SEQ ID NO 22
<211> LENGTH: 506
<212> TYPE: PRT
<213> ORGANISM: Homo sapiens

<400> SEQUENCE: 22

```
Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Ser Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Lys Glu His Arg Gly Cys
                85                  90                  95

Asp Ser Pro Asp Pro Asp Thr Ser Tyr Val Leu Thr Pro His Thr Glu
            100                 105                 110

Glu Lys Tyr Lys Lys Ile Asn Glu Glu Phe Asp Asn Met Met Arg Asn
        115                 120                 125

His Lys Ile Ala Pro Gly Leu Pro Pro Gln Asn Phe Ser Met Ser Val
    130                 135                 140

Thr Val Pro Val Thr Ser Pro Asn Ala Leu Ser Tyr Thr Asn Pro Gly
145                 150                 155                 160

Ser Ser Leu Val Ser Pro Ser Leu Ala Ala Ser Ser Thr Leu Thr Asp
                165                 170                 175

Ser Ser Met Leu Ser Pro Pro Gln Thr Thr Leu His Arg Asn Val Ser
            180                 185                 190

Pro Gly Ala Pro Gln Arg Pro Pro Ser Thr Gly Asn Ala Gly Gly Met
        195                 200                 205

Leu Ser Thr Thr Asp Leu Thr Val Pro Asn Gly Ala Gly Ser Ser Pro
    210                 215                 220

Val Gly Asn Gly Phe Val Asn Ser Arg Ala Ser Pro Asn Leu Ile Gly
225                 230                 235                 240

Ala Thr Gly Ala Asn Ser Leu Gly Lys Val Met Pro Thr Lys Ser Pro
                245                 250                 255

Pro Pro Pro Gly Gly Gly Asn Leu Gly Met Asn Ser Arg Lys Pro Asp
            260                 265                 270

Leu Arg Val Val Ile Pro Pro Ser Ser Lys Gly Met Met Pro Pro Leu
        275                 280                 285

Ser Glu Glu Glu Glu Leu Glu Leu Asn Thr Gln Arg Ile Ser Ser Ser
    290                 295                 300

Gln Ala Thr Gln Pro Leu Ala Thr Pro Val Val Ser Val Thr Thr Pro
305                 310                 315                 320

Ser Leu Pro Pro Gln Gly Leu Val Tyr Ser Ala Met Pro Thr Ala Tyr
                325                 330                 335

Asn Thr Asp Tyr Ser Leu Thr Ser Ala Asp Leu Ser Ala Leu Gln Gly
            340                 345                 350

Phe Asn Ser Pro Gly Met Leu Ser Leu Gly Gln Val Ser Ala Trp Gln
        355                 360                 365

Gln His His Leu Gly Gln Ala Ala Leu Ser Ser Leu Val Ala Gly Gly
```

```
              370                 375                 380
Gln Leu Ser Gln Gly Ser Asn Leu Ser Ile Asn Thr Asn Gln Asn Ile
385                 390                 395                 400

Ser Ile Lys Ser Glu Pro Ile Ser Pro Pro Arg Asp Arg Met Thr Pro
                405                 410                 415

Ser Gly Phe Gln Gln Gln Gln Gln Gln Gln Gln Gln Gln Gln Pro Pro
                420                 425                 430

Pro Pro Pro Gln Pro Gln Pro Gln Pro Gln Pro Gln Pro Arg Gln
            435                 440                 445

Glu Met Gly Arg Ser Pro Val Asp Ser Leu Ser Ser Ser Ser Ser Ser
            450                 455                 460

Tyr Asp Gly Ser Asp Arg Glu Asp Pro Arg Gly Asp Phe His Ser Pro
465                 470                 475                 480

Ile Val Leu Gly Arg Pro Pro Asn Thr Glu Asp Arg Glu Ser Pro Ser
                485                 490                 495

Val Lys Arg Met Arg Met Asp Ala Trp Val
                500                 505
```

<210> SEQ ID NO 23
<211> LENGTH: 7
<212> TYPE: DNA
<213> ORGANISM: Artificial Sequence
<220> FEATURE:
<223> OTHER INFORMATION: DNA-binding site of KLF3

<400> SEQUENCE: 23 cmcaccc                                                                7

<210> SEQ ID NO 24
<211> LENGTH: 345
<212> TYPE: PRT
<213> ORGANISM: Homo sapiens

<400> SEQUENCE: 24

```
Met Leu Met Phe Asp Pro Val Pro Val Lys Gln Glu Ala Met Asp Pro
1               5                   10                  15

Val Ser Val Ser Tyr Pro Ser Asn Tyr Met Glu Ser Met Lys Pro Asn
                20                  25                  30

Lys Tyr Gly Val Ile Tyr Ser Thr Pro Leu Pro Glu Lys Phe Phe Gln
            35                  40                  45

Thr Pro Glu Gly Leu Ser His Gly Ile Gln Met Glu Pro Val Asp Leu
        50                  55                  60

Thr Val Asn Lys Arg Ser Ser Pro Ser Ala Gly Asn Ser Pro Ser
65                  70                  75                  80

Ser Leu Lys Phe Pro Ser Ser His Arg Arg Ala Ser Pro Gly Leu Ser
                85                  90                  95

Met Pro Ser Ser Pro Pro Ile Lys Lys Tyr Ser Pro Pro Ser Pro
                100                 105                 110

Gly Val Gln Pro Phe Gly Val Pro Leu Ser Met Pro Pro Val Met Ala
            115                 120                 125

Ala Ala Leu Ser Arg His Gly Ile Arg Ser Pro Gly Ile Leu Pro Val
        130                 135                 140

Ile Gln Pro Val Val Val Gln Pro Val Pro Phe Met Tyr Thr Ser His
145                 150                 155                 160

Leu Gln Gln Pro Leu Met Val Ser Leu Ser Glu Glu Met Glu Asn Ser
                165                 170                 175
```

```
Ser Ser Ser Met Gln Val Pro Val Ile Glu Ser Tyr Glu Lys Pro Ile
            180                 185                 190

Ser Gln Lys Lys Ile Lys Ile Glu Pro Gly Ile Glu Pro Gln Arg Thr
        195                 200                 205

Asp Tyr Tyr Pro Glu Glu Met Ser Pro Pro Leu Met Asn Ser Val Ser
    210                 215                 220

Pro Pro Gln Ala Leu Leu Gln Glu Asn His Pro Ser Val Ile Val Gln
225                 230                 235                 240

Pro Gly Lys Arg Pro Leu Pro Val Glu Ser Pro Asp Thr Gln Arg Lys
                245                 250                 255

Arg Arg Ile His Arg Cys Asp Tyr Asp Gly Cys Asn Lys Val Tyr Thr
                260                 265                 270

Lys Ser Ser His Leu Lys Ala His Arg Arg Thr His Thr Gly Glu Lys
    275                 280                 285

Pro Tyr Lys Cys Thr Trp Glu Gly Cys Thr Trp Lys Phe Ala Arg Ser
    290                 295                 300

Asp Glu Leu Thr Arg His Phe Arg Lys His Thr Gly Ile Lys Pro Phe
305                 310                 315                 320

Gln Cys Pro Asp Cys Asp Arg Ser Phe Ser Arg Ser Asp His Leu Ala
                325                 330                 335

Leu His Arg Lys Arg His Met Leu Val
                340                 345

<210> SEQ ID NO 25
<211> LENGTH: 1437
<212> TYPE: PRT
<213> ORGANISM: Artificial Sequence
<220> FEATURE:
<223> OTHER INFORMATION: amino acid sequence of dCas9/VP64

<400> SEQUENCE: 25

Met Lys Lys Lys Arg Lys Val Glu Ala Ser Asp Lys Lys Tyr Ser Ile
1               5                   10                  15

Gly Leu Ala Ile Gly Thr Asn Ser Val Gly Trp Ala Val Ile Thr Asp
            20                  25                  30

Glu Tyr Lys Val Pro Ser Lys Lys Phe Lys Val Leu Gly Asn Thr Asp
        35                  40                  45

Arg His Ser Ile Lys Lys Asn Leu Ile Gly Ala Leu Leu Phe Asp Ser
    50                  55                  60

Gly Glu Thr Ala Glu Ala Thr Arg Leu Lys Arg Thr Ala Arg Arg Arg
65                  70                  75                  80

Tyr Thr Arg Arg Lys Asn Arg Ile Cys Tyr Leu Gln Glu Ile Phe Ser
                85                  90                  95

Asn Glu Met Ala Lys Val Asp Asp Ser Phe Phe His Arg Leu Glu Glu
            100                 105                 110

Ser Phe Leu Val Glu Glu Asp Lys Lys His Glu Arg His Pro Ile Phe
        115                 120                 125

Gly Asn Ile Val Asp Glu Val Ala Tyr His Glu Lys Tyr Pro Thr Ile
    130                 135                 140

Tyr His Leu Arg Lys Lys Leu Val Asp Ser Thr Asp Lys Ala Asp Leu
145                 150                 155                 160

Arg Leu Ile Tyr Leu Ala Leu Ala His Met Ile Lys Phe Arg Gly His
                165                 170                 175

Phe Leu Ile Glu Gly Asp Leu Asn Pro Asp Asn Ser Asp Val Asp Lys
            180                 185                 190
```

```
Leu Phe Ile Gln Leu Val Gln Thr Tyr Asn Gln Leu Phe Glu Glu Asn
            195                 200                 205

Pro Ile Asn Ala Ser Gly Val Asp Ala Lys Ala Ile Leu Ser Ala Arg
        210                 215                 220

Leu Ser Lys Ser Arg Arg Leu Glu Asn Leu Ile Ala Gln Leu Pro Gly
225                 230                 235                 240

Glu Lys Lys Asn Gly Leu Phe Gly Asn Leu Ile Ala Leu Ser Leu Gly
                245                 250                 255

Leu Thr Pro Asn Phe Lys Ser Asn Phe Asp Leu Ala Glu Asp Ala Lys
            260                 265                 270

Leu Gln Leu Ser Lys Asp Thr Tyr Asp Asp Leu Asp Asn Leu Leu
        275                 280                 285

Ala Gln Ile Gly Asp Gln Tyr Ala Asp Leu Phe Leu Ala Ala Lys Asn
        290                 295                 300

Leu Ser Asp Ala Ile Leu Leu Ser Asp Ile Leu Arg Val Asn Thr Glu
305                 310                 315                 320

Ile Thr Lys Ala Pro Leu Ser Ala Ser Met Ile Lys Arg Tyr Asp Glu
                325                 330                 335

His His Gln Asp Leu Thr Leu Leu Lys Ala Leu Val Arg Gln Gln Leu
            340                 345                 350

Pro Glu Lys Tyr Lys Glu Ile Phe Phe Asp Gln Ser Lys Asn Gly Tyr
        355                 360                 365

Ala Gly Tyr Ile Asp Gly Gly Ala Ser Gln Glu Glu Phe Tyr Lys Phe
        370                 375                 380

Ile Lys Pro Ile Leu Glu Lys Met Asp Gly Thr Glu Glu Leu Leu Val
385                 390                 395                 400

Lys Leu Asn Arg Glu Asp Leu Leu Arg Lys Gln Arg Thr Phe Asp Asn
                405                 410                 415

Gly Ser Ile Pro His Gln Ile His Leu Gly Glu Leu His Ala Ile Leu
            420                 425                 430

Arg Arg Gln Glu Asp Phe Tyr Pro Phe Leu Lys Asp Asn Arg Glu Lys
        435                 440                 445

Ile Glu Lys Ile Leu Thr Phe Arg Ile Pro Tyr Tyr Val Gly Pro Leu
        450                 455                 460

Ala Arg Gly Asn Ser Arg Phe Ala Trp Met Thr Arg Lys Ser Glu Glu
465                 470                 475                 480

Thr Ile Thr Pro Trp Asn Phe Glu Glu Val Val Asp Lys Gly Ala Ser
                485                 490                 495

Ala Gln Ser Phe Ile Glu Arg Met Thr Asn Phe Asp Lys Asn Leu Pro
            500                 505                 510

Asn Glu Lys Val Leu Pro Lys His Ser Leu Leu Tyr Glu Tyr Phe Thr
        515                 520                 525

Val Tyr Asn Glu Leu Thr Lys Val Lys Tyr Val Thr Glu Gly Met Arg
        530                 535                 540

Lys Pro Ala Phe Leu Ser Gly Glu Gln Lys Lys Ala Ile Val Asp Leu
545                 550                 555                 560

Leu Phe Lys Thr Asn Arg Lys Val Thr Val Lys Gln Leu Lys Glu Asp
                565                 570                 575

Tyr Phe Lys Lys Ile Glu Cys Phe Asp Ser Val Glu Ile Ser Gly Val
            580                 585                 590

Glu Asp Arg Phe Asn Ala Ser Leu Gly Thr Tyr His Asp Leu Leu Lys
        595                 600                 605

Ile Ile Lys Asp Lys Asp Phe Leu Asp Asn Glu Glu Asn Glu Asp Ile
```

```
                610             615             620
Leu Glu Asp Ile Val Leu Thr Leu Thr Leu Phe Glu Asp Arg Glu Met
625             630             635             640

Ile Glu Glu Arg Leu Lys Thr Tyr Ala His Leu Phe Asp Asp Lys Val
                645             650             655

Met Lys Gln Leu Lys Arg Arg Tyr Thr Gly Trp Gly Arg Leu Ser
            660             665             670

Arg Lys Leu Ile Asn Gly Ile Arg Asp Lys Gln Ser Gly Lys Thr Ile
                675             680             685

Leu Asp Phe Leu Lys Ser Asp Gly Phe Ala Asn Arg Asn Phe Met Gln
690             695             700

Leu Ile His Asp Asp Ser Leu Thr Phe Lys Glu Asp Ile Gln Lys Ala
705             710             715             720

Gln Val Ser Gly Gln Gly Asp Ser Leu His Glu His Ile Ala Asn Leu
                725             730             735

Ala Gly Ser Pro Ala Ile Lys Lys Gly Ile Leu Gln Thr Val Lys Val
            740             745             750

Val Asp Glu Leu Val Lys Val Met Gly Arg His Lys Pro Glu Asn Ile
            755             760             765

Val Ile Glu Met Ala Arg Glu Asn Gln Thr Thr Gln Lys Gly Gln Lys
770             775             780

Asn Ser Arg Glu Arg Met Lys Arg Ile Glu Glu Gly Ile Lys Glu Leu
785             790             795             800

Gly Ser Gln Ile Leu Lys Glu His Pro Val Glu Asn Thr Gln Leu Gln
                805             810             815

Asn Glu Lys Leu Tyr Leu Tyr Tyr Leu Gln Asn Gly Arg Asp Met Tyr
            820             825             830

Val Asp Gln Glu Leu Asp Ile Asn Arg Leu Ser Asp Tyr Asp Val Asp
            835             840             845

Ala Ile Val Pro Gln Ser Phe Leu Lys Asp Asp Ser Ile Asp Asn Lys
850             855             860

Val Leu Thr Arg Ser Asp Lys Asn Arg Gly Lys Ser Asp Asn Val Pro
865             870             875             880

Ser Glu Glu Val Val Lys Lys Met Lys Asn Tyr Trp Arg Gln Leu Leu
                885             890             895

Asn Ala Lys Leu Ile Thr Gln Arg Lys Phe Asp Asn Leu Thr Lys Ala
            900             905             910

Glu Arg Gly Gly Leu Ser Glu Leu Asp Lys Ala Gly Phe Ile Lys Arg
            915             920             925

Gln Leu Val Glu Thr Arg Gln Ile Thr Lys His Val Ala Gln Ile Leu
930             935             940

Asp Ser Arg Met Asn Thr Lys Tyr Asp Glu Asn Asp Lys Leu Ile Arg
945             950             955             960

Glu Val Lys Val Ile Thr Leu Lys Ser Lys Leu Val Ser Asp Phe Arg
                965             970             975

Lys Asp Phe Gln Phe Tyr Lys Val Arg Glu Ile Asn Asn Tyr His His
            980             985             990

Ala His Asp Ala Tyr Leu Asn Ala Val Val Gly Thr Ala Leu Ile Lys
            995             1000            1005

Lys Tyr Pro Lys Leu Glu Ser Glu Phe Val Tyr Gly Asp Tyr Lys
    1010            1015            1020

Val Tyr Asp Val Arg Lys Met Ile Ala Lys Ser Glu Gln Glu Ile
    1025            1030            1035
```

```
Gly Lys Ala Thr Ala Lys Tyr Phe Phe Tyr Ser Asn Ile Met Asn
    1040            1045                1050

Phe Phe Lys Thr Glu Ile Thr Leu Ala Asn Gly Glu Ile Arg Lys
    1055            1060                1065

Arg Pro Leu Ile Glu Thr Asn Gly Glu Thr Gly Glu Ile Val Trp
    1070            1075                1080

Asp Lys Gly Arg Asp Phe Ala Thr Val Arg Lys Val Leu Ser Met
    1085            1090                1095

Pro Gln Val Asn Ile Val Lys Lys Thr Glu Val Gln Thr Gly Gly
    1100            1105                1110

Phe Ser Lys Glu Ser Ile Leu Pro Lys Arg Asn Ser Asp Lys Leu
    1115            1120                1125

Ile Ala Arg Lys Lys Asp Trp Asp Pro Lys Lys Tyr Gly Gly Phe
    1130            1135                1140

Asp Ser Pro Thr Val Ala Tyr Ser Val Leu Val Val Ala Lys Val
    1145            1150                1155

Glu Lys Gly Lys Ser Lys Lys Leu Lys Ser Val Lys Glu Leu Leu
    1160            1165                1170

Gly Ile Thr Ile Met Glu Arg Ser Ser Phe Glu Lys Asn Pro Ile
    1175            1180                1185

Asp Phe Leu Glu Ala Lys Gly Tyr Lys Glu Val Lys Lys Asp Leu
    1190            1195                1200

Ile Ile Lys Leu Pro Lys Tyr Ser Leu Phe Glu Leu Glu Asn Gly
    1205            1210                1215

Arg Lys Arg Met Leu Ala Ser Ala Gly Glu Leu Gln Lys Gly Asn
    1220            1225                1230

Glu Leu Ala Leu Pro Ser Lys Tyr Val Asn Phe Leu Tyr Leu Ala
    1235            1240                1245

Ser His Tyr Glu Lys Leu Lys Gly Ser Pro Glu Asp Asn Glu Gln
    1250            1255                1260

Lys Gln Leu Phe Val Glu Gln His Lys His Tyr Leu Asp Glu Ile
    1265            1270                1275

Ile Glu Gln Ile Ser Glu Phe Ser Lys Arg Val Ile Leu Ala Asp
    1280            1285                1290

Ala Asn Leu Asp Lys Val Leu Ser Ala Tyr Asn Lys His Arg Asp
    1295            1300                1305

Lys Pro Ile Arg Glu Gln Ala Glu Asn Ile Ile His Leu Phe Thr
    1310            1315                1320

Leu Thr Asn Leu Gly Ala Pro Ala Ala Phe Lys Tyr Phe Asp Thr
    1325            1330                1335

Thr Ile Asp Arg Lys Arg Tyr Thr Ser Thr Lys Glu Val Leu Asp
    1340            1345                1350

Ala Thr Leu Ile His Gln Ser Ile Thr Gly Leu Tyr Glu Thr Arg
    1355            1360                1365

Ile Asp Leu Ser Gln Leu Gly Gly Asp Pro Lys Lys Lys Arg Lys
    1370            1375                1380

Val Asp Ala Leu Asp Asp Phe Asp Leu Asp Met Leu Gly Ser Asp
    1385            1390                1395

Ala Leu Asp Asp Phe Asp Leu Asp Met Leu Gly Ser Asp Ala Leu
    1400            1405                1410

Asp Asp Phe Asp Leu Asp Met Leu Gly Ser Asp Ala Leu Asp Asp
    1415            1420                1425
```

```
Phe Asp Leu Asp Met Leu Tyr Ile Asp
    1430            1435

<210> SEQ ID NO 26
<211> LENGTH: 103
<212> TYPE: DNA
<213> ORGANISM: Artificial Sequence
<220> FEATURE:
<223> OTHER INFORMATION: 5-repeat GAL4 upstream activating sequence

<400> SEQUENCE: 26
cggagtactg tcctccgagc ggagtactgt cctccgactc gagcggagta ctgtcctccg      60
atcggagtac tgtcctccgc gaattccgga gtactgtcct ccg                       103

<210> SEQ ID NO 27
<211> LENGTH: 271
<212> TYPE: DNA
<213> ORGANISM: Artificial Sequence
<220> FEATURE:
<223> OTHER INFORMATION: Tet response element (TRE)

<400> SEQUENCE: 27
tccctatcag tgatagagaa aagtgaaagt cgagtttacc actccctatc agtgatagag      60
aaaagtgaaa gtcgagttta ccactcccta tcagtgatag agaaaagtga agtcgagtt     120 taccactccc tatcagtgat agagaaaagt gaaagtcgag tttaccactc cctatcagtg    180
atagagaaaa gtgaaagtcg agtttaccac tccctatcag tgatagagaa aagtgaaagt    240
cgagtttacc actccctatc agtgatagag a                                    271

<210> SEQ ID NO 28
<211> LENGTH: 78
<212> TYPE: DNA
<213> ORGANISM: Artificial Sequence
<220> FEATURE:
<223> OTHER INFORMATION: LacI promoter sequence

<400> SEQUENCE: 28
gacaccatcg aatggcgcaa aacctttcgc ggtatggcat gatagcgccc ggaagagagt      60
caattcaggg tggtgaat                                                    78

<210> SEQ ID NO 29
<211> LENGTH: 257
<212> TYPE: DNA
<213> ORGANISM: Mus musculus

<400> SEQUENCE: 29
ggtctgaaaa ggatttggag aaggggagct gaattcattt gcttttgtct gttaccagct      60 ctggggggcag agagagagcc atccctggg aacagcctga gaattcccac ttcccctgag    120
gagccctccc ttcttaggcc ctccagatgg tagtgtggac aaaaggcaat aattagcatg    180
agaatcggcc tccctcccag aggatgaggt catcggcctt ggccttgggt ggggaggcgg    240
agactgatct gaggagt                                                    257

<210> SEQ ID NO 30
<211> LENGTH: 507
<212> TYPE: DNA
<213> ORGANISM: Artificial Sequence
<220> FEATURE:
<223> OTHER INFORMATION: Glial Fibrillary Acidic Protein (GFAP)
      promoter sequence

<400> SEQUENCE: 30
```

```
acatatcctg gtgtggagta ggggacgctg ctctgacaga ggctcggggg cctgagctgg      60
ctctgtgagc tggggaggag gcagacagcc aggccttgtc tgcaagcaga cctggcagca     120
ttgggctggc cgccccccag ggcctcctct tcatgcccag tgaatgactc accttggcac     180
agacacaatg ttcggggtgg gcacagtgcc tgcttcccgc cgcaccccag cccccctcaa     240
atgccttccg agaagcccat tgagcaggga gctctcccca tagctgggct gcggcccaac     300 cccacccect caggctatgc caggggggtgt tgccaggggc acccgggcat cgccagtcta     360
gcccactcct tcataaagcc ctcgcatccc aggagcgagc agagccagag caggttggag     420
aggagacgca tcacctccgc tgctcgcggg gatcctctag agtcgacgga tccggggaat     480
tccccagtct caggatccac catgggg                                         507
```

<210> SEQ ID NO 31
<211> LENGTH: 151
<212> TYPE: DNA
<213> ORGANISM: Mus musculus

<400> SEQUENCE: 31

```
atccactgga aacgtcttga tgtgcagcaa cagcttagag gggggctcag gtttctgtgg      60
cgttggctat atttatctct gggttcatgc cagcagggag ggtttaaatg gcacccagca     120
gttggtgtga ggggctgcgg gagcttgggg g                                    151
```

<210> SEQ ID NO 32
<211> LENGTH: 142
<212> TYPE: DNA
<213> ORGANISM: Mus musculus

<400> SEQUENCE: 32

```
ccactacggg tctaggctgc ccatgtaagg aggcaaggcc tggggacacc cgagatgcct      60
ggttataatt aacccagaca tgtggctgcc ccccccccc caacacctgc tgcctctaaa     120
aataaccctg tccctggtgg at                                              142
```

<210> SEQ ID NO 33
<211> LENGTH: 771
<212> TYPE: DNA
<213> ORGANISM: Artificial Sequence
<220> FEATURE:
<223> OTHER INFORMATION: Murine muscle creatine kinase/alpha-myosin
      heavy chain (MHCK7) promoter

<400> SEQUENCE: 33

```
ccttcagatt aaaaataact gaggtaaggg cctgggtagg ggaggtggtg tgagacgctc      60
ctgtctctcc tctatctgcc catcggccct ttggggagga ggaatgtgcc caaggactaa     120
aaaaaggcca tggagccaga ggggcgaggg caacagacct tcatgggca aaccttgggg      180 ccctgctgtc tagcatgccc cactacgggt ctaggctgcc catgtaagga ggcaaggcct     240
ggggacaccc gagatgcctg gttataatta acccagacat gtggctgccc cccccccc     300 aacacctgct gcctctaaaa ataaccctgt ccctggtgga tccctgcat gcgaagatct     360 tcgaacaagg ctgtggggga ctgagggcag gctgtaacag gcttggggc cagggcttat     420 acgtgcctgg gactcccaaa gtattactgt tccatgttcc cggcgaaggg ccagctgtcc     480
cccgccagct agactcagca cttagtttag gaaccagtga gcaagtcagc ccttggggca     540
gcccatacaa ggccatgggg ctgggcaagc tgcacgcctg gtccggggt gggcacggtg     600 cccgggcaac gagctgaaag ctcatctgct ctcaggggcc cctccctggg gacagcccct     660
```

-continued

```
cctggctagt cacaccctgt aggctcctct atataaccca ggggcacagg ggctgccctc    720
attctaccac cacctccaca gcacagacag acactcagga gccagccagc c            771
```

<210> SEQ ID NO 34
<211> LENGTH: 16
<212> TYPE: PRT
<213> ORGANISM: Artificial Sequence
<220> FEATURE:
<223> OTHER INFORMATION: QBEnd10-binding epitope

<400> SEQUENCE: 34

Glu Leu Pro Thr Gln Gly Thr Phe Ser Asn Val Ser Thr Asn Val Ser
1               5                   10                  15

<210> SEQ ID NO 35
<211> LENGTH: 214
<212> TYPE: PRT
<213> ORGANISM: Artificial Sequence
<220> FEATURE:
<223> OTHER INFORMATION: SHP-1 SH2 complete domain

<400> SEQUENCE: 35

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr
    210

<210> SEQ ID NO 36
<211> LENGTH: 97
<212> TYPE: PRT
<213> ORGANISM: Artificial Sequence
<220> FEATURE:
<223> OTHER INFORMATION: SHP-1 SH2 1 sequence

<400> SEQUENCE: 36

Trp Phe His Arg Asp Leu Ser Gly Leu Asp Ala Glu Thr Leu Leu Lys
1               5                   10                  15

Gly Arg Gly Val His Gly Ser Phe Leu Ala Arg Pro Ser Arg Lys Asn
                20                  25                  30

Gln Gly Asp Phe Ser Leu Ser Val Arg Val Gly Asp Gln Val Thr His
            35                  40                  45

Ile Arg Ile Gln Asn Ser Gly Asp Phe Tyr Asp Leu Tyr Gly Gly Glu
        50                  55                  60

Lys Phe Ala Thr Leu Thr Glu Leu Val Glu Tyr Tyr Thr Gln Gln Gln
65                  70                  75                  80

Gly Val Leu Gln Asp Arg Asp Gly Thr Ile Ile His Leu Lys Tyr Pro
                85                  90                  95

Leu

<210> SEQ ID NO 37
<211> LENGTH: 104
<212> TYPE: PRT
<213> ORGANISM: Artificial Sequence
<220> FEATURE:
<223> OTHER INFORMATION: SHP-1 SH2 2 sequence

<400> SEQUENCE: 37

Trp Tyr His Gly His Met Ser Gly Gly Gln Ala Glu Thr Leu Leu Gln
1               5                   10                  15

Ala Lys Gly Glu Pro Trp Thr Phe Leu Val Arg Glu Ser Leu Ser Gln
                20                  25                  30

Pro Gly Asp Phe Val Leu Ser Val Leu Ser Asp Gln Pro Lys Ala Gly
            35                  40                  45

Pro Gly Ser Pro Leu Arg Val Thr His Ile Lys Val Met Cys Glu Gly
        50                  55                  60

Gly Arg Tyr Thr Val Gly Gly Leu Glu Thr Phe Asp Ser Leu Thr Asp
65                  70                  75                  80

Leu Val Glu His Phe Lys Lys Thr Gly Ile Glu Glu Ala Ser Gly Ala
                85                  90                  95

Phe Val Tyr Leu Arg Gln Pro Tyr
            100

<210> SEQ ID NO 38
<211> LENGTH: 97
<212> TYPE: PRT
<213> ORGANISM: Artificial Sequence
<220> FEATURE:
<223> OTHER INFORMATION: SHP-2 first SH2 domain

<400> SEQUENCE: 38

Trp Phe His Pro Asn Ile Thr Gly Val Glu Ala Glu Asn Leu Leu Leu
1               5                   10                  15

Thr Arg Gly Val Asp Gly Ser Phe Leu Ala Arg Pro Ser Lys Ser Asn
                20                  25                  30

Pro Gly Asp Phe Thr Leu Ser Val Arg Arg Asn Gly Ala Val Thr His
            35                  40                  45

Ile Lys Ile Gln Asn Thr Gly Asp Tyr Tyr Asp Leu Tyr Gly Gly Glu
        50                  55                  60

Lys Phe Ala Thr Leu Ala Glu Leu Val Gln Tyr Tyr Met Glu His His
65                  70                  75                  80

Gly Gln Leu Lys Glu Lys Asn Gly Asp Val Ile Glu Leu Lys Tyr Pro
                85                  90                  95

Leu

<210> SEQ ID NO 39
<211> LENGTH: 105
<212> TYPE: PRT
<213> ORGANISM: Artificial Sequence
<220> FEATURE:
<223> OTHER INFORMATION: SHP-2 second SH2 domain

<400> SEQUENCE: 39

```
Trp Phe His Gly His Leu Ser Gly Lys Glu Ala Glu Lys Leu Leu Thr
1               5                   10                  15
Glu Lys Gly Lys His Gly Ser Phe Leu Val Arg Glu Ser Gln Ser His
            20                  25                  30
Pro Gly Asp Phe Val Leu Ser Val Arg Thr Gly Asp Asp Lys Gly Glu
        35                  40                  45
Ser Asn Asp Gly Lys Ser Lys Val Thr His Val Met Ile Arg Cys Gln
    50                  55                  60
Glu Leu Lys Tyr Asp Val Gly Gly Gly Glu Arg Phe Asp Ser Leu Thr
65                  70                  75                  80
Asp Leu Val Glu His Tyr Lys Lys Asn Pro Met Val Glu Thr Leu Gly
                85                  90                  95
Thr Val Leu Gln Leu Lys Gln Pro Leu
            100                 105
```

<210> SEQ ID NO 40
<211> LENGTH: 211
<212> TYPE: PRT
<213> ORGANISM: Artificial Sequence
<220> FEATURE:
<223> OTHER INFORMATION: SHP-2 both SH2 domains

<400> SEQUENCE: 40

```
Trp Phe His Pro Asn Ile Thr Gly Val Glu Ala Glu Asn Leu Leu Leu
1               5                   10                  15
Thr Arg Gly Val Asp Gly Ser Phe Leu Ala Arg Pro Ser Lys Ser Asn
            20                  25                  30
Pro Gly Asp Phe Thr Leu Ser Val Arg Arg Asn Gly Ala Val Thr His
        35                  40                  45
Ile Lys Ile Gln Asn Thr Gly Asp Tyr Tyr Asp Leu Tyr Gly Gly Glu
    50                  55                  60
Lys Phe Ala Thr Leu Ala Glu Leu Val Gln Tyr Tyr Met Glu His His
65                  70                  75                  80
Gly Gln Leu Lys Glu Lys Asn Gly Asp Val Ile Glu Leu Lys Tyr Pro
                85                  90                  95
Leu Asn Cys Ala Asp Pro Thr Ser Glu Arg Trp Phe His Gly His Leu
            100                 105                 110
Ser Gly Lys Glu Ala Glu Lys Leu Leu Thr Glu Lys Gly Lys His Gly
            115                 120                 125
Ser Phe Leu Val Arg Glu Ser Gln Ser His Pro Gly Asp Phe Val Leu
        130                 135                 140
Ser Val Arg Thr Gly Asp Asp Lys Gly Glu Ser Asn Asp Gly Lys Ser
145                 150                 155                 160
Lys Val Thr His Val Met Ile Arg Cys Gln Glu Leu Lys Tyr Asp Val
                165                 170                 175
Gly Gly Gly Glu Arg Phe Asp Ser Leu Thr Asp Leu Val Glu His Tyr
            180                 185                 190
```

```
Lys Lys Asn Pro Met Val Glu Thr Leu Gly Thr Val Leu Gln Leu Lys
        195                 200                 205

Gln Pro Leu
    210

<210> SEQ ID NO 41
<211> LENGTH: 196
<212> TYPE: PRT
<213> ORGANISM: Artificial Sequence
<220> FEATURE:
<223> OTHER INFORMATION: truncated TGF beta receptor 2 sequence

<400> SEQUENCE: 41

Met Gly Trp Ser Cys Ile Ile Leu Phe Leu Val Ala Thr Ala Thr Gly
1               5                   10                  15

Val His Ser Thr Ile Pro Pro His Val Gln Lys Ser Val Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Lys Pro Gly Glu
        115                 120                 125

Thr Phe Phe Met Cys Ser Cys Ser Ser Asp Glu Cys Asn Asp Asn Ile
    130                 135                 140

Ile Phe Ser Glu Glu Tyr Asn Thr Ser Asn Pro Asp Leu Leu Leu Val
145                 150                 155                 160

Ile Phe Gln Val Thr Gly Ile Ser Leu Leu Pro Pro Leu Gly Val Ala
                165                 170                 175

Ile Ser Val Ile Ile Ile Phe Tyr Cys Tyr Arg Val Asn Arg Gln Gln
            180                 185                 190

Lys Leu Ser Ser
        195

<210> SEQ ID NO 42
<211> LENGTH: 517
<212> TYPE: PRT
<213> ORGANISM: Artificial Sequence
<220> FEATURE:
<223> OTHER INFORMATION: transgene FRB-FKBP12-L3-dCasp9

<400> SEQUENCE: 42

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
```

```
            65                  70                  75                  80
Leu Leu Gln Ala Trp Asp Leu Tyr Tyr His Val Phe Arg Arg Ile Ser
                    85                  90                  95
Lys Leu Glu Tyr Ser Gly Gly Ser Leu Glu Gly Val Gln Val Glu
                100                 105                 110
Thr Ile Ser Pro Gly Asp Gly Arg Thr Phe Pro Lys Arg Gly Gln Thr
                    115                 120                 125
Cys Val Val His Tyr Thr Gly Met Leu Glu Asp Gly Lys Lys Phe Asp
            130                 135                 140
Ser Ser Arg Asp Arg Asn Lys Pro Phe Lys Phe Met Leu Gly Lys Gln
145                 150                 155                 160
Glu Val Ile Arg Gly Trp Glu Gly Val Ala Gln Met Ser Val Gly
                    165                 170                 175
Gln Arg Ala Lys Leu Thr Ile Ser Pro Asp Tyr Ala Tyr Gly Ala Thr
                180                 185                 190
Gly His Pro Gly Ile Ile Pro Pro His Ala Thr Leu Val Phe Asp Val
            195                 200                 205
Glu Leu Leu Lys Leu Glu Ser Gly Gly Gly Ser Gly Gly Gly Gly
    210                 215                 220
Ser Gly Gly Gly Gly Ser Gly Val Asp Gly Phe Gly Asp Val Gly Ala
225                 230                 235                 240
Leu Glu Ser Leu Arg Gly Asn Ala Asp Leu Ala Tyr Ile Leu Ser Met
                    245                 250                 255
Glu Pro Cys Gly His Cys Leu Ile Ile Asn Asn Val Asn Phe Cys Arg
                260                 265                 270
Glu Ser Gly Leu Arg Thr Arg Thr Gly Ser Asn Ile Asp Cys Glu Lys
            275                 280                 285
Leu Arg Arg Arg Phe Ser Ser Leu His Phe Met Val Glu Val Lys Gly
    290                 295                 300
Asp Leu Thr Ala Lys Lys Met Val Leu Ala Leu Leu Glu Leu Ala Gln
305                 310                 315                 320
Gln Asp His Gly Ala Leu Asp Cys Cys Val Val Ile Leu Ser His
                    325                 330                 335
Gly Cys Gln Ala Ser His Leu Gln Phe Pro Gly Ala Val Tyr Gly Thr
                340                 345                 350
Asp Gly Cys Pro Val Ser Val Glu Lys Ile Val Asn Ile Phe Asn Gly
            355                 360                 365
Thr Ser Cys Pro Ser Leu Gly Gly Lys Pro Lys Leu Phe Phe Ile Gln
    370                 375                 380
Ala Cys Gly Gly Glu Gln Lys Asp His Gly Phe Glu Val Ala Ser Thr
385                 390                 395                 400
Ser Pro Glu Asp Glu Ser Pro Gly Ser Asn Pro Glu Pro Asp Ala Thr
                    405                 410                 415
Pro Phe Gln Glu Gly Leu Arg Thr Phe Asp Gln Leu Asp Ala Ile Ser
                420                 425                 430
Ser Leu Pro Thr Pro Ser Asp Ile Phe Val Ser Tyr Ser Thr Phe Pro
            435                 440                 445
Gly Phe Val Ser Trp Arg Asp Pro Lys Ser Gly Ser Trp Tyr Val Glu
    450                 455                 460
Thr Leu Asp Asp Ile Phe Glu Gln Trp Ala His Ser Glu Asp Leu Gln
465                 470                 475                 480
Ser Leu Leu Leu Arg Val Ala Asn Ala Val Ser Val Lys Gly Ile Tyr
                    485                 490                 495
```

Lys Gln Met Pro Gly Cys Phe Asn Phe Leu Arg Lys Lys Leu Phe Phe
            500                 505                 510

Lys Thr Ser Ala Ser
        515

<210> SEQ ID NO 43
<211> LENGTH: 136
<212> TYPE: PRT
<213> ORGANISM: Artificial Sequence
<220> FEATURE:
<223> OTHER INFORMATION: sort-suicide gene RQR8

<400> SEQUENCE: 43

Cys Pro Tyr Ser Asn Pro Ser Leu Cys Ser Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
        35                  40                  45

Ser Gly Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Val Val
        130                 135

<210> SEQ ID NO 44
<211> LENGTH: 20
<212> TYPE: PRT
<213> ORGANISM: Foot-and-mouth disease virus

<400> SEQUENCE: 44

Arg Ala Glu Gly Arg Gly Ser Leu Leu Thr Cys Gly Asp Val Glu Glu
1               5                   10                  15

Asn Pro Gly Pro
            20

<210> SEQ ID NO 45
<211> LENGTH: 20
<212> TYPE: PRT
<213> ORGANISM: Foot-and-mouth disease virus

<400> SEQUENCE: 45

Gln Cys Thr Asn Tyr Ala Leu Leu Lys Leu Ala Gly Asp Val Glu Ser
1               5                   10                  15

Asn Pro Gly Pro
            20

<210> SEQ ID NO 46
<211> LENGTH: 17
<212> TYPE: DNA
<213> ORGANISM: Artificial Sequence
<220> FEATURE:
<223> OTHER INFORMATION: GAL4 DNA binding sequence -continued

```
<220> FEATURE:
<221> NAME/KEY: misc_feature
<222> LOCATION: (4)..(14)
<223> OTHER INFORMATION: n is a, c, g, or t

<400> SEQUENCE: 46
cggnnnnnnn nnnnccg                                                  17

<210> SEQ ID NO 47
<211> LENGTH: 10
<212> TYPE: DNA
<213> ORGANISM: Artificial Sequence
<220> FEATURE:
<223> OTHER INFORMATION: Transcription factor C/EBP recognition sequence

<400> SEQUENCE: 47
attgcgcaat                                                          10
```

CAR T-CELLS COMPRISING TRANSCRIPTIONAL CIRCUITS

CROSS-REFERENCE TO RELATED APPLICATIONS

This is a U.S. National Phase of International Application No. PCT/GB2018/053088, filed Oct. 24, 2018, which claims priority to Great Britain Application No. 1717524.1, filed Oct. 25, 2017.

FIELD OF THE INVENTION

The present invention relates to the transduction or transfection of cells with multiple vectors. In particular, the present invention relates to kit of vectors in which a first vector expresses a transcription factor upon which the expression of a transgene from a second vector is dependent. Cascading or rotating transcriptional circuits are also described, based on this principle.

BACKGROUND TO THE INVENTION

The genetic modification of therapeutic immune cells often involves the introduction of genes which re-target T-cells to, for example, cancer antigens. Such re-targeting genes include chimeric antigen receptors (CARs) and transgenic T-cell receptors (TCRs). To increase the potency and safety of engineered T-cells, such therapeutic approaches are increasing in complexity with introduction of multiple additional genetic elements.

For example, the cells may also be modified to introduce genes with other functions, such as genes which enhance proliferation, survival or allow pharmacological control of immune cells. Alternatively, or in addition, the cells may be engineered to express marker genes. These typically encode surface expression proteins which allow selection or transduced cells during cell production. Alternatively, or in addition, the cells may be engineered to express antibiotic resistance genes which allow selection during production by exposure to an antibiotic.

There is therefore a need to introduce multiple transgenes into therapeutic immune cells.

Gene vectors which are used to introduce transgenes into therapeutic immune cells are typically integrating vectors since expression must be long-lived. To date, the vector system of choice is retroviral vectors, which include gamma-retroviral vectors and lentiviral vectors.

Vector systems can allow expression of multiple genes from a single cassette using internal ribosome entry sequences or self-cleaving protein motifs such as FMD-2A like peptides. However, expression cassettes encoding multiple genes often cannot be expressed by a single vector because they are too large: the packaging limit of retroviral vectors varies with subtype and pseudotype but is typically under 10 kb.

One solution to this limitation is to simply transduce a T-cell with multiple vectors. However, as transduction is not 100 percent efficient, this creates a mixed population of cells with multiple combinations of vectors. Only a subset of the cells will have been successfully transduced with all vectors.

There is therefore a need for alternative vector systems capable of expressing multiple transgenes.

The GAL4 transcription factor sequences were downstream of RQR8 in the retroviral vector SFGmR, with a 2a self-cleaving peptide sequence enabling the expression of both proteins (top image). The GAL4 UAS sequence was cloned into the SIN retroviral construct pSuper, placing expression of the V5-tagged anti-CD19 second generation CAR under the control of the inducible promoter. An internal PGK promoter enabled the expression HA8 a cell surface marker used to detect transduced cells (bottom image).

Figure 7:
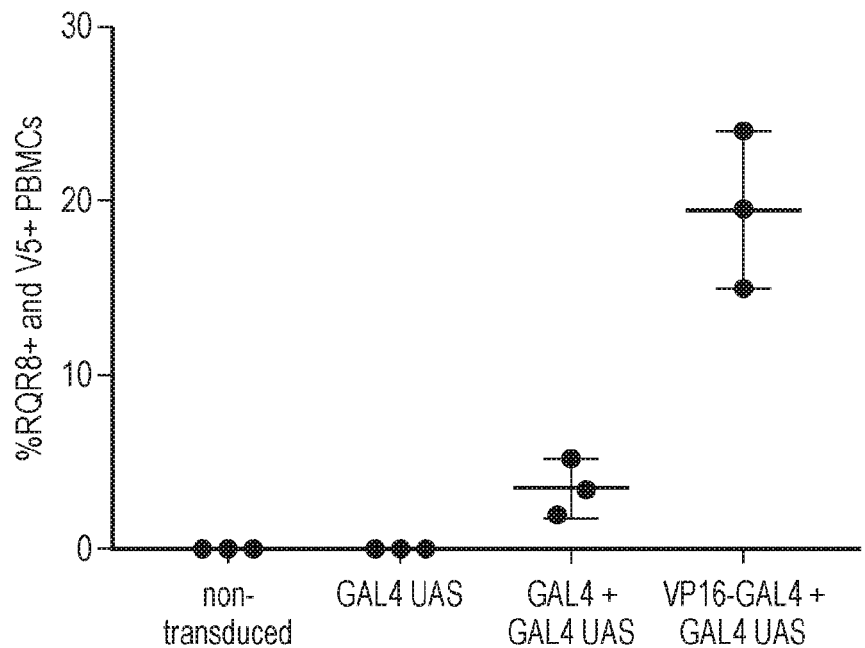

FIG. 7—Quantification of RQR8 and V5 double positive PBMCs

Quantification of the percentage of RQR8 and V5 double positive cells indicated that expression required the presence of active VP16-GAL4 transcription factor with the GAL4 UAS promoter (Example 2).

Figure 8:
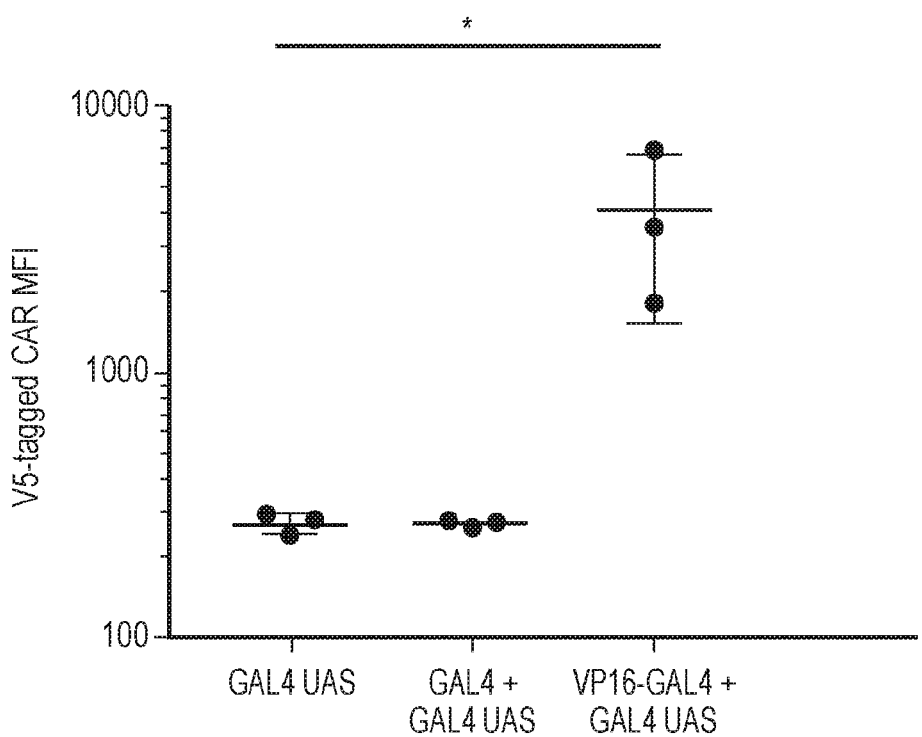

FIG. 8—Quantification of the V5-tagged CAR MFI

Quantification of the median fluorescent intensity of the V5-tagged CAR showed that there was a 15-fold increase in expression of the CAR when cells were co-transduced with the GAL4 UAS promoter and VP16-GAL4 transcription factor compared to co-transduction with the GAL4 DBD or the promoter alone. Statistical analysis: 1 way ANOVA Dunnett's multiple comparisons test*$p<0.05$ (Example 2).

Figure 9:
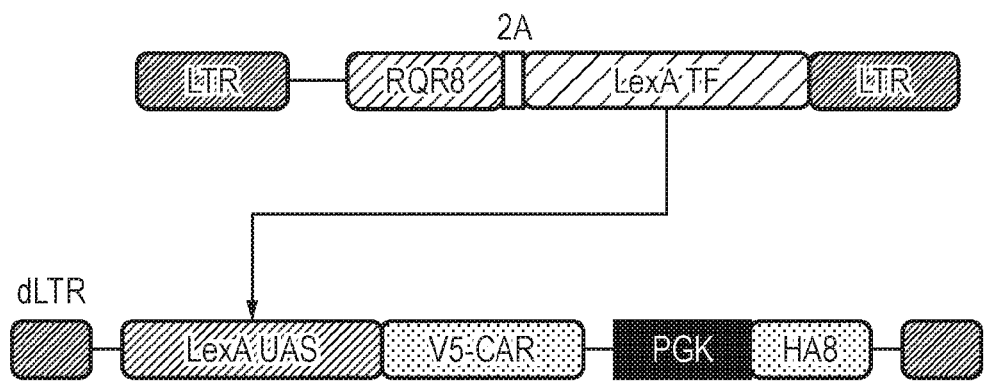

FIG. 9—Structure of LexA constructs described in Example 3

The top image illustrates the retroviral construct containing the sort selection marker RQR8 and the chimeric VP16-LexA transcription factor. The lower cartoon shows the structure of the SIN retroviral construct with the LexA UAS driving the expression of the V5-tagged anti-CD19 second generation CAR and the internal human PGK promoter controlling the expression of an HA8 marker (HA epitope presented on a CD8a stalk).

Figure 10:
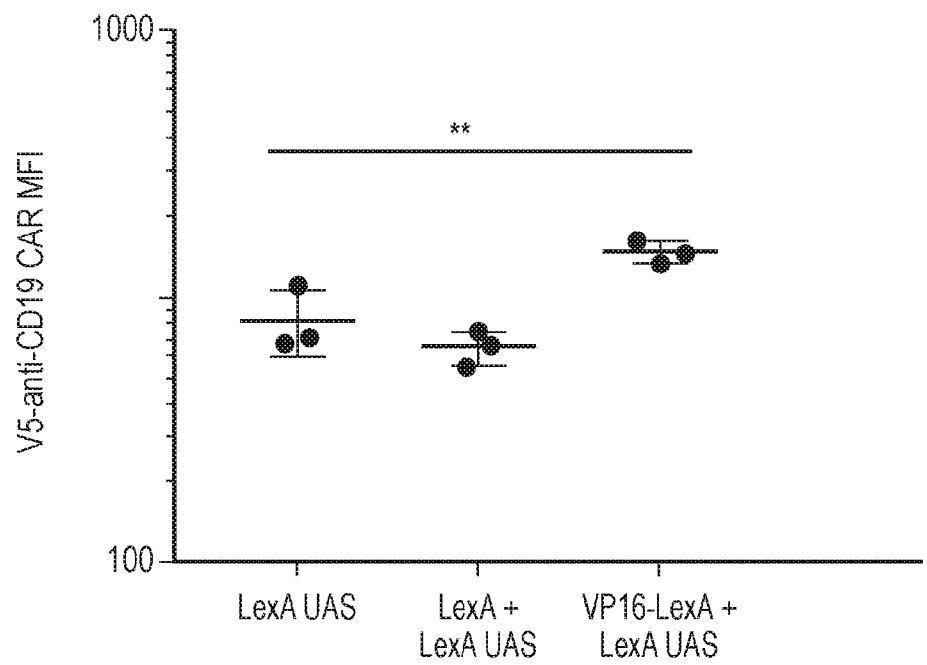

FIG. 10—Quantification of MFI of V5-tagged CAR.

Quantification of the MFI of the V5-tagged antib-CD19 CAR demonstrated that expression increased when PBMCs were co-transduced with the LexA UAS promoter construct and the active VP16-LexA transcription factor. Expression of the V5-tagged anti-CD19 CAR increased in PBMCs co-transduced with the LexA UAS promoter and the active VP16-LexA transcription factor, but not with the inactive LexA DNA-binding domain alone transcription factor.

Figure 11:
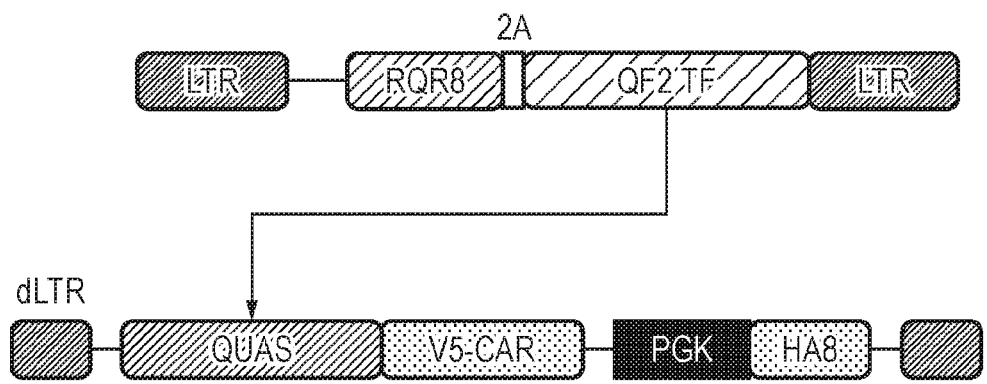

FIG. 11—Diagram of QF2 system described in Example 4

Similar to the GAL4 and LexA systems, the QF2 system utilises a retroviral construct to express RQR8 sort selection marker and the QF2 transcription factor and a SIN retroviral construct to control the expression of a V5-tagged CAR from the QUAS promoter. Expression of a HA8 marker in the SIN retroviral construct is driven by an internal PGK promoter.

Figure 12:
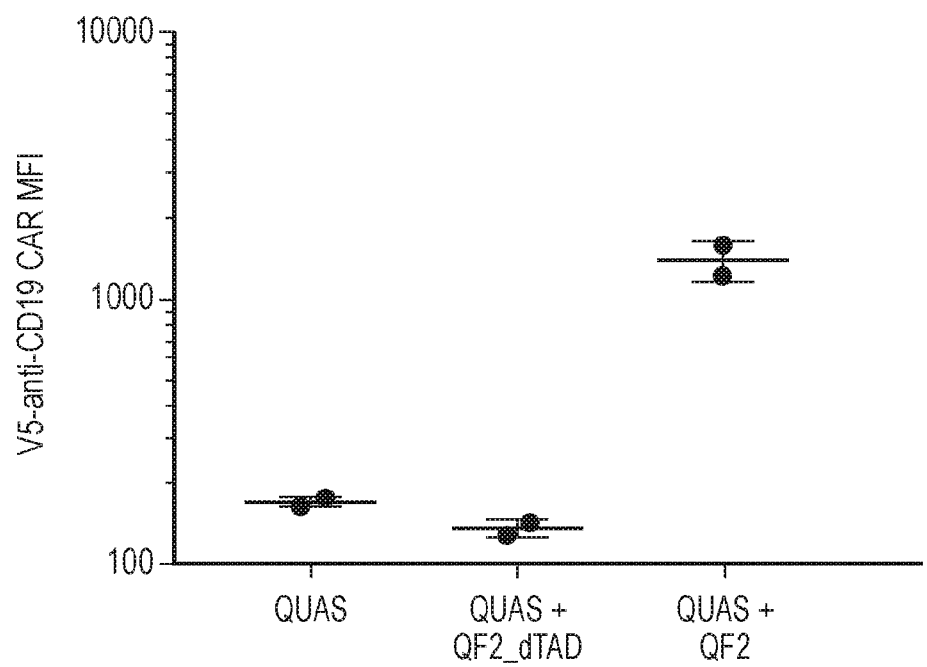

FIG. 12—Quantification of V5-tagged anti-CD19 CAR MFI

Quantification of the median fluorescence intensity of the V5-tagged anti-CD19 CAR showed that the expression was 8-fold higher in PBMCs co-transduced with the active QF2 transcription factor and QUAS promoter construct, indicating that the QF2 transcription factor is functional in PBMCs and able to initiate transcription from its cognate UAS.

Figure 13:
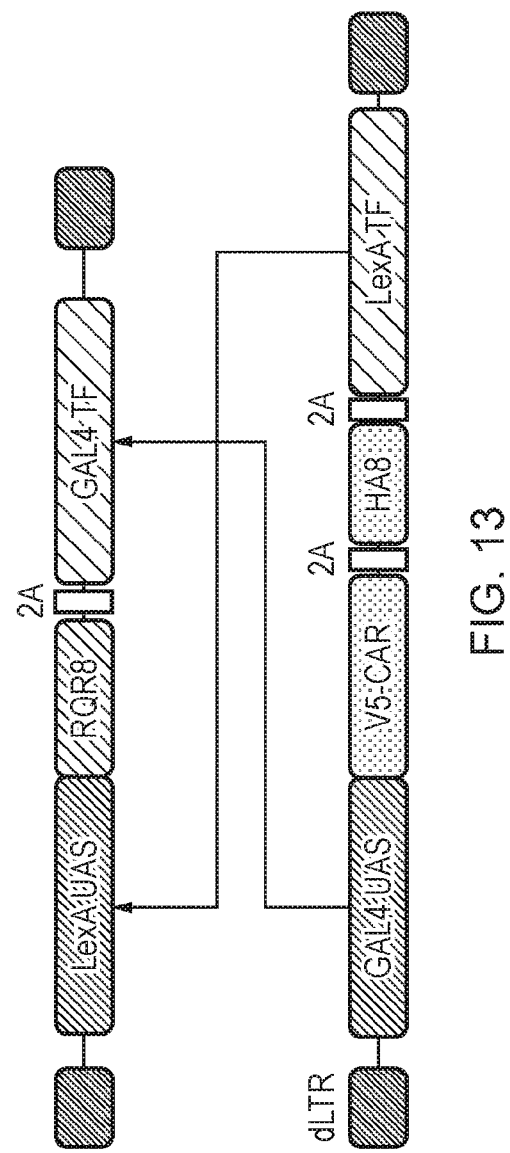

FIG. 13—Diagram of circular transcriptional dependent circuit constructs described in Example 5

A pair of SIN retroviral constructs with opposing UAS and artificial transcription factors are used to set up a self-amplifying circuit that is initiated by leaky expression from the SIN retroviral constructs. The top construct contains a LexA UAS that drives expression of the sort selection marker RQR8 and the VP16-GAL4 transcription factor, while to bottom construct has a GAL4 UAS controlling expression of a V5-tagged anti-CD19 CAR, HA8 marker and LexA transcription factor. When a cell is transduced with both constructs, leaky transcription should initiate expression of all components and set up a self-amplifying circular transcriptional circuit.

SUMMARY OF ASPECTS OF THE INVENTION

The present inventors have developed a vector system comprising two or more vectors in which expression of a transgene from one vector is dependent on expression of a transcription factor from another vector. Successful transduction with both vectors can be deduced via expression of a marker gene. It is therefore possible to detect and sort for cells expressing both or all of the vectors in the kit.

Thus in a first aspect, the present invention provides a kit of vectors for transducing an immune cell with multiple transgenes comprising:
(i) a first vector which comprises a first transgene and a nucleotide sequence encoding a transcription factor and; and
(ii) a second vector which comprises a second transgene wherein expression of the second transgene within a host cell is dependent upon expression of the transcription factor.

The second vector may also comprise a marker gene, the expression of which is dependent on the expression of the transcription factor. Expression of the marker by a cell transduced with the kit of vector indicates that the cell has been successfully transduced with both the first and second vector.

The kit of vectors may comprise more than one dependent vector. For example, the kit of vectors may comprise:
(i) a first vector which comprises a first transgene and a nucleotide sequence encoding a transcription factor; and
(ii) a second vector which comprises a second transgene; and
(iii) a third vector which comprises a third transgene
wherein expression of the second and third transgenes within a host cell is dependent upon expression of the transcription factor.

The kit of vectors may comprise iterative dependent vectors. For example, the kit of vectors may comprise:
(i) a first vector which comprises a first transgene and a nucleotide sequence encoding a first transcription factor; and
(ii) a second vector which comprises a second transgene and a nucleotide sequence encoding a second transcription factor; and
(iii) a third vector which comprises a third transgene
wherein expression of the second transgene within a host cell is dependent upon expression of the first transcription factor, and expression of the third transgene within a host cell is dependent upon expression of the second transcription factor.

In this embodiment, the third vector may also comprise a marker gene, the expression of which is dependent on the expression of the second transcription factor. Expression of the marker by a cell transduced with the kit of vector indicates that the cell has been successfully transduced with all three vectors.

The kit of vectors may comprise inter-dependent vectors. For example, the kit of vectors may comprise:
(i) a first vector which comprises a first transgene and a nucleotide sequence encoding a first transcription factor; and
(ii) a second vector which comprises a second transgene and a nucleotide sequence encoding a second transcription factor;
wherein expression of the second transgene within a host cell is dependent upon expression of the first transcription factor, and expression of the first transgene within a host cell is dependent upon expression of the second transcription factor.

One or more of the vector(s) in the kit may also comprises a marker gene.

The vectors may be plasmids, transposons, retroviral vectors or lentiviral vectors.

The transcription factor may be a prokaryotic or eukaryotic transcription factor that is functional in human cells. Examples of such transcription factors include LexA, TetR and LacI from bacteria; GAL4 from yeast; or QF, a transcriptional activator binding to QF Upstream Activating Sequences (QUAS) present in the qa cluster from *Neurospora*.

The transcription factor may be an artificial factor consisting of a DNA-binding domain, recognising a unique DNA sequence present in a promoter, and a transactivation domain derived from another transcription factor. Examples of such transcription factors include fusions between the DNA-binding domain of GAL4, LexA, Lac repressor, or QF and the transactivation domain of herpes simplex virus virion protein 16 (VP16).

The transcription factor may be a tissue-specific transcription factor that is not expressed in an immune cell and could be used to drive transcription from its cognate tissue-specific promoter. Examples of tissue-specific transcription factors include those from muscle cells such as MyoD, muscle enhancer factor 2 (MEF2) and Krueppel-like factor 3 (KLF3) or those from neuronal cells such as nuclear factor 1C (NF1C) and nuclear factor 1X (NF1X) from astrocytes or Brain-1 (Brn-1) and Brain-2 (Brn-2) from glial cells.

The transcription factor may be an artificial transcription factor generated by creating a fusion between: a zinc finger DNA-binding domain; or a transcription factor-like effector (TALE) DNA-binding domain; or a catalytically inactive form of the RNA-guided endonuclease Cas9 fused to the transactivation domain of VP16.

The first vector may comprise a constitutively active promoter.

One or more of the transgene(s) may encode a chimeric antigen receptor (CAR) or a T-cell receptor (TCR).

In a second aspect, the present invention provides a cell. The cell may comprise a transgene and a nucleotide sequence encoding a non-endogenous transcription factor, wherein expression of the transgene is dependent upon expression of the non-endogenous transcription factor.

The cell may be transfected or transduced with a kit of vectors according to the first aspect of the invention.

The cell may be an immune cell, such as a T-cell or natural killer (NK) cell.

In a third aspect, the present invention provides a method for making a cell according to the second aspect of the invention which comprises the step of transducing or transfecting a cell with a kit of vectors according to the first aspect of the invention.

In a fourth aspect there is provided a method for making a cell composition expressing a kit of vectors according to the first aspect of the invention, which comprises the following steps:
(i) transducing or transfecting a cell with a kit of vectors according to the first aspect of the invention wherein one of the vectors comprises a marker gene; and
(ii) selecting cells which express the marker gene
wherein expression of the marker gene by a cell indicates that the comprises all of the vectors in the kit.

The cell or cells may be transduced or transfected ex vivo.

In a fifth aspect, the present invention provides a pharmaceutical composition comprising a plurality of cells according to the second aspect of the invention.

In a sixth aspect, the present invention provides a pharmaceutical composition according to the fifth aspect of the invention for use in treating and/or preventing a disease.

In a seventh aspect, the present invention provides a method for treating and/or preventing a disease, which comprises the step of administering a pharmaceutical composition according to the fifth aspect of the invention to a subject.

The method may comprise the following steps:
(i) isolation of a cell containing sample from a subject;
(ii) transduction or transfection of the cells with a kit of vectors according to the first aspect of the invention; and
(iii) administering the cells from step (ii) to the subject.

In an eighth aspect, the present invention provides the use of a pharmaceutical composition according to the fifth aspect of the invention in the manufacture of a medicament for the treatment and/or prevention of a disease.

The disease may be a cancer.

The present invention therefore provide a kit of vectors enabling flexible, modular expression of multiple transgenes in a cell. If one cassette is dependent on a transcription factor for expression and the other cassette supplies the transcription factor, a transcriptional circuit can be established whereby expression of one cassette is dependent on expression of the other cassette. It is therefore possible to detect and select for cells have been successfully transduced with both or all vectors in the kit and therefore express all of the transgenes in the kit.

In addition to addressing the issue of packaging limits for single retroviral vectors, the system of the invention also offers other advantages. A modular approach is intrinsically desirable as it enables different mixtures of transgenes to be selected according for example to a patient's disease, morbidity etc. The system of the invention also facilitates the generation of a therapeutic product whereby a proportion of the immune cells express transgenes from one vector, and a proportion of immune cells express both.

DETAILED DESCRIPTION

Vectors

The present invention relates to a kit of vectors. A vector is used to introduce one or more nucleic acid sequence(s) into a host cell so that it expresses the protein(s) encoded by the nucleic acid sequence(s).

The vector may, for example, be a plasmid or a viral vector, such as a retroviral vector or a lentiviral vector, or a transposon based vector or synthetic mRNA.

The vector may be capable of transfecting or transducing an immune cell such as a T-cell or a natural killer (NK) cell.

Transcription Factor

At least one vector in the kit of the invention comprises a nucleic acid encoding a transcription factor.

A transcription factor is a protein which controls the rate of transcription of genetic information from DNA to messenger RNA, by binding to a specific DNA sequence and regulate the expression of a gene which comprises or is adjacent to that sequence.

Transcription factors work by promoting (as an activator), or blocking (as a repressor) the recruitment of RNA polymerase.

Transcription factors contain at least one DNA-binding domain (DBD), which attaches to either an enhancer or promoter region of DNA. Depending on the transcription factor, the transcription of the adjacent gene is either up- or down-regulated. Transcription factors also contain a trans-activating domain (TAD), which has binding sites for other proteins such as transcription co-regulators.

Transcription factors use a variety of mechanisms for the regulation of gene expression, including stabilizing or blocking the binding of RNA polymerase to DNA, or catalyzing the acetylation or deacetylation of histone proteins. The transcription factor may have histone acetyltransferase (HAT) activity, which acetylates histone proteins, weakening the association of DNA with histones and making the DNA more accessible to transcription, thereby up-regulating transcription. Alternatively the transcription factor may have histone deacetylase (HDAC) activity, which deacetylates histone proteins, strengthening the association of DNA with histones and making the DNA less accessible to transcription, thereby down-regulating transcription. Another mechanism by which they may function is by recruiting coactivator or corepressor proteins to the transcription factor DNA complex.

Some examples of specific transcription factors are given in the table below:

| Factor | Structural type | Recognition sequence | Binds as |
|---|---|---|---|
| SP1 | Zinc finger | 5'-GGGCGG-3' | Monomer |
| AP-1 | Basic zipper | 5'-TGA(G/C)TCA-3' | Dimer |
| C/EBP | Basic zipper | 5'-ATTGCGCAAT-3' (SEQ ID No. 47) | Dimer |
| Heat shock factor | Basic zipper | 5'-XGAAX-3' | Trimer |
| ATF/CREB | Basic zipper | 5'-TGACGTCA-3' | Dimer |
| c-Myc | Basic helix-loop-helix | 5'-CACGTG-3' | Dimer |
| Oct-1 | Helix-turn-helix | 5'-ATGCAAAT-3' | Monomer |
| NF-1 | Novel | 5'-TTGGCXXXXXGCCAA-3' | Dimer |

The transcription factor of the present invention may be constitutively active or conditionally active, i.e. requiring activation.

In the kit of vectors of the present invention, a constitutively active transcription factor modulates expression of the second transgene as soon as it is produced, without requiring an additional step such as cleavage from a membrane-tethered position in the cell or dimerization induced by addition of a dimerising agent.

Transcription Factors Applied to Human Immune Cells

DNA binding elements from some prokaryotic transcription factors can function as part of a transcriptional system in human immune cells. Those with demonstrated functional activity in human cells include GAL4 (from the galactose operon), LexA (the lex operon), LacI (the lactose operon repressor), TetR (the tetracycline sensitive repressor) and the Q system (which controls quinic acid catabolism).

The amino acid sequence of LexA from *Escherichia coli* is available from Uniprot (accession number Q1R3P3) and is shown below as SEQ ID No 1.

Amino acid sequence of LexA repressor
SEQ ID No. 1
MKALTARQQEVFDLIRDHISQTGMPPTRAEIAQRLGFRSPNAAEEHLKA

LARKGVIEIVSGASRGIRLLQEEEEGLPLVGRVAAGEPLLAQQHIEGHY

QVDPSLFKPNADFLLRVSGMSMKDIGIMDGDLLAVHKTQDVRNGQVVVA

RIDDEVTVKRLKKQGNKVELLPENSEFKPIVVDLRQQSFTIEGLAVGVI

RNGDWL

The amino acid sequence of the lactose operon repressor is available from Uniprot (Accession number F4VAC4) and is shown below as SEQ ID No. 2.

Amino acid sequence of Lactose operon repressor
SEQ ID No. 2
MVNVKPVTLYDVAEYAGVSYQTVSRVVNQASHVSAKTREKVEAAMAELN

YIPNRVAQQLAGKQSLLIGVATSSLALHAPSQIVAAIKSRADQLGASVV

VSMVERSGVEACKAAVHNLLAQRVSGLIINYPLDDQDAIAVEAACTNVP

ALFLDVSDQTPINSIIFSHEDGTRLGVEHLVALGHQQIALLAGPLSSVS

ARLRLAGWHKYLTRNQIQPIAEREGDWSAMSGFQQTMQMLNEGIVPTAM

LVANDQMALGAMRAITESGLRVGADISVVGYDDTEDSSCYIPPLTTIKQ

DFRLLGQTSVDRLLQLSQGQAVKGNQLLPVSLVKRKTTLAPNTQTASPR

ALADSLMQLARQVSRLESGQ

The amino acid sequence of the tetracycline repressor from *Escherichia coli* is available from UNiprot (accession number B1VCF0) and is shown below as SEQ ID No. 3.

Amino acid sequence of tetracycline repressor
SEQ ID No. 3
MMSRLDKSKVINSALELLNEVGIEGLTTRKLAQKLGVEQPTLYWHVKNK

RALLDALAIEMLDRHHTHFCPLEGESWQDFLRNNAKSFRCALLSHRDGA

KVHLGTRPTEKQYETLENQLAFLCQQGFSLENALYALSAVGHFTLGCVL

EDQEHQVAKEERETPTTDSMPPLLRQAIELFDHQGAEPAFLFGLELIIC

GLEKQLKCESGS

The amino acid sequence of GAL4 is available from Uniprot (accession number P04386) and is shown below as SEQ ID No. 4.

GAL4 transcription factor
SEQ ID No. 4
MKLLSSIEQACDICRLKKLKCSKEKPKCAKCLKNNWECRYSPKTKRSPL

TRAHLTEVESRLERLEQLFLLIFPREDLDMILKMDSLQDIKALLTGLFV

-continued
QDNVNKDAVTDRLASVETDMPLTLRQHRISATSSSEESSNKGQRQLTVS

IDSAAHHDNSTIPLDFMPRDALHGFDWSEEDDMSDGLPFLKTDPNNNGF

FGDGSLLCILRSIGFKPENYTNSNVNRLPTMITDRYTLASRSTTSRLLQ

SYLNNFHPYCPIVHSPTLMMLYNNQIEIASKDQWQILFNCILAIGAWCI

EGESTDIDVFYYQNAKSHLTSKVFESGSIILVTALHLLSRYTQWRQKTN

TSYNFHSFSIRMAISLGLNRDLPSSFSDSSILEQRRRIWWSVYSWEIQL

SLLYGRSIQLSQNTISFPSSVDDVQRTTTGPTIYHGIIETARLLQVFTK

IYELDKTVTAEKSPICAKKCLMICNEIEEVSRQAPKFLQMDISTTALTN

LLKEHPWLSFTRFELKWKQLSLIIYVLRDFFTNFTQKKSQLEQDQNDHQ

SYEVKRCSIMLSDAAQRTVMSVSSYMDNHNVTPYFAWNCSYYLFNAVLV

PIKTLLSNSKSNAENNETAQLLQQINTVLMLLKKLATFKIQTCEKYIQV

LEEVCAPFLLSQCAIPLPHISYNNSNGSAIKNIVGSATIAQYPTLPEEN

VNNISVKYVSPGSVGPSPVPLKSGASFSDLVKLLSNRPPSRNSPVTIPR

STPSHRSVTPFLGQQQQLQSLVPLTPSALFGGANFNQSGNIADSSLSFT

FTNSSNGPNLITTQTNSQALSQPIASSNVHDNFMNNEITASKIDDGNNS

KPLSPGWTDQTAYNAFGITTGMFNTTTMDDVYNYLFDDEDTPPNPKKE

The Q system is derived from the qa gene cluster of *Neurospora* which is involved in the catabolism of quinic acid. The transcriptional activator QA-1F (QF) binds to regulatory sequences within the qa cluster and activates transcription in the absence of quinic acid.

The sequence of the transcriptional activator QF is available from Uniprot (accession number P11638) and its amino acid sequence is shown below as SEQ ID No. 5.

```
Amino acid sequence of quinic acid utilization
activator (QF)
                                       SEQ ID No. 5
MPPKRKTLNAAAEANAHADGHADGNADGHVANTAASSNNARFADLTNID

TPGLGPTTTTLLVEPARSKRQRVSRACDQCRAAREKCDGIQPACFPCVS

QGRSCTYQASPKKRGVQTGYIRTLELALAWMFENVARSEDALHNLLVRD

AGQGSALLVGKDSPAAERLHARWATSRVNKSITRLLSGQAAQDPSEDGQ

SPSEDINVQDAGAKTSDFPHAPHLTFSAPKSSTAETRTLPGPVRPPISA

NTLENNLQPDGTGIGKLPPNHWRLLDIYFSYTHSWLPILEKKDMYQALY

QYSEQGSLLPSANVESGVHAELWSALALASFQAAATAASSATGPASAAH

GHDNAINPSPADISDTARKLIPLESGPFQVQHCRALLLLCLVSLGRDDW

ESAWLLVGFAVRVLLVVRTQLPPDDDRPRPRMRALLVACFIVDTIVSMR

HNVPAHLKPDDIADLPLPEDGQDQWEPWTPCEGLGGEHTMLQMLRNPAY

PLSTFNHLYGVTKLVALELLPRIRTSSQNAPLEFRSRLQQVIGHNSPFS

VFVLSQDTASAFVPTAYLTRTVYLWAAAFSEPLNEHYSHLLIETLDQYQ

KRFGTYAIPPLIPSLLDSLLALKKQSHSSERHRRHLEELFPAYSSIWPR

GGRHSNTGLQPIRQLELPPTATATASIMPHVMEQPLSTSINPVNDRFNG

IPNPTPYNSDAALDAITQTNDYGSVNTHGILSTYPPPATHLNEASVALA

PGGAPPRPPPPYVDSTTNHPPYHSNLVPMANFGYSTVDYDAMVDDLASI

EYTDAVDVDPQFMTNLGFVPGCNFSDISTYEQ
```

Artifical Promoters Active in Immune Cells

Artificial promoters which function in human immune cells can be constructed by fusing the DNA-binding domain (of e.g. a prokaryotic DNA binding element) to the transactivation domain of another transcription factor functional in human immune cells. One such transactivation domain is that of herpes simplex virus virion protein 16 (VP16).

```
VP16 sequence
                                       SEQ ID 6
EFPGIRRPAGIPGDLAPPTDVSLGDELHLDGEDVAMAHADALDDFDLDMLG

DGDSPGPGFTPHDSAPYGALDMADFEFEQMFTDALGIDEYGG
```

The LexA/VP16 fusion is functional in human cells and its sequence is shown below as SEQ ID No. 7.

```
Amino acid sequence of LexA/VP16 fusion
                                       SEQ ID No. 7
MKALTARQQEVFDLIRDHISQTGMPPTRAEIAQRLGFRSPNAAEEHLKALA

RKGVIEIVSGASRGIRLLQEEEEGLPLVGRVAAGEPLLAQQHIEGHYQVDP

SLFKPNADFLLRVSGMSMKDIGIMDGDLLAVHKTQDVRNGQVVVARIDDEV

TVKRLKKQGNKVELLPENSEFKPIVVDLRQQSFTIEGLAVGVIRNGDWLEF

PGIRRPAGIPGDLAPPTDVSLGDELHLDGEDVAMAHADALDDFDLDMLGDG

DSPGPGFTPHDSAPYGALDMADFEFEQMFTDALGIDEYGG
```

The LacR/VP16 fusion protein is functional in human cells and its sequence is available and is shown below as SEQ ID No. 8.

```
Amino acid sequence of lactose repressor/VP16
fusion
                                       SEQ ID No. 8
MVNVKPVTLYDVAEYAGVSYQTVSRVVNQASHVSAKTREKVEAAMAELNYI

PNRVAQQLAGKQSLLIGVATSSLALHAPSQIVAAIKSRADQLGASVVVSMV

ERSGVEACKAAVHNLLAQRVSGLIINYPLDDQDAIAVEAACTNVPALFLDV

SDQTPINSIIFSHEDGTRLGVEHLVALGHQQIALLAGPLSSVSARLRLAGW

HKYLTRNQIQPIAEREGDWSAMSGFQQTMQMLNEGIVPTAMLVANDQMALG

AMRAITESGLRVGADISVVGYDDTEDSSCYIPPLTTIKQDFRLLGQTSVDR

LLQLSQGQAVKGNQLLPVSLVKRKTTLAPNTQTASPRALADSLMQLARQVS

RAPPTDVSLGDELHLDGEDVAMAHADALDDFDLDMLGDGDSPGPGFTPHDS

APYGALDMADFEFEQMFTDALGIDEYGG
```

The tetracycline-controlled transactivator (tTA) consists of a fusion between tetracycline repressor and the transactivation domain of herpes simplex virus virion protein 16 (VP16). The amino acid sequence of tTA is shown below as SEQ ID No. 9.

```
Amino acid sequence of tetracycline-controlled
transactivator (tTA)
                                       SEQ ID No. 9
MMSRLDKSKVINSALELLNEVGIEGLTTRKLAQKLGVEQPTLYWHVKNKRA

LLDALAIEMLDRHHTHFCPLEGESWQDFLRNNAKSFRCALLSHRDGAKVHL

GTRPTEKQYETLENQLAFLCQQGFSLENALYALSAVGHFTLGCVLEDQEHQ

VAKEERETPTTDSMPPLLRQAIELFDHQGAEPAFLFGLELIICGLEKQLKC
```

```
ESGSAYSRARTKNNYGSTIEGLLDLPDDDAPEEAGLAAPRLSFLPAGHTRR

LSTAPPTDVSLGDELHLDGEDVAMAHADALDDFDLDMLGDGDSPGPGFTPH

DSAPYGALDMADFEFEQMFTDALGIDEYGG
```

An artificial transcription factor can be created by fusing the DNA-binding domain of GAL4 to the transactivation domain of VP16.

The amino acid sequence of the GAL4/VP16 fusion protein is given below as SEQ ID No 10.

```
Amino acid sequence of GAL4/VP16
                                    SEQ ID No. 10
MKLLSSIEQACDICRLKKLKCSKEKPKCAKCLKNNWECRYSPKTKRSPLTR

AHLTEVESRLERLEQLFLLIFPREDLDMILKMDSLQDIKALLTGLFVQDNV

NKDAVTDRLASVETDMPLTLRQHRISATSSSEESSNKGQRQLTVSPEFPGI

WAPPTDVSLGDELHLDGEDVAMAHADALDDFDLDMLGDGDSPGPGFTPHDS

APYGALDMADFEFEQMFTDALGIDEYGG
```

The DNA-binding specificity of the transcriptional activator QF from *Neurospora* can be redirected to alternate sites by exchanging its DNA-binding domain for that of another transcription factor such as LexA.

The amino acid sequence of the LexA/QF artificial transcription factor is shown below as SEQ ID No. 11.

```
Amino acid sequence of LexA/QF fusion protein
                                    SEQ ID No. 11
MPPKKKRKVEDPMKALTARQQEVFDLIRDHISQTGMPPTRAEIAQRLGFRS

PNAAEEHLKALARKGVIEIVSGASRGIRLLQEEEEGLPLVGRVAAGEPLLA

QQHIEGHYQVDPSLFKPNADFLLRVSGMSMKDIGIMDGDLLAVHKTQDVRN

GQVVVARIDDEVTVKRLKKQGNKVELLPENSEFKPIVVDLRQQSFTIEGLA

VGVIRNGDWLGRQLELPPTATATASIMPHVMEQPLSTSINPVNDRFNGIPN

PTPYNSDAALDAITQTNDYGSVNTHGILSTYPPPATHLNEASVALAPGGAP

PRPPPPYVDSTTNHPPYHSNLVPMANFGYSTVDYDAMVDDLASIEYTDAVD

VDPQFMTNLGFVPGCNFSDINTYEQ
```

Non-Endogenous Transcription Factors

The transcription factor may be "non-endogenous" in the sense that it is not usually expressed in the cell type (i.e. an immune cell) which is transduced with the kit of vectors.

The transcription factor may be usually expressed in a non-immune cell.

The transcription factor may be derivable, for example, from neuronal cells or muscle cells.

Neuronal cell specific transcription factors include those that drive expression of the nestin promoter (see next section). The nestin promoter is driven by the POU family of transcription factors 1 and includes Brain-1 (Brn-1; also known as POU domain, class 3, transcription factor 3 [POU3F3]); and Brain-2 (Brn-2; also known as POU domain, class 3, transcription factor 2 [POU3F2]).

The DNA binding sequence of Brain-1 is 5'-ATTTGCAT-3' (SEQ ID No. 12). The amino acid sequence is available from Uniprot (P20264) and is shown as SEQ ID No. 13 below.

```
Brain-1 amino acid sequence
                                    SEQ ID No. 13
MATAASNPYLPGNSLLAAGSIVHSDAAGAGGGGGGGGGGGGAGGGGGM

QPGSAAVTSGAYRGDPSSVKMVQSDFMQGAMAASNGGHMLSHAHQWVTALP

HAAAAAAAAAAAAVEASSPWSGSAVGMAGSPQQPPQPPPPPPQGPDVKGGA

GRDDLHAGTALHHRGPPHLGPPPPPPHQGHPGGWGAAAAAAAAAAAAAAAA

HLPSMAGGQQPPPQSLLYSQPGGFTVNGMLSAPPGPGGGGGGAGGGAQSLV

HPGLVRGDTPELAEHHHHHHHHAHPHPPHPHHAQGPPHHGGGGGGAGPGLN

SHDPHSDEDTPTSDDLEQFAKQFKQRRIKLGFTQADVGLALGTLYGNVFSQ

TTICRFEALQLSFKNMCKLKPLLNKWLEEADSSTGSPTSIDKIAAQGRKRK

KRTSIEVSVKGALESHFLKCPKPSAQEITNLADSLQLEKEVVRVWFCNRRQ

KEKRMTPPGIQQQTPDDVYSQVGTVSADTPPPHHGLQTSVQ
```

The DNA binding sequence recognised by Brain-2 consists of two half sites (GCAT) and (TAAT), separated by a non-conserved spacer region of 0, 2, or 3 nucleotides. The amino acid sequence of Brain-2 is available from Uniprot (Accession Number: P20265) and is shown below as SEQ ID No. 14.

```
Brain-2 amino acid sequence
                                    SEQ ID No. 14
MATAASNHYSLLTSSASIVHAEPPGGMQQGAGGYREAQSLVQGDYGALQSN

GHPLSHAHQWITALSHGGGGGGGGGGGGGGGGGGGGDGSPWSTSPLGQPD

IKPSVVVQQGGRGDELHGPGALQQQHQQQQQQQQQQQQQQQQQQQQRPPH

LVHHAANHHPGPGAWRSAAAAAHLPPSMGASNGGLLYSQPSFTVNGMLGAG

GQPAGLHHHGLRDAHDEPHHADHHPHPHSHPHQQPPPPPPPQGPPGHPGAH

HDPHSDEDTPTSDDLEQFAKQFKQRRIKLGFTQADVGLALGTLYGNVFSQT

TICRFEALQLSFKNMCKLKPLLNKWLEEADSSSGSPTSIDKIAAQGRKRKK

RTSIEVSVKGALESHFLKCPKPSAQEITSLADSLQLEKEVVRVWFCNRRQK

EKRMTPPGGTLPGAEDVYGGSRDTPPHHGVQTPVQ
```

Other neuronal-cell specific transcription factors include those which drive transcription from the glial fibrillary acidic protein (GFAP) promoter (see next section). The GFAP promoter is regulated by several transcription factors, including nuclear factor 1C (NFIC) and 1X (NFIX).

The DNA binding site of NFIC is 5'-TTGGCXXXXXGC-CAA-3' (SEQ ID No. 15). The amino acid sequence of NFIC is available from Uniprot (Accession No. P08651) and is shown below as SEQ ID No. 16.

```
Human Nuclear factor 1 C amino acid sequence
                                    SEQ ID No. 16
MYSSPLCLTQDEFHPFIEALLPHVRAFAYTWFNLQARKRKYFKKHEKRMSK

DEERAVKDELLGEKPEVKQKWASRLLAKLRKDIRPECREDFVLSITGKKAP

GCVLSNPDQKGKMRRIDCLRQADKVWRLDLVMVILFKGIPLESTDGERLVK

AAQCGHPVLCVQPHHIGVAVKELDLYLAYFVRERDAEQSGSPRTGMGSDQE

DSKPITLDTTDFQESFVTSGVFSVTELIQVSRTPVVTGTGPNFSLGELQGH

LAYDLNPASTGLRRTLPSTSSSGSKRHKSGSMEEDVDTSPGGDYYTSPSSP

TSSSRNWTEDMEGGISSPVKKTEMDKSPFNSPSPQDSPRLSSFTQHHRPVI
```

-continued

AVHSGIARSPHPSSALHFPTTSILPQTASTYFPHTAIRYPPHLNPQDPLKD

LVSLACDPASQQPGPLNGSGQLKMPSHCLSAQMLAPPPPGLPRLALPPATK

PATTSEGGATSPTSPSYSPPDTSPANRSFVGLGPRDPAGIYQAQSWYLG

The DNA binding site of NFIC is 5'-TTGGCXXXXXGC-CAA-3' (SEQ ID No. 17). The amino acid sequence of NFIX is available from Uniprot (Accession No. Q14938) and is shown below as SEQ ID No. 18.

```
Human Nuclear factor 1X amino acid sequence
                                         SEQ ID No. 18
MYSPYCLTQDEFHPFIEALLPHVRAFSYTWFNLQARKRKYFKKHEKRMSKD

EERAVKDELLGEKPEIKQKWASRLLAKLRKDIRPEFREDFVLTITGKKPPC

CVLSNPDQKGKIRRIDCLRQADKVWRLDLVMVILFKGIPLESTDGERLYKS

PQCSNPGLCVQPHHIGVTIKELDLYLAYFVHTPESGQSDSSNQQGDADIKP

LPNGHLSFQDCFVTSGVWNVTELVRVSQTPVATASGPNFSLADLESPSYYN

INQVTLGRRSITSPPSTSTTKRPKSIDDSEMESPVDDVFYPGTGRSPAAGS

SQSSGWPNDVDAGPASLKKSGKLDFCSALSSQGSSPRMAFTHHPLPVLAGV

RPGSPRATASALHFPSTSIIQQSSPYFTHPTIRYHHHHGQDSLKEFVQFVC

SDGSGQATGQPNGSGQGKVPGSFLLPPPPPVARPVPLPMPDSKSTSTAPDG

AALTPPSPSFATTGASSANRFVSIGPRDGNFLNIPQQSQSWFL
```

Muscle cell specific transcription factors include those that drive expression from the myogenin (myog) promoter; the murine muscle creatine kinase promoter; or the muscle creatine kinase (MCK) promoter/α-myosin heavy chain enhancer hybrid (referred to as MHCK7). DNA-binding sites present in the myog, MCK and MHCK7 promoter regions include those for the transcription factors: myoblast determination protein 1 (MyoD1); myocyte-specific enhancer factor 2A (MEF2A) 5; and Krueppel-like factor 3 (KLF3) 7.

MyoD is the master regulator of muscle-specific genes and has been implicated in regulating the expression of 1,953 genes. MyoD binds to the promoter region of myogenin 5: the DNA binding site of MyoD is 5'-CANNTG-3' (SEQ ID No. 19). The amino acid sequence of human myoblast determination protein 1 (MyoD1) is available from Uniprot (Accession No. P15172) and is shown below as SEQ ID No. 20.

```
Human myoblast determination protein 1 (MyoD1)
amino acid sequence
                                         SEQ ID No. 20
MELLSPPLRDVDLTAPDGSLCSFATTDDFYDDPCFDSPDLRFFEDLDPRLM

HVGALLKPEEHSHFPAAVHPAPGAREDEHVRAPSGHHQAGRCLLWACKACK

RKTTNADRRKAATMRERRRLSKVNEAFETLKRCTSSNPNQRLPKVEILRNA

IRYIEGLQALLRDQDAAPPGAAAAFYAPGPLPPGRGGEHYSGDSDASSPRS

NCSDGMMDYSGPPSGARRRNCYEGAYYNEAPSEPRPGKSAAVSSLDCLSSI

VERISTESPAAPALLLADVPSESPPRRQEAAAPSEGESSGDPTQSPDAAPQ

CPAGANPNPIYQVL
```

Myocyte-specific enhancer factor 2A (MEF2A) binds not only to the myogenin promoter region, but also to the MCK promoter. The DNA binding site of MEF2A is 5'-YTA[AT]4TAR-3' (SEQ ID No. 21). The amino acid sequence for human myocyte-specific enhancer factor 2A (MEF2A) amino acid sequence is available from Uniprot (Accession No. Q02078) and is shown below as SEQ ID No. 22.

```
Human myocyte-specific enhancer factor 2A (MEF2A)
                                         SEQ ID No. 22
MGRKKIQITRIMDERNRQVTFTKRKFGLMKKAYELSVLCDCEIALIIFNSS

NKLFQYASTDMDKVLLKYTEYNEPHESRTNSDIVEALNKKEHRGCDSPDPD

TSYVLTPHTEEKYKKINEEFDNMMRNHKIAPGLPPQNFSMSVTVPVTSPNA

LSYTNPGSSLVSPSLAASSTLTDSSMLSPPQTTLHRNVSPGAPQRPPSTGN

AGGMLSTTDLTVPNGAGSSPVGNGFVNSRASPNLIGATGANSLGKVMPTKS

PPPPGGGNLGMNSRKPDLRVVIPPSSKGMMPPLSEEEELELNTQRISSSQA

TQPLATPVVSVTTPSLPPQGLVYSAMPTAYNTDYSLTSADLSALQGFNSPG

MLSLGQVSAWQQHHLGQAALSSLVAGGQLSQGSNLSINTNQNISIKSEPIS

PPRDRMTPSGFQQQQQQQQQQQPPPPPQPQPQPPQPQPRQEMGRSPVDSLS

SSSSSYDGSDREDPRGDFHSPIVLGRPPNTEDRESPSVKRMRMDAWV
```

KLF3 is a known positive regulator of the MCK promoter, and although KLF3 lacks a transactivation domain (TAD), it is thought to exert its regulatory function through its interaction with serum response factor (SRF), a ubiquitously expressed transcription factor. The DNA-binding site of KLF3 is 5'-C(A/C)CACCC-3' (SEQ ID No. 23). The amino acid sequence of human Krueppel-like factor 3 (KLF3) is available from Uniprot (Accession No. P57682) and is shown below as SEQ ID No. 24.

```
Human Krueppel-like factor 3 (KLF3) amino acid
sequence
                                         SEQ ID No. 24
MLMFDPVPVKQEAMDPVSVSYPSNYMESMKPNKYGVIYSTPLPEKFFQTPE

GLSHGIQMEPVDLTVNKRSSPPSAGNSPSSLKFPSSHRRASPGLSMPSSSP

PIKKYSPPSPGVQPFGVPLSMPPVMAAALSRHGIRSPGILPVIQPVVVQPV

PFMYTSHLQQPLMVSLSEEMENSSSSMQVPVIESYEKPISQKKIKIEPGIE

PQRTDYYPEEMSPPLMNSVSPPQALLQENHPSVIVQPGKRPLPVESPDTQR

KRRIHRCDYDGCNKVYTKSSHLKAHRRTHTGEKPYKCTWEGCTWKFARSDE

LTRHFRKHTGIKPFQCPDCDRSFSRSDHLALHRKRHMLV
```

Custom Zinc Finger-Based Artificial Transcription Factors

Artificial transcription factors can be constructed using zinc finger domains, which are short domain of approximately 30 amino acids that have a similar structure but vary in binding specificity. A single zinc finger domain is capable of recognising 3 base pairs of DNA and by splicing multiple zinc fingers together using amino acid linker sequences it is possible to generate a DNA-binding protein with a defined specificity. By fusing an array of zinc finger domains to a suitable transactivation domain (e.g. VP16), it is possible to construct an artificial transcription factor capable of recognising a pre-defined DNA sequence present in an artificial upstream activating sequence (UAS).

Custom TaL-Based Artificial Transcriptional Factors

Transcription activation-like (TAL) effectors are programmable transcription factors that offer the ability to construct artificial promoters. A TAL effector comprises a central repeat region of a variable number of 34 amino acid repeats, two C-terminal nuclear localisation sequences and a C-terminal transactivation domain 21. The repeat region dictates the DNA-binding specificity of the TAL effector, with each repeat recognising a single base pair of DNA (meaning that the number of repeats in the TAL effector defines how many base pairs it will recognise) and hyper-variability in residues 12 and 13 of the 34 amino acid determines which nucleotide it will recognise. As the DNA-binding specificity of TAL effectors is programmable, it is possible to construct artificial transcription factors recognising cognate DNA sequences in promoter regions by fusion with an appropriate transcription factor.

CRISPR-Based Artificial Transcriptional Factors

Many bacteria possess an adaptive immune system that protects them from invading bacteriophages. This system is encoded on a locus comprising an array of clustered regularly interspaced short palindromic repeat (CRISPR) sequences and associated proteins (Cas proteins) that are involved in processing and utilising RNA transcribed from the CRISPR array to recognise and cleave the DNA of invading viruses. Cleavage of the viral DNA is carried out by the endonuclease Cas9, which is guided to a specific site in the viral genome by an RNA derived from the CRISPR array.

As Cas9 is targeted to a specific DNA sequence via a guide RNA (gRNA), which can be easily synthesized in vitro or in vivo, the CRISPR/Cas9 system can be repurposed for modifying genomic DNA sequences in eukaryotes. Further adaptations of the CRISPR/Cas9 system, by rendering Cas9 catalytically inactive and coupling it to either a transcriptional activator or repressor, have enabled its use in controlling gene expression.

Systems utilising catalytically inactive Cas9 (dCas9) coupled to a transactivation domain (TAD), such as VP16, have been described to drive the expression of endogenous genes in yeast and human cells. These systems can be easily adapted to generate artificial transcriptional circuits using defined promoter sequences and complementary RNAs to guide the dCas9/TAD fusion protein to them and initiate gene transcription.

The amino acid sequence of dCas9/VP64 is shown below as SEQ ID No. 25. In this sequence, the large T-antigen (Uniprot; P0307) SV40 nuclear localization sequences are shown in bold; the linker sequence is in italics; and the VP64 transactivation domain is underlined.

dCas9/VP64
SEQ ID No. 25
MKKKRKVEASDKKYSIGLAIGTNSVGWAVITDEYKVPSKKFKVLGNTDRHS

IKKNLIGALLFDSGETAEATRLKRTARRRYTRRKNRICYLQEIFSNEMAKV

DDSFFHRLEESFLVEEDKKHERHPIFGNIVDEVAYHEKYPTIHLRKKLVDS

TDKADLRLIYLALAHMIKFRGHFLIEGDLNPDNSDVDKLFIQLVQTYNQLF

EENPINASGVDAKAILSARLSKSRRLENLIAQLPGEKKNGLFGNLIALSLG

LTPNFKSNFDLAEDAKLQLSKDTYDDDLDNLLAQIGDQYADLFLAAKNLSD

AILLSDILRVNTEITKAPLSASMIKRYDEHHQDLTLLKALVRQQLPEKYKE

IFFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKNL

PNEKVLPKHSLLYEYFTVYNELTKVKYVTEGMRKPAFLSGEQKKAIVDLLF

KTNRKVTVKQLKEDYFKKIECFDSVEISGVEDRFNASLGTYHDLLKIIKDK

-continued
DFLDNEENEDILEDIVLTLTLFEDREMIEERLKTYAHLFDDKVMKQLKRRR

YTGWGRLSRKLINGIRDKQSGKTILDFLKSDGFANRNFMQLIHDDSLTFKE

DIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQN

EKLYLYYLQNGRDMYVDQELDINRLSDYDVDAIVPQSFLKDDSIDNKVLTR

SDKNRGKSDNVPSEEVVKKMKNYWRQLLNAKLITQRKFDNLTKAERGGLSE

LDKAGFIKRQLVETRQITKHVAQILDSRMNTKYDENDKLIREVKVITLKSK

LVSDFRKDFQFYKVREINNYHHAHDAYLNAVVGTALIKKYPKLESEFVYGD

YKVYDVRKMIAKSEQEIGKATAKYFFYSNIMNFFKTEITLANGEIRKRPLI

ETNGETGEIVWDKGRDFATVRKVLSMPQVNIVKKTEVQTGGFSKESILPKR

NSDKLIARKKDWDPKKYGGFDSPTVAYSVLVVAKVEKGKSKKLKSVKELLG

ITIMERSSFEKNPIDFLEAKGYKEVKKDLIIKLPKYSLFELENGRKRMLAS

AGELQKGNELALPSKYVNFLYLASHYEKLKGSPEDNEQKQLFVEQHKHYLD

EIIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD

PKKKRKV<i>DALDDFDLDMLGS</i>DALDDFDLDMLGSDALDDFDLDMLGSDALDD

FDLDMLYID

The first cassette in the transcriptional circuit may express the dCas9/TAD fusion protein and contain a U6 promoter driving the transcription of a gRNA targeting the artificial promoter region in the second cassette of the transcriptional circuit. Candidate promoter regions that can be used to drive expression of the second cassette include a tissue-specific promoter, such as the MHCK7 hybrid promoter described below, or an artificial transcriptional circuit based on the GAL4 UAS, TetR, and LacI promoters, which have been employed previously in eukaryotes to control the expression of exogenous genes.

Alternatively, an entirely artificial promoter sequence that does not share homology with any other sequence in the human genome can be constructed. The gRNAs required to target the Cas9/TAD fusion to the artificial promoter regions can be designed using freely available design tools such as CRISPOR (http://crispor.tefor.net/) to ensure that they do not exhibit off-targeting and initiate unwanted expression of endogenous genes. The expression of both dCas9/TAD and the gRNA from the first retroviral cassette then drives transcription from the artificial promoter in the second cassette.

Promoters

Eukaryotic expression cassettes use promoter sequences to drive transgene expression. Promoter sequences function by their recognition by transcription factors which upon binding to the promoter sequences initiation transcription by engaging RNA polymerase to the transcriptional start site.

The vector may comprise a constitutively active promoter, such as the immediate early cytomegalovirus (CMV) promoter sequence, the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, or a human gene promoter such as the actin promoter, the myosin promoter, the elongation factor-Ia promoter, the hemoglobin promoter, or the creatine kinase promoter.

Alternatively, the vector may comprise an inducible promoter. The use of an inducible promoter provides a molecular switch capable of turning on expression of the polynucleotide sequence to which it is operatively linked when expression is desired, or turning off the expression when expression is not desired. Examples of inducible promoters include a metallothionine promoter, a glucocorticoid promoter, a progesterone promoter, and a tetracycline-regulated promoter.

Alternatively, the promoter may only be active in the presence of a transcription factor provided by another vector.

The promoter sequence may be activated by an artificial transcription factor. The promoter sequence may be activated by an artificial transcription factor which comprises a guide RNA. The transcription factor may, for example, comprise the RNA-guided endonuclease Cas9 (dCas9) fused to a transcription activation domain (TAD) (see previous section).

Candidate promoter regions that can be used to drive expression of the second vector include a tissue-specific promoter, such as the MHCK7 hybrid promoter described below, or an artificial transcriptional circuit based on the GAL4 upstream activation sequence, TetR, and/or LacI promoters, which have been employed in eukaryotes to control the expression of exogenous genes. Alternatively, an entirely artificial promoter sequence that does not share homology with any other sequence in the human genome can be constructed.

The nucleic acid sequence of a 5-repeat GAL4 upstream activating sequence is shown as SEQ ID No. 26. In this sequence, GAL4 DNA binding sequences (5'-CGG-N11-CCG-3'-SEQ ID No. 46) are underlined.

```
GAL4 5x upstream activating sequence
                                              SEQ ID No. 26
CGGAGTACTGTCCTCCGAGSCGGAGTACTGTCCTCCGACTCGAGCGGAGTA

CTGTCCTCCGATCGGAGTACTGTCCTCCGCGAATTCCGGAGTACTGTCCTC

CG
```

The Tet response element comprises seven repeats of the tetracycline operator (tetO) sequence. The nucleic acid sequence of the Tet response element (TRE) is shown below as SEQ ID No. 27. In this sequence, tetO sequences are underlined.

```
Tet response element (TRE)
                                              SEQ ID No. 27
TCCCTATCAGTGATAGAGAAAAGTGAAAGTCGAGTTTACCACTCCCTATC

AGTGATAGAGAAAAGTGAAAGTCGAGTTTACCACTCCCTATCAGTGATAG

AGAAAAGTGAAAGTCGAGTTTACCACTCCCTATCAGTGATAGAGAAAAGT

GAAAGTCGAGTTTACCACTCCCTATCAGTGATAGAGAAAAGTGAAAGTCG

AGTTTACCACTCCCTATCAGTGATAGAGAAAAGTGAAAGTCGAGTTTACC

ACTCCCTATCAGTGATAGAGA
```

The nucleic acid sequence of the LacI promoter sequence is shown below as SEQ ID No. 28.

```
LacI promoter sequence
                                              SEQ ID No. 28
GACACCATCGAATGGCGCAAAACCTTTCGCGGTATGGCATGATAGCGCCC

GGAAGAGAGTCAATTCAGGGTGGTGAAT
```

The promotor sequence may be an artificial promoter sequence designed to be recognised by an artificial transcription factor such as transcription activation-like (TAL) effector (see previous section).

TAL effectors are programmable transcription factors that offer the ability to construct artificial promoters. As the DNA-binding specificity of TAL effectors is programmable, it is possible to construct artificial transcription factors recognising cognate DNA sequences in promoter regions. It is also possible to construct artificial promoter sequences for use with known or artificial transcription factors using the TAL effector technology.

The promoter sequence may be from a natural gene, for example from a prokaryotic or eukaryotic organism. Where the promoter is derived from a human gene, in order to avoid background transcription, the promoter may be activated by a "non-endogenous" transcription factor, i.e. a transcription factor which is not usually expressed in the host cell type. The promoter sequence may be "non-endogenous" in the sense that it is derived from a gene which is not normally expressed in the host cell. The promoter sequence may be derived from a gene which is usually expressed in a non-immune cell. The promoter sequence may be tissue-specific for non-immune tissue. Potential tissue-specific promoters include those controlling the expression of muscle-specific or neuronal-specific genes.

Neuronal-Specific Promoters

Nestin is an intermediate-filament protein that is expressed by stem cells during neurogenesis and is down-regulated as the cells differentiate into neurons.

The promoter region derived from intron 2 of the nestin gene has been widely used to drive transgene expression in conditional knock-out and knock-in mouse models. Expression of the nestin promoter is driven by the POU family of transcription factors (see above). The nucleic acid sequence of Murine nestin intron 2 is available from GenBank (Accession No. AY438043.1) and is shown below as SEQ ID No. 29.

```
Murine nestin intron 2
                                              SEQ ID No. 29
GGTCTGAAAAGGATTTGGAGAAGGGGAGCTGAATTCATTTGCTTTTGTCT

GTTACCAGCTCTGGGGGCAGAGAGAGAGCCATCCCCTGGGAACAGCCTGA

GAATTCCCACTTCCCCTGAGGAGCCCTCCCTTCTTAGGCCCTCCAGATGG

TAGTGTGGACAAAAGGCAATAATTAGCATGAGAATCGGCCTCCCTCCCAG

AGGATGAGGTCATCGGCCTTGGCCTTGGGTGGGGAGGCGGAGACTGATCT

GAGGAGT
```

Glial fibrillary acidic protein (GFAP) is an intermediate filament protein whose expression is restricted to astrocytes. The promoter region of GFAP has been used to drive the expression of transgenes in mouse models and is a suitable promoter to form part of a transcriptional circuit. The GFAP promoter is regulated by several transcription factors, including nuclear factor 1C (NFIC) and 1X (NFIX), as mentioned above. The nucleic acid sequence for the GFAP promoter is shown below as SEQ Id No. 30.

```
Glial Fibrillary Acidic Protein (GFAP) Promoter
sequence
                                              SEQ ID No. 30
ACATATCCTGGTGTGGAGTAGGGGACGCTGCTCTGACAGAGGCTCGGGGG

CCTGAGCTGGCTCTGTGAGCTGGGGAGGAGGCAGACAGCCAGGCCTTGTC
```

```
-continued
TGCAAGCAGACCTGGCAGCATTGGGCTGGCCGCCCCCCAGGGCCTCCTCT

TCATGCCCAGTGAATGACTCACCTTGGCACAGACACAATGTTCGGGGTGG

GCACAGTGCCTGCTTCCCGCCGCACCCCAGCCCCCCTCAAATGCCTTCCG

AGAAGCCCATTGAGCAGGGAGCTCTCCCCATAGCTGGGCTGCGGCCCAAC

CCCACCCCCTCAGGCTATGCCAGGGGGTGTTGCCAGGGGCACCCGGGCAT

CGCCAGTCTAGCCCACTCCTTCATAAAGCCCTCGCATCCCAGGAGCGAGC

AGAGCCAGAGCAGGTTGGAGAGGAGACGCATCACCTCCGCTGCTCGCGGG

GATCCTCTAGAGTCGACGGATCCGGGGAATTCCCCAGTCTCAGGATCCAC

CATGGGG
```

A transcriptional circuit can be constructed by placing a transgene encoding a neuronal specific transcription factor on the first cassette and its cognate promote sequence on the second cassette to drive transgene expression.

Muscle-Specific Promoter Regions

Several muscle-specific promoters are suitable for use in driving the expression of the genes encoded on the second cassette, and include the myogenin (myog) promoter, murine muscle creatine kinase promoter, and the muscle creatine kinase (MCK) promoter/α-myosin heavy chain enhancer hybrid (referred to as MHCK7). The latter promoter exhibits low expression in non-muscle cells and has been shown to be inactive in dendritic cell lines. The muscle-specific promoter regions possess binding sites for transcription factors, which function in a co-ordinated manner to drive gene transcription. DNA-binding sites present in the myog, MCK and MHCK7 promoter regions include those for the transcription factors myoblast determination protein 1 (MyoD1), myocyte-specific enhancer factor 2A (MEF2A) 5 and Krueppel-like factor 3 (KLF3) 7 (see previous section).

A transcription circuit can be built by placing a muscle-specific transcription factor (MyoD, MEF2 or KLF3) on the first cassette and a compatible promoter region (myogenin, MCK or MHCK7) on the second cassette to drive expression of the transgenes encoded on it.

The nucleic acid sequence of murine myogenin promoter sequence is available from GenBank (Accession No. X71910.1) and is shown as SEQ ID No. 31

```
murine myogenin promoter
                                    SEQ ID No. 31
ATCCACTGGAAACGTCTTGATGTGCAGCAACAGCTTAGAGGGGGGCTCAG

GTTTCTGTGGCGTTGGCTATATTTATCTCTGGGTTCATGCCAGCAGGGAG

GGTTTAAATGGCACCCAGCAGTTGGTGTGAGGGGCTGCGGGAGCTTGGGG

G
```

The nucleic acid sequence of murine muscle creatine kinase promoter is available from GenBank (Accession No AF188002.1) and is shown below as SEQ ID No. 32.

```
murine muscle creatine kinase promoter
                                    SEQ ID No. 32
CCACTACGGGTCTAGGCTGCCCATGTAAGGAGGCAAGGCCTGGGGACACC

CGAGATGCCTGGTTATAATTAACCCAGACATGTGGCTGCCCCCCCCCCCC

CAACACCTGCTGCCTCTAAAAATAACCCTGTCCCTGGTGGAT
```

The nucleic acid sequences of murine muscle creatine kinase and α-myosin heavy chain (MHCK7) promoter are available from GenBank (Accession numbers AF188002.1 and U71441.1 respectively). The combined sequence is shown below as SEQ ID No. 33, in which the murine α-myosin heavy chain enhancer sequence is in normal text and the murine muscle creatine kinase promoter region is underlined.

```
Murine muscle creatine kinase/α-myosin heavy chain
(MHCK7) promoter
                                    SEQ ID No. 33
CCTTCAGATTAAAAATAACTGAGGTAAGGGCCTGGGTAGGGGAGGTGGTG

TGAGACGCTCCTGTCTCTCCTCTATCTGCCCATCGGCCCTTTGGGGAGGA

GGAATGTGCCCAAGGACTAAAAAAAGGCCATGGAGCCAGAGGGGCGAGGG

CAACAGACCTTTCATGGGCAAACCTTGGGGCCCTGCTGTCTAGCATGCCC

CACTACGGGTCTAGGCTGCCCATGTAAGGAGGCAAGGCCTGGGGACACCC

GAGATGCCTGGTTATAATTAACCCAGACATGTGGCTGCCCCCCCCCCCC

AACACCTGCTGCCTCTAAAAATAACCCTGTCCCTGGTGGATCCCCTGCAT

GCGAAGATCTTCGAACAAGGCTGTGGGGGACTGAGGGCAGGCTGTAACAG

GCTTGGGGGCCAGGGCTTATACGTGCCTGGGACTCCCAAAGTATTACTGT

TCCATGTTCCCGGCGAAGGGCCAGCTGTCCCCGCCAGCTAGACTCAGCA

CTTAGTTTAGGAACCAGTGAGCAAGTCAGCCCTTGGGGCAGCCCATACAA

GGCCATGGGGCTGGGCAAGCTGCACGCCTGGGTCCGGGGTGGGCACGGTG

CCCGGGCAACGAGCTGAAAGCTCATCTGCTCTCAGGGGCCCCTCCCTGGG

GACAGCCCCTCCTGGCTAGTCACACCCTGTAGGCTCCTCTATATAACCCA

GGGGCACAGGGGCTGCCCTCATTCTACCACCACCTCCACAGCACAGACAG

ACACTCAGGAGCCAGCCAGCC
```

Cassettes

The vectors in the kit of the present invention comprise a combination of genetic elements in the form of a cassette.

The first vector in the kit of vectors of the invention comprises a first transgene and a nucleotide sequence encoding a transcription factor.

The first vector may comprise a cassette having the general structure:

TG1-coexpr-TF or
TF-coexpr-TG1 in which:

TG1 is a first transgene

Coexpr is a nucleotide sequence enabling co-expression of the two flanking polypeptides (in this case TF and the polypeptide encoded by TG1)

TF is a nucleotide sequence encoding the transcription factor

The second vector in the kit of vectors of the invention comprises a second transgene under the control of a promoter which is activated by the transcription factor.

The second vector may comprise a cassette having the general structure:

pT-TG2 in which pT is a promoter activated by the transcription factor; and

TG2 is a second transgene.

Figure 1:
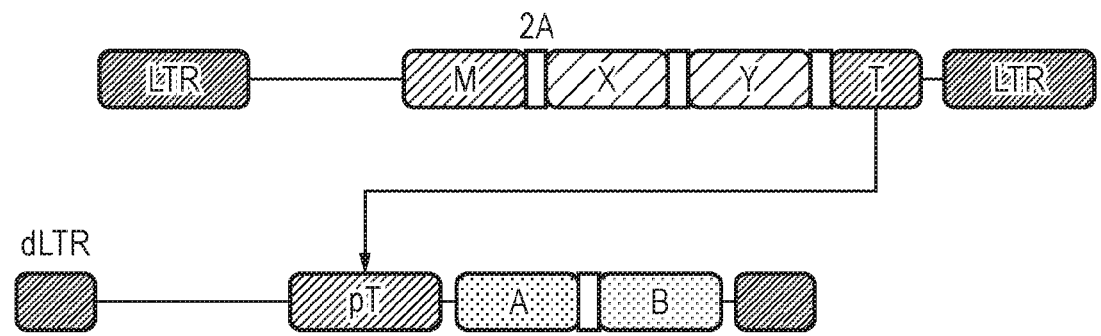
FIG. 1—A schematic diagram illustrating kit of vectors with a marked primary cassette and a dependent secondary cassette In this scenario, a primary cassette is driven by a constitutively active promoter and encodes a primary transgenic element (transgenes X and Y separated by a 2A peptide) and a transcription factor (T). A secondary cassette is driven by a promoter sequence (pT) dependent on the transcription factor supplied by the primary cassette. The secondary cassette encodes ancillary transgenes A and B. The primary cassette also encodes a marker gene (M), so that cells which do not contain the primary cassette, and therefore do not express transgenes, can be removed.

FIG. 1 illustrates an arrangement having a first vector with a marked primary cassette and second vector with a dependent secondary cassette. The primary cassette is driven by a constitutively active promoter and comprises a marker gene, a first transgene and a nucleotide sequence encoding a transcription factor. The secondary cassette is driven by a promoter sequence dependent on the transcription factor supplied by the primary cassette and comprises a second transgene. In this setup, after double-transduction the culture could contain immune cells which have not been transduced by the primary cassette and hence express no transgenes or immune cells which express the primary cassette only, or immune cells which express the primary and secondary cassettes. If the primary cassette also encodes for a marker gene, cells can be selected so that immune cells which do not express transgenes are removed.

The primary cassette for this arrangement may comprise one the following general structures:

M-coexpr-TG1-coexpr-TF
M-coexpr-TF-coexpr-TG1
TG1-coexpr-M-coexpr-TF
TG1-coexpr-TF-coexpr-M
TF-coexpr-M-coexpr-TG1
TF-coexpr-TG1-coexpr-M In which:

M is a marker gene and coexpr, TG1 and TF are as defined above. The secondary cassette for this arrangement may comprise the structure pT-TG2, as defined above.

Figure 3:
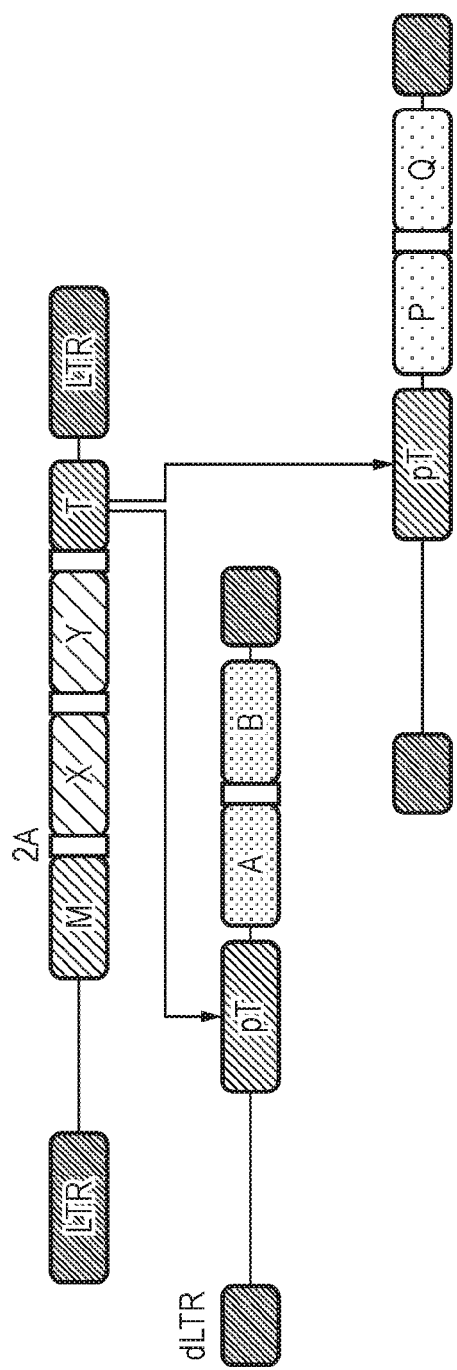
FIG. 3—A schematic diagram illustrating kit of vectors with a primary cassette and multiple dependent cassettes In this scenario, a primary cassette is driven by a constitutively active promoter and encodes a primary transgenic element (transgenes X and Y separated by a 2A peptide) and a transcription factor (T). A secondary cassette is driven by a promoter sequence (pT) dependent on the transcription factor supplied by the primary cassette. The secondary cassette encodes ancillary transgenes A and B. A tertiary cassette is also driven by a promoter sequence (pT) dependent on the transcription factor and encodes ancillary transgenes P and Q. The primary cassette also encodes a marker gene (M), so that cells which do not contain the primary cassette, and therefore do not express transgenes, can be removed.

FIG. 3 illustrates a similar scenario, but one in which there are multiple dependent cassettes. In this the third cassette may have the general formula pT-TG3, in which TG3 is a third transgene and pT is as defined above.

Figure 2:
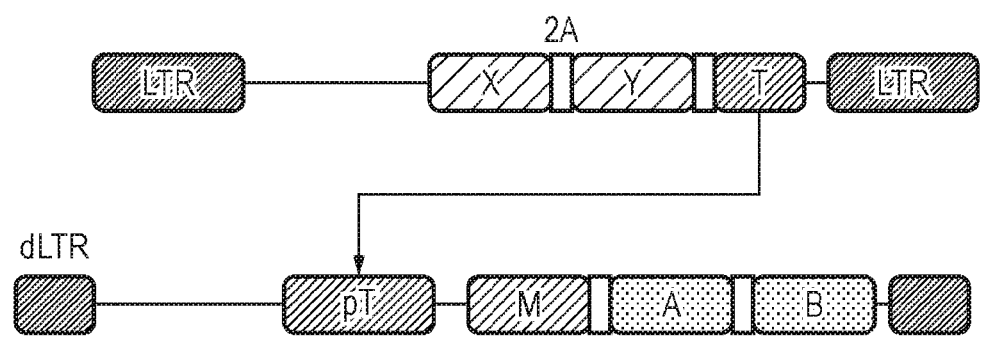
FIG. 2—A schematic diagram illustrating kit of vectors with a primary cassette and a dependent marked secondary cassette In this scenario, a primary cassette is driven by a constitutively active promoter and encodes a primary transgenic element (transgenes X and Y separated by a 2A peptide) and a transcription factor (T). A secondary cassette is driven by a promoter sequence (pT) dependent on the transcription factor supplied by the primary cassette. The secondary cassette encodes ancillary transgenes A and B. The secondary cassette also encodes a marker gene, so that sorting on the marker gene results in the selection of cells expressing both the primary and secondary cassettes only.

FIG. 2 illustrates an arrangement having a first vector with a primary cassette and second vector with a marked dependent secondary cassette. The primary cassette is driven by a constitutively active promoter and comprises a first transgene and a nucleotide sequence encoding a transcription factor. The secondary cassette is driven by a promoter sequence dependent on the transcription factor supplied by the primary cassette and comprises a marker gene and a second transgene. In this setup, after transduction with both vectors, the culture will contain immune cells which express neither cassette, the primary cassette only or the primary and secondary cassette. In this case sorting on the marker gene which is expressed in the secondary cassette results in the selection of double-expressing cells only.

The first vector may comprise a cassette having the general structure as defined above:

TG1-coexpr-TF or
TF-coexpr-TG1

The second vector may comprise a cassette having the general structure:

pT-TG2-coexpr-M or
pT-M-coexpr-TG2 in which pT, TG2, coexpr and M are as defined above.

Figure 4:
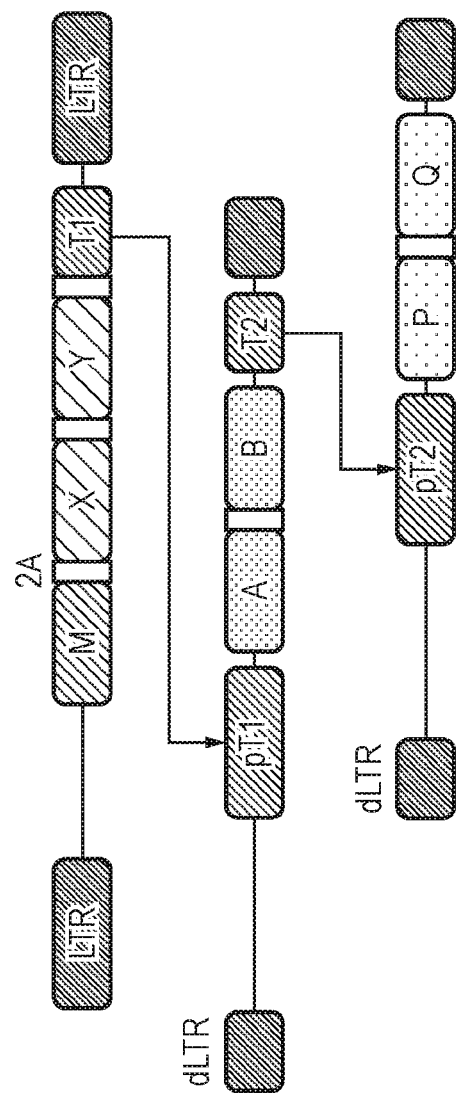
FIG. 4—A schematic diagram illustrating kit of vectors with a primary cassette and iterative dependent cassettes In this scenario, a primary cassette is driven by a constitutively active promoter and encodes a primary transgenic element (transgenes X and Y separated by a 2A peptide) and a transcription factor (T). A secondary cassette is driven by a promoter sequence (pT1) dependent on the transcription factor supplied by the primary cassette. The secondary cassette encodes ancillary transgenes A and B. A tertiary cassette is driven by a promoter sequence (pT2) dependent on the transcription factor supplied by the secondary cassette. The secondary cassette encodes ancillary transgenes P and Q. In this scenario, an iterative dependence of expression is required down the chains of expression cassettes. If a marker is expressed by the last expression cassette, sorting will select cells which express all cassettes.

FIG. 4 illustrates an arrangement having three or more vectors with iterative dependent cassettes. The primary cassette is driven by a constitutively active promoter and comprises a marker gene, a first transgene and a nucleotide sequence encoding a first transcription factor. The second cassette is driven by a promoter sequence dependent on the first transcription factor supplied by the primary cassette and comprises a second transgene and a nucleotide sequence encoding a second transcription factor. The tertiary cassette is driven by a promoter sequence dependent on the second transcription factor supplied by the secondary cassette and comprises a third transgene. In this scenario, an iterative dependence of expression is required down the chains of expression cassettes. If a marker is expressed by the last expression cassette, sorting will select cells which express all cassettes.

The primary cassette may have a general structure as described above for the arrangement shown in FIG. 1. The secondary cassette may have the general structure:

pT1-TG2-coexpr-TF2, or
pT1-TF2-coexpr-TG2 in which pT1 is a promoter activated by the first transcription factor, TF2 is a nucleotide sequence encoding the second transcription factor and TG2 and coexpr are as defined above.

The tertiary cassette may have the general structure:

pT2-TG3 in which pT2 is a promoter activated by the second transcription factor and TG3 is a third transgene.

Figure 5:
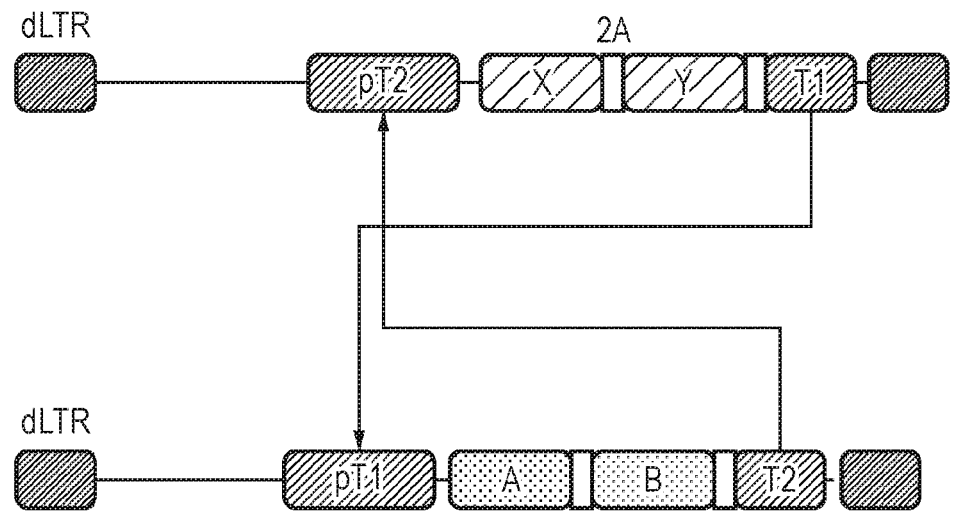
FIG. 5—A schematic diagram illustrating kit of vectors with circular dependent cassettes In this scenario, a primary cassette is driven by a promoter sequence (pT2) dependent on a transcription factor supplied by the secondary cassette. The primary cassette encodes transgenes X and Y separated by a 2A peptide and a first transcription factor (T1). A secondary cassette is driven by a promoter sequence (pT1) dependent on the transcription factor supplied by the primary cassette. The secondary cassette encodes ancillary transgenes A and B and a second transcription factor (T2). In this case if cells are transduced with only one of the two cassettes, expression is silent. If a cell is transduced with both cassettes, a small leak of expression present in all such systems would be amplified such that both cassettes are expressed.

FIG. 5 illustrates an arrangement having a two or more vectors with circular dependent cassettes. The primary cassette comprises a first transgene and is driven by a promoter sequence dependent on a second transcription factor supplied by the second cassette The secondary cassette comprises a second transgene and is driven by a promoter sequence dependent on a first transcription factor supplied by the first cassette. The two cassettes are therefore interdependent i.e. the expression from one is dependent on a transcription factor expressed by the other and vice versa. In this case, if cells are transduced with only one cassette, expression is silent. If a cell is transduced with both cassettes, a small leak of expression present in all such systems is be amplified such that both cassettes would be expressed.

Transgene

In the kit of vectors of the present invention, one or more vectors may express a transgene, i.e. a nucleotide sequence which transcribes or encodes an entity of interest (EOI).

The kit of vectors is for transducing an immune cell with multiple transgenes. The term "multiple" means two or more, as the kit of vectors comprise at least a first and a second transgene. The kit may include 3, 4, 5, 6, 7 or more transgenes. The transgene may be split between first and second and/or further vectors. A vector may express multiple transgenes by using a co-expression sequence such as an IRES or a self-cleaving peptide (see below).

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Transgenes or nucleic acids according to the invention may comprise DNA or RNA. They may be single-stranded or double-stranded. They may also be polynucleotides which include within them synthetic or modified nucleotides.

The transgene may encode a marker protein or it may enable selection of transduced cells for example by providing an antibiotic or drug-resistance gene to the cell.

The transgene may encode an activatory or inhibitory chimeric antigen receptor (CAR) or a T cell receptor (TCR).

The transgene may encode a signal transduction modifying protein.

The transgene may enhance proliferation, engraftment and/or survival of immune cells. For example, the transgene may encode a cytokine, cytokine receptor, chimeric cytokine receptor, dominant-negative SHP-1 or SHP-2, dominant negative TGFbeta of TGFbeta receptor, or a constitutively active or inducible JAK or STAT (see below).

The transgene may or allow pharmacological control of a CAR or TCR. For example, it may encode a signalling component for use in an inducible or disruptible CAR system, or encode a dampener of T-cell mediated signalling.

The transgene may encode a suicide switch.

When two vectors A and B are transduced into a cell, there are four possible outcomes:
a) no successful transduction with A or B
b) transduction with A but not B
c) transduction with B but not A
d) transduction with A and B A kit of vectors of the invention may comprise:
(i) a first vector which comprises a first transgene under the control of a constitutively active promoter and a nucleotide sequence encoding a transcription factor and; and
(ii) a second vector which comprises a second transgene under the control of a promoter dependent on the transcription factor supplied by the first vector.

In this case, transduction with the first vector alone will result in expression of the first transgene by the cell, however transduction with the second vector alone will not result in expression of the second transgene alone. In this system it is not possible to get expression of the second transgene without expression of the first transgene.

This is useful in situations where a CAR or TCR is co-expressed with an auxiliary gene, for example a gene which affects the activity of the CAR/TCR or the CAR/TCR expressing cell, and where it is derirable to avoid expression of the auxiliary gene without the CAR/TCR.

In this embodiment, the "first transgene", produced by the first vector and under the control of a constitutively active promoter, may encode a CAR or TCR; and the "second transgene", produced by the second vector and under the control of a promoter dependent on the transcription factor supplied by the first vector, may encode a factor which affects the activity of the CAR/TCR or the CAR/TCR expressing cell.

The second transgene may, for example, encode a cytokine, a cytokine receptor, a dominant negative TGF beta or TGF beta receptor, a signal transduction modifying protein, constitutively active JAK/STAT, an inhibitor CAR, a suicide switch or a dampener (see below).

The second vector may also comprise a marker gene. Expression of the marker gene indictates successful transduction with both the first and second vector (or first, second and third vectors).

Marker

One or more of the vectors in the kit may comprise a marker gene, which makes a cell expressing the gene detectable or selectable. It allows for identification of successful transduction.

For example, a marker gene may encode a marker protein which is detectable by cell surface expression or another property such as fluorescence or radio-labelling.

A marker protein may be derivable from CD34. CD34 is a cell surface glycoprotein and functions as a cell-cell adhesion factor. It also mediates the attachment of stem cells to bone marrow extracellular matrix or directly to stromal cells.

CD34 is not expressed by terminally differentiated haematopoietic lineages, so it is an ideal marker for modified T-cells.

CD34-expressing cells may be readily identified and isolated using the Miltenyi CliniMACS magnetic cell selection system, which is a commonly used reagent for clinical stem cell isolation. The CliniMACS CD34 selection system utilises the QBEnd10 monoclonal antibody to achieve cellular selection.

The QBEnd10-binding epitope from within the CD34 antigen has the amino acid sequence shown as SEQ ID No. 34.

(SEQ ID No. 34)
ELPTQGTFSNVSTNVS

The marker protein may comprise SEQ ID No. 34.

A compact sort-suicide gene comprising the QBEnd10-binding epitope is described in WO2013/153391.

Another example of a marker protein is a truncated version of the epidermal growth factor receptor (tEGFR) that lacks the EGF binding and intracellular signaling domains. Cell surface tEGFR can be detected by biotnylated anti-EGFR (Erbitux) monoclonal antibodies.

Various antibiotic resistance genes have been described which are useful markers for transduction. For example, the bacterial neomycin and hygromycin phosphotransferase genes confer resistance to G418 and hygromycin, respectively; a mutant mouse dihydrofolate reductase gene (dhfr*) confers resistance to methotrexate; the bacterial gpt gene which cells to grow in medium containing mycophenolic acid, xanthine, and aminopterin; the bacterial hisD gene which allows cells to grow in medium without histidine but containing histidinol; the multidrug resistance gene (mdr) which confers resistance to a variety of drugs; and the bacterial genes which confer resistance to puromycin or phleomycin.

Chimeric Antigen Receptor (CAR)

One or more of the vector(s) of the kit of the invention may comprise a transgene encoding a chimeric antigen receptor (CAR).

A classical CAR is a chimeric type I trans-membrane protein which connects an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain.

A CAR may have the general formula:

Signal peptide—antigen binding domain—spacer domain—transmembrane domain—intracellular T cell signaling domain (endodomain).

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain may comprise a domain which is not based on the antigen binding site of an antibody. For example the antigen binding domain may comprise a domain based on a protein/peptide which is a soluble ligand for a tumour cell surface receptor (e.g. a soluble peptide such as a cytokine or a chemokine); or an extracellular domain of a membrane anchored ligand or a receptor for which the binding pair counterpart is expressed on the tumour cell. The antigen binding domain may be based on a natural ligand of the antigen.

The antigen binding domain may comprise an affinity peptide from a combinatorial library or a de novo designed affinity protein/peptide.

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

The transmembrane domain is the portion of the CAR which spans the membrane. The transmembrane domain may be any protein structure which is thermodynamically stable in a membrane. This is typically an alpha helix comprising of several hydrophobic residues. The transmembrane domain of any transmembrane protein can be used to supply the transmembrane portion of the CAR. The presence and span of a transmembrane domain of a protein can be determined by those skilled in the art using the TMHMM algorithm (www.cbs.dtu.dk/services/TMHMM-2.0. Alternatively, an artificially designed TM domain may be used.

The transmembrane domain may be derived from CD28, which gives good receptor stability.

The endodomain is the signal-transmission portion of the CAR. It may be part of or associate with the intracellular domain of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain may comprise:
(i) an ITAM-containing endodomain, such as the endodomain from CD3 zeta; and/or
(ii) a co-stimulatory domain, such as the endodomain from CD28; and/or
(iii) a domain which transmits a survival signal, for example a TNF receptor family endodomain such as OX-40 or 4-1BB.

A number of systems have been described in which the antigen recognition portion is on a separate molecule from the signal transmission portion, such as those described in WO015/150771; WO2016/124930 and WO2016/030691. The CAR expressed by the cell of the present invention may therefore comprise an antigen-binding component comprising an antigen-binding domain and a transmembrane domain; which is capable of interacting with a separate intracellular signalling component comprising a signalling domain. The vector of the invention may express a CAR signalling system comprising such an antigen-binding component and intracellular signalling component.

The CAR may comprise a signal peptide so that when it is expressed inside a cell, the nascent protein is directed to the endoplasmic reticulum and subsequently to the cell surface, where it is expressed. The signal peptide may be at the amino terminus of the molecule.

T-Cell Receptor

One or more of the vector(s) of the kit of the invention may comprise a transgene encoding a T-cell receptor (TCR).

The TCR is a molecule found on the surface of T cells which is responsible for recognizing fragments of antigen as peptides bound to major histocompatibility complex (MHC) molecules.

The TCR is a heterodimer composed of two different protein chains. In humans, in 95% of T cells the TCR consists of an alpha ($\alpha$) chain and a beta ($\beta$) chain (encoded by TRA and TRB, respectively), whereas in 5% of T cells the TCR consists of gamma and delta ($\gamma/\delta$) chains (encoded by TRG and TRD, respectively).

When the TCR engages with antigenic peptide and MHC (peptide/MHC), the T lymphocyte is activated through signal transduction.

In contrast to conventional antibody-directed target antigens, antigens recognized by the TCR can include the entire array of potential intracellular proteins, which are processed and delivered to the cell surface as a peptide/MHC complex.

It is possible to engineer cells to express heterologous (i.e. non-native) TCR molecules by artificially introducing the TRA and TRB genes; or TRG and TRD genes into the cell using vector. For example the genes for engineered TCRs may be reintroduced into autologous T cells and transferred back into patients for T cell adoptive therapies.

Signal Transduction Modifying Protein

WO2016/193696 describes various fusion proteins and truncated proteins which modulate the signalling pathways following immune cell activation.

The transgene may for example, encode one of the following signal transduction modifying proteins:
(i) a truncated protein which comprises an SH2 domain from a protein which binds a phosphorylated immunoreceptor tyrosine-based activation motif (ITAM), but lacks a kinase domain;
(ii) a truncated protein which comprises an SH2 domain from a protein which binds a phosphorylated immunoreceptor tyrosine-based inhibition motif (ITIM) but lacks a phosphatase domain;
(iii) a fusion protein which comprises (a) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous domain.

The signal transduction modifying protein may be a truncated protein which comprises a ZAP70 SH2 domain but lacks a ZAP70 kinase domain.

The signal transduction modifying protein may be a fusion protein which comprises (i) an SH2 domain from a protein which binds a phosphorylated immunoreceptor tyrosine-based activation motif (ITAM); and (ii) a phosphatase domain.

The fusion protein may, for example, comprise a ZAP70 SH2 domain, a PTPN6 or an SHP-2 phosphatase domain.

The signal transduction modifying protein may be a fusion protein which comprises (i) an SH2 domain from a protein which binds a phosphorylated immunoreceptor tyrosine-based inhibition motif (ITIM); and (ii) a kinase domain.

The fusion protein may comprise an SH2 domain from PTPN6 or SHP-2.

The fusion protein may comprise a Zap70 kinase domain

The fusion protein may comprise an AKT or JAK kinase domain.

The signal transduction modifying protein may be a fusion protein which comprises (i) an SH2 domain from a protein which binds a phosphorylated immunoreceptor tyrosine-based activation motif (ITAM) or from a protein which binds a phosphorylated immunoreceptor tyrosine-based inhibition motif (ITIM); and (ii) a heterologous signalling domain.

The fusion protein may comprise an SH2 domain from ZAP70, PTPN6 or SHP-2.

The heterologous signalling domain may be from a signalling molecule which is not usually activated by an ITAM or ITIM containing receptor.

The heterologous signalling domain may be a co-stimulatory domain. In this respect, the fusion protein may comprise a CD28, OX40 or 41BB co-stimulatory domain.

The heterologous signalling domain may be an inhibitory domain. In this respect, the inhibitory domain may be or comprise the endodomain of CD148 or CD45. Alternatively, the heterologous signalling domain is or comprises the endodomain of ICOS, CD27, BTLA, CD30, GITR or HVEM.

The signal transduction modifying protein may be a fusion protein which comprises (i) an SH2 domain from a protein which binds a phosphorylated immunoreceptor tyrosine-based activation motif (ITAM); and (ii) an ITAM-containing domain.

The fusion protein may comprises a ZAP70 SH2 domain.

The ITAM-containing domain may be or comprise the endodomain of CD3-Zeta.

The signal transduction modifying protein may be a fusion protein which comprises (i) an SH2 domain from a protein which binds a phosphorylated immunoreceptor tyrosine-based inhibition motif (ITIM); and (ii) an ITIM-containing domain.

The fusion protein may comprise an SH2 domain from PTPN6 or SHP-2.

The ITIM-containing domain may be or comprise the endodomain from PD1, PDCD1, BTLA4, LILRB1, LAIR1, CTLA4, KIR2DL1, KIR2DL4, KIR2DL5, KIR3DL1 or KIR3DL3.

SRC Homology Region 2 Domain-Containing Phosphatase-1 (SHP-1)

The signal transduction modifying protein may be a modified form of SHP-1, which lacks a functional phosphatase domain. For example, the signal transduction modifying protein may be a truncated protein which comprises an SHP-1 SH2 but lacks a SHP-1 phosphatase domain.

SHP-1 is also known as tyrosine-protein phosphatase non-receptor type 6 (PTPN6). It is a member of the protein tyrosine phosphatase family.

The N-terminal region of SHP-1 contains two tandem SH2 domains which mediate the interaction of SHP-1 and its substrates. The C-terminal region contains a tyrosine-protein phosphatase domain.

SHP-1 is capable of binding to, and propagating signals from, a number of inhibitory immune receptors or ITIM containing receptors. Examples of such receptors include, but are not limited to, PD1, PDCD1, BTLA4, LILRB1, LAIR1, CTLA4, KIR2DL1, KIR2DL4, KIR2DL5, KIR3DL1 and KIR3DL3.

Human SHP-1 protein has the UniProtKB accession number P29350.

The signal transduction modifying protein may comprise or consist of a SHP-1 SH2 domain. In this respect, the STMP may comprise or consist of the sequence shown as SEQ ID NO: 35.

```
SHP-1 SH2 complete domain
                                         (SEQ ID NO: 35)
MVRWFHRDLSGLDAETLLKGRGVHGSFLARPSRKNQGDFSLSVRVGDQVT

HIRIQNSGDFYDLYGGEKFATLTELVEYYTQQQGVLQDRDGTIIHLKYPL

NCSDPTSERWYHGHMSGGQAETLLQAKGEPWTFLVRESLSQPGDFVLSVL

SDQPKAGPGSPLRVTHIKVMCEGGRYTVGGLETFDSLTDLVEHFKKTGIE

EASGAFVYLRQPYY
```

SHP-1 has two SH2 domains at the N-terminal end of the sequence, at residues 4-100 and 110-213 of the sequence shown therefore as SEQ ID No. 35. The STMP of the invention may therefore comprise one or both of the sequences shown as SEQ ID No. 36 and 37.

```
SHP-1 SH2 1
                                         (SEQ ID NO: 36)
WFHRDLSGLDAETLLKGRGVHGSFLARPSRKNQGDFSLSVRVGDQVTHIR

IQNSGDFYDLYGGEKFATLTELVEYYTQQQGVLQDRDGTIIHLKYPL

SHP-1SH22
                                         (SEQ ID No. 37)
WYHGHMSGGQAETLLQAKGEPWTFLVRESLSQPGDFVLSVLSDQPKAGPG

SPLRVTHIKVMCEGGRYTVGGLETFDSLTDLVEHFKKTGIEEASGAFVYL

RQPY
```

The STMP may comprise a variant of SEQ ID NO: 35, 36 or 37 having at least 80, 85, 90, 95, 98 or 99% sequence identity, provided that the variant sequence is a SH2 domain sequence capable of binding a pITIM domain. For example, the variant sequence may be capable of binding to the phosphorylated tyrosine residues in the cytoplasmic tail of PD1, PDCD1, BTLA4, LILRB1, LAIR1, CTLA4, KIR2DL1, KIR2DL4, KIR2DL5, KIR3DL1 or KIR3DL3. The variant sequence may be the equivalent sequence to of SEQ ID NO: 35, 36 or 37 when derived from isoform 2, 3 or 4 of SHP-1.

SHP-2

The signal transduction modifying protein may be a modified form of SHP-2, which lacks a functional phosphatase domain. For example, the signal transduction modifying protein may be a truncated protein which comprises an SHP-2 SH2 but lacks a SHP-2 phosphatase domain.

SHP-2, also known as PTPN11, PTP-1D and PTP-2C, is also a member of the protein tyrosine phosphatase (PTP) family. Like SHP-1, SHP-2 has a domain structure that consists of two tandem SH2 domains in its N-terminus followed by a protein tyrosine phosphatase (PTP) domain. In the inactive state, the N-terminal SH2 domain binds the PTP domain and blocks access of potential substrates to the active site. Thus, SHP-2 is auto-inhibited. Upon binding to target phospho-tyrosyl residues, the N-terminal SH2 domain is released from the PTP domain, catalytically activating the enzyme by relieving the auto-inhibition.

Human SHP-2 has the UniProtKB accession number P35235-1.

The signal transduction modifying protein may comprise or consist of a SHP-2 SH2 domain. In this respect, the STMP may comprise or consist of the first SH2 domain of SHP-2, for example comprising amino acids 6-102 of SEQ ID NO. 5 or the second SH2 domain of SHP-2, for example comprising amino acids 112-216 of SHP-2. The STMP may comprise or consist of the sequence shown as SEQ ID NO: 38, 39 or 40. The STMP may comprise a variant of SEQ ID NO: 38, 39 or 40 having at least 80, 85, 90, 95, 98 or 99% sequence identity, provided that the variant sequence is a SH2 domain sequence capable of binding a pITIM domain. For example, the variant sequence may be capable of binding to the phosphorylated tyrosine residues in the cytoplasmic tail of PD1, PDCD1, BTLA4, LILRB1, LAIR1, CTLA4, KIR2DL1, KIR2DL4, KIR2DL5, KIR3DL1 or KIR3DL3. The variant sequence may be the equivalent sequence to of SEQ ID NO: 38, 39 or 40 when derived from isoform 2 or 3 of SHP-2.

```
SHP-2 first SH2 domain
                                    (SEQ ID NO: 38)
WFHPNITGVEAENLLLTRGVDGSFLARPSKSNPGDFTLSVRRNGAVTHIK

IQNTGDYYDLYGGEKFATLAELVQYYMEHHGQLKEKNGDVIELKYPL

SHP-2 second SH2 domain
                                    (SEQ ID No. 39)
WFHGHLSGKEAEKLLTEKGKHGSFLVRESQSHPGDFVLSVRTGDDKGESN

DGKSKVTHVMIRCQELKYDVGGGEREDSLTDLVEHYKKNPMVETLGTVLQ

LKQPL

SHP-2 both SH2 domains
                                    (SEQ ID No. 40)
WFHPNITGVEAENLLLTRGVDGSFLARPSKSNPGDFTLSVRRNGAVTHIK

IQNTGDYYDLYGGEKFATLAELVQYYMEHHGQLKEKNGDVIELKYPLNCA

DPTSERWFHGHLSGKEAEKLLTEKGKHGSFLVRESQSHPGDFVLSVRTGD

DKGESNDGKSKVTHVMIRCQELKYDVGGGERFDSLTDLVEHYKKNPMVET

LGTVLQLKQPL
```

The expression of a signal transduction modifying protein which comprises a modified or truncated SHP-1 or SHP-2 with an inactive or removed phosphatase domain can help counteract a hostile microenvironment for example due to PD-L1 overexpression. In solid cancers such as prostate cancer, the microenvironment may be particularly hostile due to PDL1 over-expression; in this case a decision might be made to include a truncated SHP-1 or SHP-2 as a transgene in the kit of vectors.

TGF Beta/TGF Beta Receptor

The transgene may encode a protein capable of enhancing proliferation of cells such as T cells. For example, the transgene may encode a mutant version of transforming growth factor beta which inhibits TGFbeta secretion or action.

Lopez et al ((1992) Mol. Cell Biol. 12:1674-9) describe dominant negative mutants of TGFbeta 1 comprising mutations in the precursor domain.

Alternatively that transgene may encode a dominant-negative version of a TGF beta receptor, such as a truncated TGF beta receptor A truncated TGF beta receptor 2 may comprise the sequence shown as SEQ ID No. 41.

```
                                    SEQ ID No. 41
MGWSCIILFLVATATGVHSTIPPHVQKSVNNDMIVTDNNGAVKFPQLCKF

CDVRFSTCDNQKSCMSNCSITSICEKPQEVCVAVWRKNDENITLETVCHD

PKLPYHDFILEDAASPKCIMKEKKKPGETFFMCSCSSDECNDNIIFSEEY

NTSNPDLLLVIFQVTGISLLPPLGVAISVIIIFYCYRVNRQQKLSS
```

In this sequence:

The leader sequence from murine Ig heavy chain V region 102 (Uniprot; P01750) is in bold.

TGFβRII ectodomain is in normal text (Uniprot; P37173)

TGFβRII transmembrane domain is underlined.

TGFβRII truncated cytoplasmic domain is in italics.

The expression of a dominant negative TGF beta or TGF beta receptor can help counteract a hostile microenvironment for example due to TGFbeta overexpression. In this case a decision might be made to include expression of a dominant-negative TGFbeta or TGFBeta receptor as a transgene.

Dampener

In an alternative embodiment, the transgene may encode a phosphatase "damper" which causes dephosphorylation of a CAR or TCR endodomain, raising the threshold to activation in certain transcriptional states.

The dampener may be a membrane-tethered signal-dampening component (SDC) comprising a signal-dampening domain (SDD).

The SDD may be capable of inhibiting the intracellular signalling domain of the CAR.

The SDD may comprise a phosphatase domain capable of dephosphorylating immunoreceptor tyrosine-based activation motifs (ITAMs), for example the endodomain of CD148 or CD45 or the phosphatase domain of SHP-1 or SHP-2.

The SDD may comprise an immunoreceptor tyrosine-based inhibition motif (ITIM), for example the SDD may comprise an endodomain from one of the following inhibitory receptors: PD1, BTLA, 2B4, CTLA-4, GP49B, Lair-1, Pir-B, PECAM-1, CD22, Siglec 7, Siglec 9, KLRG1, ILT2, CD94-NKG2A and CD5.

The SDD may inhibits a Src protein kinase, such as Lck.

The SDD may comprise the kinase domain of CSK.

The membrane-tethered SDC may, for example, comprise a transmembrane domain or a myristoylation sequence.

The dampener may be inducible, for example, by the addition of a small molecule. Various inducible dampener systems are described in GB1707780.1, GB1707781.9 and GB1707783.5.

Inhibitory CAR

The transgene may encode an inhibitory CAR, i.e. a CAR which comprises an inhibitory endodomain. Inhibitory CARs are described in WO2015/075470. The inhibitory endodomain may comprise a protein-tyrosine phosphatase (PTP), such as the PTP domain from SHP-1 or SHP-2.

Alternatively, the inhibitory endodomain may comprise an ITIM (Immunoreceptor Tyrosine-based Inhibition motif) containing endodomain such as that from CD22, LAIR-1, the Killer inhibitory receptor family (KIR), LILRB1, CTLA4, PD-1, BTLA etc. When phosphorylated, ITIMs recruits endogenous PTPN6 through its SH2 domain. If co-localised with an ITAM containing endodomain, dephosphorylation occurs and the activating CAR or TCR is inhibited.

Alternatively, the inhibitory CAR may comprise a phosphatase domain capable of dephosphorylating immunoreceptor tyrosine-based activation motifs (ITAMs), for example the endodomain of CD148 or CD45 or the phosphatase domain of SHP-1 or SHP-2.

Cytokines, Cytokine Receptors, Cytokine Signalling Domains and Chimeric Cytokine Receptors The transgene may encode a cytokine such as IL-2, IL-7, IL-12 or IL-15.

The transgene may encode a cytokine receptor.

The transgene may encode a protein comprising a cytokine receptor endodomain.

The transgene may encode a chimeric cytokine receptor which comprises an exodomain which binds to a target antigen, such as a tumour secreted antigen, a tumour antigen or a chemokine and a cytokine receptor endodomain. Chimeric cytokine receptors are described in more detail in WO2017/029512.

JAK/STAT

The transgene may encode a constitutively active or inducible Signal Transducer and Activator of Transcription (STAT) molecule or a constitutively active or inducible Janus Kinase (JAK) molecule. Examples of such molecules are given in GB1714718.2.

The cassette may comprise a first transgene encoding a first STAT polypeptide comprising a first dimerizing domain (DD) and a second transgene encoding a second STAT polypeptide comprising a second DD, which specifically binds to the first DD. Binding of the first and second DDs may be inducible with an agent.

A constitutively active STAT molecule may comprise a gain-of-function mutation.

Suicide Switch

The transgene may be suicide-gene, which is a genetically encoded mechanism which allows selective destruction of adoptively transferred T-cells in the face of unacceptable toxicity. Two suicide-genes have been tested in clinical studies: Herpes Simplex Virus thymidine kinase (HSV-TK) and inducible caspase 9 (iCasp9).

The herpes simplex virus I-derived thymidine kinase (HSV-TK) gene has been used as an in vivo suicide switch in donor T-cell infusions to treat recurrent malignancy and Epstein Barr virus (EBV) lymphoproliferation after hemopoietic stem cell transplantation.

The activation mechanism behind Caspase 9 was exploited in the original iCasp9 molecule. All that is needed for Caspase 9 to become activated, is overcoming the energic barrier for Caspase 9 to homodimerize. The homodimer undergoes a conformational change and the proteolytic domain of one of a pair of dimers becomes active. Physiologically, this occurs by binding of the CARD domain of Caspase 9 to APAF-1. In iCasp9, the APAF-1 domain is replaced with a modified FKBP12 which has been mutated to selectively bind a chemical inducer of dimerization (CID). Presence of the CID results in homodimerization and activation. iCasp9 is based on a modified human caspase 9 fused to a human FK506 binding protein (FKBP) (Straathof et al (2005) Blood 105:4247-4254). It enables conditional dimerization in the presence of a small molecule CID, known as AP1903.

An alternative caspase-based suicide gene is described in WO2016/135470. The transgene may encode a suicide gene having the general structure: FRB-FKBP12-dCasp9 or FKBP12-FRB-dCasp9. For example, the transgene may encode the amino acid sequence shown as SEQ ID No. 42.

```
(FRB-FKBP12-L3-dCasp9)
                                         SEQ ID No. 42
<----------------------FRB----------------------
MASRILWHEMWHEGLEEASRLYFGERNVKGMFEVLEPLHAMMERGPQTLK ---------------------------FRB------------------>
ETSFNQAYGRDLMEAQEWCRKYMKSGNVKDLLQAWDLYYHVFRRISKLEY <L1-><---FKBP12----------------------FKBP12------
SGGGSLEGVQVETISPGDGRTFPKRGQTCVVHYTGMLEDGKKFDSSRDRN --------------------------------------------------
KPFKFMLGKQEVIRGWEEGVAQMSVGQRAKLTISPDYAYGATGHPGIIPP -------------><------L3-------><---dCasp9----------
HATLVFDVELLKLESGGGGSGGGGSGGGGSGVDGFGDVGALESLRGNADL ---------------dCasp9-------------------------
AYILSMEPCGHCLIINNVNFCRESGLRTRTGSNIDCEKLRRRFSSLHFMV -------------------------dCasp9--------------------
EVKGDLTAKKMVLALLELAQQDHGALDCCVVVILSHGCQASHLQFPGAVY ----------------------------------dCasp9----------
GTDGCPVSVEKIVNIFNGTSCPSLGGKPKLFFIQACGGEQKDHGFEVAST -----------------------------------------------dCasp9
SPEDESPGSNPEPDATPFQEGLRTFDQLDAISSLPTPSDIFVSYSTFPGF -----------------------------------------------dCasp9
VSWRDPKSGSWYVETLDDIFEQWAHSEDLQSLLLRVANAVSVKGIYKQMP

----------------->
GCFNFLRKKLFFKTSAS
```

The transgene may encode the sort-suicide gene known as RQR8 which described in WO2013/153391, which comprises the amino acid sequence shown as SEQ ID No. 43

```
                                         SEQ ID No. 43
CPYSNPSLCSGGGGSELPTQGTFSNVSTNVSPAKPTTTACPYSNPSLCSG

GGGSPAPRPPTPAPTIASQPLSLRPEACRPAAGGAVHTRGLDFACDIYIW

APLAGTCGVLLLSLVITLYCNHRNRRRVCKCPRPVV
```

Cells comprising this suicide gene may be deleted by the administration of Rituximab.

The transgene may encode a suicide switch which comprises a multi-spanning transmembrane protein, such as CD20, fused to a FAS endodomain. When expressed at the cell surface, the multi-spanning transmembrane protein binds an extracellular ligand, leading to activation of the FAS endodomain. These systems are described in more detail in WO2016/174408.

Co-Expression

In the cassettes and vectors of the invention, the nucleic acid sequences may be connected by sequences enabling co-expression of the transgene sequences as separate polypeptides. For example, the nucleic acid may encode a cleavage site between two transgenes; or two cleavage sites, enabling the production of three transgenes as discrete polypeptides. The cleavage site may be self-cleaving, such that when the compound polypeptide is produced, it is immediately cleaved into the separate components without the need for any external cleavage activity.

Various self-cleaving sites are known, including the Foot-and-Mouth disease virus (FMDV) 2a self-cleaving peptide, which may have one of the following sequences:

```
                            SEQ ID NO: 44
RAEGRGSLLTCGDVEENPGP.
or
                            SEQ ID NO: 45
QCTNYALLKLAGDVESNPGP
```

The co-expression sequence may alternatively be an internal ribosome entry sequence (IRES) or an internal promoter.

Cell

The present invention provides a cell which comprises a transgene and a nucleotide sequence encoding a non-endogenous transcription factor, wherein expression of the transgene is dependent upon expression of the non-endogenous transcription factor.

The present invention provides a cell transfected or transduced with a kit of vectors of the invention.

The cell may be a cytolytic immune cell.

Cytolytic immune cells can be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner.

NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

Cells of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, the cells may be derived from ex vivo differentiation of inducible progenitor cells or embryonic progenitor cells to, for example, T cells. Alternatively, an immortalized cell line which retains its lytic function and could act as a therapeutic may be used.

Method for Making Cell or Cell Composition

The invention also provides a method for making a cell which comprises that step of transducing or transfecting a cell with a kit of vectors of the invention.

The cell may be a cell isolated from a subject. The cell may be transfected or transduced in vitro or ex vivo.

Successful transduction or transfection with both or all of the vectors in the kit may be determined by detecting expression of the marker gene, or by selection based on expression of the marker gene.

The invention also provides a method for making a cell composition expressing a kit of vectors of the invention, which comprises the following steps:

(i) transducing or transfecting a cell with a kit of vectors as described herein wherein one of the vectors comprises a marker gene; and
(ii) selecting cells which express the marker gene wherein expression of the marker gene by a cell indicates that the comprises both or all of the vectors in the kit.

The cell(s) is/are transduced or transfected ex vivo.

The invention also a method for selecting cells transduced with both or all of the vectors of the first aspect of the invention which comprises the step of selecting cells based on the expression of a marker gene.

Composition

The present invention also relates to a pharmaceutical composition containing a plurality of cells of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The cells of the present invention may be capable of killing target cells, such as cancer cells.

The cells of the present invention may be used for the treatment of an infection, such as a viral infection.

The cells of the invention may also be used for the control of pathogenic immune responses, for example in autoimmune diseases, allergies and graft-vs-host rejection.

The cells of the invention may be used for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

The cells of the invention may be used to treat: cancers of the oral cavity and pharynx which includes cancer of the tongue, mouth and pharynx; cancers of the digestive system which includes oesophageal, gastric and colorectal cancers; cancers of the liver and biliary tree which includes hepatocellular carcinomas and cholangiocarcinomas; cancers of the respiratory system which includes bronchogenic cancers and cancers of the larynx; cancers of bone and joints which includes osteosarcoma; cancers of the skin which includes melanoma; breast cancer; cancers of the genital tract which include uterine, ovarian and cervical cancer in women, prostate and testicular cancer in men; cancers of the renal tract which include renal cell carcinoma and transitional cell carcinomas of the utterers or bladder; brain cancers including gliomas, glioblastoma multiforme and medullobastomas; cancers of the endocrine system including thyroid cancer, adrenal carcinoma and cancers associated with multiple endocrine neoplasm syndromes; lymphomas including Hodgkin's lymphoma and non-Hodgkin lymphoma; Multiple Myeloma and plasmacytomas; leukaemias both acute and chronic, myeloid or lymphoid; and cancers of other and unspecified sites including neuroblastoma.

The invention will now be further described by way of Examples, which are meant to serve to assist one of ordinary skill in the art in carrying out the invention and are not intended in any way to limit the scope of the invention.

EXAMPLES

Example 1—Design and Testing of a Kit of Two Vectors where Expression of a Transgene from One Vector is Dependent on Expression of a Transcription Factor by the Other Vector A primary cassette is generated using a retroviral transfer vector where expression is driven by the long terminal repeat of Monkey Moloney leukemia virus (MoMLV). The transgene of the primary cassette consists of the marker gene RQR8 followed by a FMD 2A like peptide and a CAR targeting GD2 followed by a further 2A peptide and a GAL4/VP16 transcription factor. A second cassette is generated using a self-inactivating retroviral transfer vector where expression is driven by a promoter comprising a GAL4 5×upstream activating sequence. The transgene consists of a second marker gene—truncated NGFR and a truncated SHP2. T-cells are transduced with either primary or the secondary cassette or both together. Non-transduced and transduced T-cells are analysed by flow-cytometry after staining for both marker genes.

Example 2—Design and Testing of a Transcriptional Circuit Using a GAL4 System

The GAL4 system utilises the DNA-binding domain of the yeast transcription factor GAL4, which induces the expression of genes involved in metabolising galactose to glucose. In the presence of glucose the GAL4 transcription factor is repressed and this results in the cessation of expression of the GAL4-responsive genes. The DNA sequence recognised by the GAL4 transcription factor and its functional domains (DNA-binding domain and transcriptional activation domain) have been well defined and exploited in the yeast two-hybrid system, which identifies protein-protein interactions.

The GAL4 transcriptional-dependent circuit utilises a chimeric GAL4 transcription factor consisting of the trans-action domain (TAD) of the herpes simplex viral protein 16 (VP-16) fused to the DNA-binding domain (DBD) of GAL4 and a GAL4 UAS promoter containing five copies of the GAL4 DNA binding site. The VP16-GAL4 chimeric transcription factor and the GAL4 UAS promoter are present in separate retroviral vectors. This restricts transcriptional activity to cells co-transduced with both retroviruses, because in the absence of one of the components there is no transcription from the GAL4 UAS promoter.

Constructs

The sequences encoding the chimeric VP16-GAL4 transcription factor or the GAL4 DNA-binding domain alone were cloned into the retroviral vector SFGmR downstream of the sort selection marker RQR8 (constructs AU47529 and AU47530, respectively). A self-cleaving 2A peptide sequence was placed between RQR8 and the GAL transcription factor to enable expression of both polypeptides.

Figure 6:
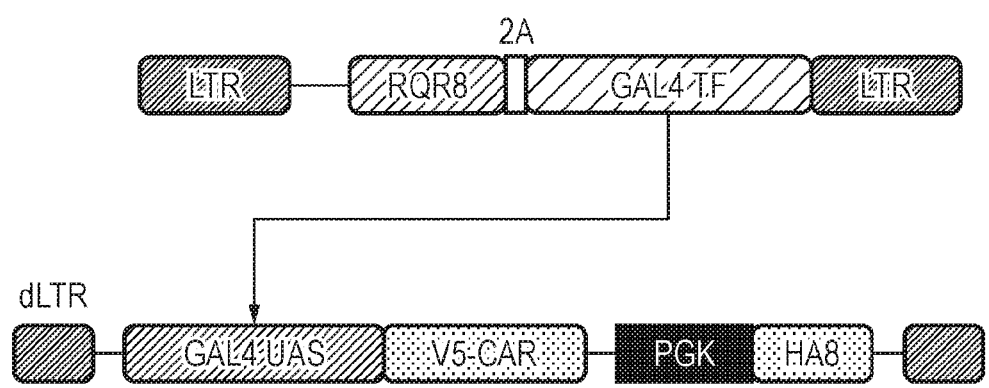
FIG. 6—Diagram illustrating the structure of the GAL4 system constructs described in Example 2

To enable expression from the GAL4 UAS without interference transcriptional interference from the viral LTRs, the promoter sequence was cloned into the self-inactivating (SIN) retroviral vector pSuper upstream of a V5-tagged anti-CD19 CAR (a second generation CAR with anti-CD19 CAT19 scFv fused to the human CD8a stalk and transmembrane domains and 4-1BB and CD3ζ signalling domains). Within the pSuper SIN retroviral construct there is a human phosphoglycerate kinase (PGK) promoter that drives the expression of a cell surface marker consisting of a HA epitope presented on a human CD8a stalk (HA8), which enables detection of transduced cells (Table 1 and FIG. 6).

TABLE 1

Description of GAL4 system constructs

| Number | Plasmid name | Description |
|---|---|---|
| AU47529 | SFGmR.RQR8-2A-VP16-GAL4 | Retroviral construct expressing RQR8 sort selection marker and active VP16-GAL4 transcription factor |

TABLE 1-continued

Description of GAL4 system constructs

| Number | Plasmid name | Description |
| --- | --- | --- |
| AU47530 | SFGmR.RQR8-2A-GAL4 | Control retroviral construct expressing RQR8 sort selection marker and inactive GAL4 transcription factor consisting of DBD alone |
| AU47531 | pSuperRetroW.RheoRE.V5-aCD19_CAT19-CD8STK-CD8TM-41BBz.PGK.HA8 | Self-inactivating (SIN) retroviral vector containing GAL4 UAS driving the expression of a V5-tagged anti-CD19 CAR. An internal PGK promoter drives the expression of an HA8 marker (HA epitope presented on a human CD8a stalk). |

Methods

Retroviral supernatant was prepared by transfecting 293T cells with the SFGmR or pSuper retroviral constructs and a mixture of packaging constructs (gag/pol and the glycoprotein RDF114). Activated human peripheral blood mononuclear cells (PBMCs) were transduced with retroviral particles generated from the genome vectors described above and flow cytometry carried out on stained cells 72 hours after transduction. Staining was carried out using Alexa-488 conjugated anti-HA epitope, PE-conjugated anti-CD34 QBend10, and APC conjugated anti-V5 epitope antibodies. The anti-CD34 and anti-HA antibodies detected the RQR8 sort selection and HA8 markers, respectively, expressed on the surface of transduced cells. The V5 epitope antibody detected the V5-tagged anti-CD19 CAR, whose expression was driven from the UAS promoter in cells co-transduced with both the transcription factor and promoter constructs.

Results

Peripheral blood mononuclear cells were stained with antibodies recognising epitopes present on the RQR8 and HA8 markers and the V5-tagged CAR and analysed by flow cytometry to detect transduced cells. Expression of RQR8 (driven by the retroviral LTR) was readily detectable, with between 53 to 65% of the singularly transduced cells expressing the marker. Co-transduced PBMCs were shown to express both the RQR8 and HA8 markers.

Flow cytometric analysis of PBMCs for expression of the V5-tagged showed that there was a a mean 15-fold increase in the level of expression of the V5-tagged CAR on PBMCs co-transduced with the GAL4 UAS construct and the transcriptionally active VP16-GAL4 transcription factor, with 24% of cells being V5+ (FIGS. 7 and 8). These results indicate that expression of the V5-tagged CAR was restricted to PBMCs co transduced with the GAL4 UAS promoter and the transcriptionally active VP16-GAL4 chimeric transcription factor. This means that the expression of CARs and auxiliary modules can be restricted by separating the components on to two retroviral constructs and co-transducing PBMCs.

Example 3—Design and Testing of a Transcriptional Circuit Using a LexA System

The LexA system utilises the LexA transcription factor from *E. coli* that regulates the expression of genes involved in DNA repair (SOS response). LexA recognises a 22 base pair DNA sequence referred to as the LexA operator sequence.

Constructs

Similar to the GAL4 system, the LexA transcriptional dependent circuit consisted of a LexA UAS cloned into a SIN retroviral construct that contained the V5-tagged anti-CD19 CAR. The SIN retroviral construct also contained a human phosphoglycerate kinase (PGK) promoter that drives the expression of a cell surface marker consisting of an HA epitope presented on a human CD8a stalk (HA8), which enables detection of transduced cells. Transcription from the LexA UAS is driven by a chimeric transcription factor consisting of the transactivation domain of VP16 fused to the DNA-binding domain of LexA from *E. coli* (Table 2 and FIG. 9).

TABLE 2

LexA constructs

| Number | Plasmid name | Description |
| --- | --- | --- |
| AU47534 | SFGmR.RQR8-2A-LexA | Retroviral construct expressing RQR8 sort selection marker and active VP16-LexA transcription factor |
| AU47533 | SFGmR.RQR8-2A-VP16-LexA | Control retroviral construct expressing RQR8 sort selection marker and inactive LexA transcription factor consisting of DBD alone |
| AU49052 | pSERS11.LexA_UAS.V5-aCD19_CAT19-CD8STK-CD8TM-41BBz.PGK.HA8 | Self-inactivating (SIN) retroviral vector containing LexA UAS driving the expression of a V5-tagged anti-CD19 CAR. An internal PGK promoter drives the expression of an HA8 marker (HA epitope presented on a human CD8a stalk). |

Results

Transduced PBMC5 were analysed for expression of the transduction markers (RQR8 and HA8) and the V5-tagged CAR. Staining of the PBMC5 with antibodies to V5 demonstrated that there was a significant increase in expression when PBMC5 were co-transduced with the active VP16-LexA chimeric transcription factor and LexA UAS promoter construct (FIG. 10).

Example 4—Design and Testing of a Transcriptional Circuit Using a QF System

The QF system is derived from qa cluster transcription factors controlling the metabolism of quinic acid in the fungus *Neurospora crassa*. The transcription factor QF positively regulates the expression of genes involved in metabolising quinic acid and the functional domains of the transcription factor have been defined. QF comprises an N-terminal DNA-binding domain, a central domain, proposed to be involved in transcription factor dimerization, and a C-terminal transactivation domain. As the DNA-binding domains and transactivation domains of QF are defined, it is possible to generate a more compact artificial transcription factor, consisting of DBD and TAD fused together, which is considerably smaller than the endogenous transcription factor. This artificial transcription factor is referred to as QF2.

Constructs

The QF2 system is similar to the GAL4 and LexA systems and comprises a retroviral construct expressing the artificial transcription factor and the sort selection marker RQR8 and a SIN retroviral construct with QF2 UAS promoter (QUAS) driving the expression of a V5-tagged anti-CD19 CAR and a PGK promoter controlling the expression of a HA8 marker (Table 3 and FIG. 11).

Flow cytometric analysis of stained PBMC5 with antibodies to HA and RQR8 was carried out to identify transduced populations. Co-transduction of the active QF2 transcription factor with the QUAS promoter construct resulted in the robust expression of the V5-tagged anti-CD19 CAR that was 8-fold higher than controls (FIG. 13). In contrast, V5-tagged anti-CD19 CAR expression was low in PBMC5 transduced with QUAS promoter construct alone or in combination with the inactive form of the QF2 transcription factor (QF2-dTAD). Together these results indicate that the QF2 transcription factor is functional in T cells and is capable of driving the expression of a transgene encoding a CAR.

Example 5—Design and Testing of a Circular Transcriptional-Dependent Circuit

Circular transcriptional circuits can be generated using a pair of SIN retroviral constructs exhibiting leaky expression from the truncated LTR. Each SIN retroviral construct possesses a UAS with binding sites for an artificial transcription factor, such as GAL4 or LexA, which drives the expression of a marker and/or CAR and an artificial transcription factor. The constructs are designed such that each will have the artificial transcription factor binding to the UAS of the other construct. In this situation, leaky expression from the SIN retroviral construct should lead to the expression of the artificial transcription factor and if the cell is co-transduced with both constructs this should establish a self-amplifying loop that will drive expression from both constructs.

Constructs

The constructs for the circular transcriptional dependent circuit were generated by modifying the previously described constructs (Table 4 and FIG. 13).

TABLE 3

| QF2 constructs | | |
| --- | --- | --- |
| Number | Plasmid name | Description |
| AU52483 | SFGmR.RQR8-2A-QF2 | Retroviral construct expressing RQR8 sort selection marker and active QF2 transcription factor |
| AU52484 | SFGmR.RQR8-2A-QF2_dTAD | Control retroviral construct expressing RQR8 sort selection marker and inactive QF2 transcription factor consisting of DBD alone |
| AU52485 | pSERS11.QUAS.V5-aCD19_CAT19_CD8STK-41BBz.PGK.HA8-2A-M2 | Self-inactivating (SIN) retroviral vector containing QUAS driving the expression of a V5-tagged anti-CD19 CAR. An internal PGK promoter drives the expression of an HA8 marker (HA epitope presented on a human CD8a stalk). |

TABLE 4

| Circular transcriptional dependent circuit constructs | | |
|---|---|---|
| Number | Plasmid name | Description |
| AU52320 | pSuperRetroW.LexA.RQR8-2A-GAL4 | SIN retroviral vector containing LexA UAS driving the expression of a RQR8 and GAL4 DNA-binding domain |
| AU52321 | pSuperRetroW.LexA.RQR8-2A-VP16-GAL4 | SIN retroviral vector containing LexA UAS driving the expression of a RQR8 and active VP16-GAL4 chimeric transcription factor |
| AU52329 | pSERS11.Rheo.V5-aCD19_CAT19-CD8STK-41BBz-E2A-HA8-T2A-LexA | SIN retroviral vector containing GAL4 UAS driving the expression of a V5-tagged anti-CD19 CAR, HA8 marker and LexA DNA-binding domain. |
| AU52330 | pSERS11.Rheo.V5-aCD19_CAT19-CD8STK-41BBz-E2A-HA8-T2A-VP16-LexA | SIN retroviral vector containing GAL4 UAS driving the expression of a V5-tagged anti-CD19 CAR, HA8 marker and active VP16-LexA chimeric transcription factor. |

Methods

Retroviral supernatants were generated as described before and used to transduce 293T cells. After 72 hours of transduction the cells were stained with antibodies to the HA8 marker, RQR8 and the V-tagged anti-CD19 CAR.

Results

Flow cytometric analysis of 293T cells transduced with the individual components of the circular transcriptional dependent circuit showed that expression of the RQR8 and HA8 markers was low, indicating a low level of leaky transcription from the LTRs of the SIN retroviral constructs. When cells were co-transduced with constructs expressing active VP16-GAL4 transcription factor and the GAL4 UAS construct, a higher level of expression of the HA8 marker was observed. To determine if the V5-tagged anti-CD19 CAR was also expressed in the transduced cells, staining with an antibody to the V5 tag and flow cytometric analysis was carried out. This demonstrated that when cells were co-transduced with constructs containing the V5-tagged anti-CD19 CAR under the control of the GAL4 UAS and another construct containing the active VP16-GAL4 transcription factor there was an increase in expression of the CAR with levels 7 to 14-fold higher than those of the single transduction controls.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for treating a disease by killing target cells in a subject, which comprises the following steps:
   (a) isolation of a T cell-containing sample from a subject,
   (b) transduction or transfection of T cells of the sample with a kit of vectors comprising:
      (i) a first vector which comprises a first transgene which encodes a chimeric antigen receptor (CAR) which binds an antigen expressed on the target cells and a nucleotide sequence encoding a transcription factor, and
      (ii) a second vector which comprises a second transgene which encodes an entity of interest (EOI) and a marker gene
      wherein expression of the second transgene within the T cell is dependent upon expression of the transcription factor,
   or
      (i) a first vector which comprises a first transgene which encodes a chimeric antigen receptor (CAR) which binds an antigen expressed on the target cells and a nucleotide sequence encoding a first transcription factor,
      (ii) a second vector which comprises a second transgene which encodes an entity of interest (EOI) and a nucleotide sequence encoding a second transcription factor, and
      (iii) a third vector which comprises a third transgene which encodes an entity of interest (EOI) and a marker gene
      wherein expression of the second transgene within the T cell is dependent upon expression of the first transcription factor, and expression of the third transgene within the T cell is dependent upon expression of the second transcription factor,
   (c) selecting T cells which express the marker gene, and
   (d) administering the T cells selected from step (c) to the subject to kill the target cells.

2. The method of claim 1, wherein the disease is cancer.

* * * * *